(12) United States Patent
Nichols

(10) Patent No.: US 11,854,702 B2
(45) Date of Patent: Dec. 26, 2023

(54) CONNECTED BODY SURFACE CARE MODULE

(71) Applicant: PREH HOLDING, LLC, Laguna Niguel, CA (US)

(72) Inventor: Thomas Nichols, Laguna Niguel, CA (US)

(73) Assignee: PREH HOLDING, LLC, Laguna Niguel, CA (US)

( * ) Notice: Subject to any disclaimer, the term of this patent is extended or adjusted under 35 U.S.C. 154(b) by 0 days.

(21) Appl. No.: 18/183,849

(22) Filed: Mar. 14, 2023

(65) Prior Publication Data

US 2023/0215582 A1 Jul. 6, 2023

Related U.S. Application Data

(63) Continuation of application No. 17/806,846, filed on Jun. 14, 2022.

(Continued)

(51) Int. Cl.
*A61M 1/00* (2006.01)
*A61F 13/00* (2006.01)
(Continued)

(52) U.S. Cl.
CPC .......... *G16H 50/30* (2018.01); *A61B 5/0013* (2013.01); *A61B 5/0077* (2013.01); *A61B 5/445* (2013.01); *A61B 5/4836* (2013.01); *A61B 5/4842* (2013.01); *A61B 5/6833* (2013.01); *A61B 5/7267* (2013.01); *A61F 13/00068* (2013.01); *A61M 1/90* (2021.05); *A61M 1/915* (2021.05); *G06T 7/0014* (2013.01); *G06V 10/764* (2022.01); *G06V 10/774* (2022.01); *G16H 20/00* (2018.01); *G16H 40/63* (2018.01);
(Continued)

(58) Field of Classification Search
CPC .... A61F 13/00068; A61F 2013/00536; A61M 1/90; A61M 35/00; A61N 5/06; A61N 2007/0017; G16H 50/30; G16H 40/63; G16H 50/20; A61B 5/00; A61B 5/441; A61B 5/445
See application file for complete search history.

(56) References Cited

U.S. PATENT DOCUMENTS 6,283,938 B1 9/2001 McConnell
6,607,387 B2 8/2003 Mault
(Continued)

FOREIGN PATENT DOCUMENTS

WO  WO 2022/264423  12/2020

OTHER PUBLICATIONS

Wang et al., "A Unified Framework for Automatic Wound Segmentation and Analysis with Deep Convolutional Neural Networks," 2015 37th Annual International Conference of the IEEE Engineering in Medicine and Biology Society, 2015, pp. 2415-2418.

*Primary Examiner* — Jessica Arble
(74) *Attorney, Agent, or Firm* — Knobbe, Martens, Olson & Bear, LLP

(57) ABSTRACT

A wearable treatment and analysis module is provided. The module is positioned on or near a body surface region of interest. The module provides remote access to sensor data, treatment administration, and/or other health care regimens via a network connection with a user device and/or management system.

30 Claims, 27 Drawing Sheets

Related U.S. Application Data

(60) Provisional application No. 63/267,475, filed on Feb. 2, 2022, provisional application No. 63/266,392, filed on Jan. 4, 2022, provisional application No. 63/202,506, filed on Jun. 14, 2021.

(51) Int. Cl.
| | |
|---|---|
| *A61M 35/00* | (2006.01) |
| *G16H 50/30* | (2018.01) |
| *G16H 50/20* | (2018.01) |
| *G16H 40/63* | (2018.01) |
| *G16H 70/60* | (2018.01) |
| *G16H 20/00* | (2018.01) |
| *G06V 10/774* | (2022.01) |
| *G06V 10/764* | (2022.01) |
| *A61B 5/00* | (2006.01) |
| *G06T 7/00* | (2017.01) |
| *H04N 7/18* | (2006.01) |
| *A61N 5/06* | (2006.01) |
| *A61N 7/00* | (2006.01) |

(52) U.S. Cl.
CPC ............ *G16H 50/20* (2018.01); *G16H 70/60* (2018.01); *H04N 7/183* (2013.01); *A61B 2562/06* (2013.01); *A61B 2576/00* (2013.01); *A61F 2013/00536* (2013.01); *A61M 35/00* (2013.01); *A61M 2205/3306* (2013.01); *A61N 5/06* (2013.01); *A61N 2007/0017* (2013.01); *G06T 2207/20081* (2013.01); *G06T 2207/30088* (2013.01); *G06V 2201/03* (2022.01)

(56) References Cited

U.S. PATENT DOCUMENTS

| | | |
|---|---|---|
| 6,638,231 B2 | 10/2003 | Govari et al. |
| 6,889,165 B2 | 5/2005 | Lind et al. |
| 7,193,219 B2 | 3/2007 | Schick et al. |
| 8,062,220 B2 | 11/2011 | Kurtz et al. |
| 8,073,223 B2 | 12/2011 | Wilson et al. |
| 8,094,009 B2 | 1/2012 | Allen et al. |
| 8,372,128 B2 | 2/2013 | Reuben |
| 8,915,866 B2 | 12/2014 | Nycz |
| 9,028,405 B2 | 5/2015 | Tran |
| 9,042,967 B2 | 5/2015 | Dacosta et al. |
| 9,204,830 B2 | 12/2015 | Zand |
| 9,259,163 B2 | 2/2016 | Rajan |
| 9,369,170 B2 | 6/2016 | Sorrentino |
| 9,603,524 B2 | 3/2017 | Park et al. |
| 9,629,561 B2 | 4/2017 | Weinstein et al. |
| 9,854,975 B2 | 1/2018 | Van Pieterson et al. |
| 9,990,472 B2 | 6/2018 | Gurcan et al. |
| 10,016,164 B2 | 7/2018 | Evans et al. |
| 10,080,524 B1 | 9/2018 | Xi |
| 10,085,643 B2 | 10/2018 | Bandic et al. |
| 10,117,617 B2 | 11/2018 | Cantu et al. |
| 10,119,208 B2 | 11/2018 | McMaster |
| 10,178,946 B2 | 1/2019 | Weiss et al. |
| 10,206,604 B2 | 2/2019 | Bergelin et al. |
| 10,226,552 B2 | 3/2019 | Slepian |
| 10,240,265 B2 | 3/2019 | McMaster |
| 10,265,219 B2 | 4/2019 | Duesterhoft et al. |
| 10,285,617 B2 | 5/2019 | Toth et al. |
| 10,292,263 B2 | 5/2019 | Rogers et al. |
| 10,314,537 B2 | 6/2019 | Zegarelli |
| 10,357,201 B2 | 7/2019 | Rogers et al. |
| 10,463,293 B2 | 11/2019 | Maharbiz et al. |
| 10,542,929 B2 | 1/2020 | Kimmel |
| 10,563,795 B2 | 2/2020 | Staton et al. |
| 10,588,723 B2 | 3/2020 | Falkel |
| 10,617,300 B2 | 4/2020 | Rogers et al. |
| 10,631,626 B2 | 4/2020 | Lee et al. |
| 10,674,957 B2 | 6/2020 | Suri et al. |
| 10,702,153 B2 | 7/2020 | Shamim et al. |
| 10,702,205 B2 | 7/2020 | Sharman et al. |
| 10,722,174 B2 | 7/2020 | Pang et al. |
| 10,736,551 B2 | 8/2020 | Rogers |
| 10,736,805 B2 | 8/2020 | Johnson et al. |
| 10,743,973 B2 | 8/2020 | Adams et al. |
| 10,786,395 B1 | 9/2020 | Temkin et al. |
| 10,791,984 B2 | 10/2020 | Kantrowitz et al. |
| 2004/0100376 A1 | 5/2004 | Lye et al. |
| 2004/0186359 A1 | 9/2004 | Beaudoin et al. |
| 2005/0186245 A1 | 8/2005 | Hunter et al. |
| 2006/0047218 A1 | 3/2006 | Bloom et al. |
| 2006/0058593 A1 | 3/2006 | Drinan et al. |
| 2007/0233208 A1 | 10/2007 | Kurtz et al. |
| 2008/0118886 A1 | 5/2008 | Liang et al. |
| 2009/0204100 A1 | 8/2009 | Van Pieterson et al. |
| 2009/0227924 A1 | 9/2009 | Conrad et al. |
| 2010/0004506 A1 | 1/2010 | Saadat |
| 2011/0178375 A1 | 7/2011 | Forster |
| 2012/0116485 A1 | 5/2012 | Burgmann |
| 2012/0209088 A1 | 8/2012 | Romem |
| 2013/0200268 A1 | 8/2013 | Rafferty et al. |
| 2013/0216971 A1 | 8/2013 | Friddell |
| 2013/0245546 A1 | 9/2013 | Hayn |
| 2013/0261409 A1 | 10/2013 | Pathak et al. |
| 2014/0316235 A1 | 10/2014 | Davis et al. |
| 2015/0164372 A1 | 6/2015 | Navab et al. |
| 2015/0250393 A1 | 9/2015 | Tran |
| 2015/0265182 A1 | 9/2015 | Jain et al. |
| 2016/0002223 A1 | 1/2016 | Chekal et al. |
| 2016/0015962 A1 | 1/2016 | Maragheh et al. |
| 2016/0113495 A1 | 4/2016 | Nanjundappa et al. |
| 2016/0135925 A1 | 5/2016 | Mason et al. |
| 2016/0192842 A1 | 7/2016 | Inagaki |
| 2016/0206242 A1 | 7/2016 | Esposito et al. |
| 2016/0228049 A1 | 8/2016 | Nackaerts et al. |
| 2016/0367188 A1 | 12/2016 | Malik et al. |
| 2017/0020402 A1 | 1/2017 | Rogers et al. |
| 2017/0076446 A1 | 3/2017 | Pedersen et al. |
| 2017/0136180 A1 | 5/2017 | Zhao et al. |
| 2017/0181659 A1 | 6/2017 | Rafferty et al. |
| 2017/0181825 A1 | 6/2017 | Hunter |
| 2017/0188864 A1 | 7/2017 | Drury |
| 2017/0202711 A1* | 7/2017 | Cernasov .......... A61F 13/00021 |
| 2017/0216617 A1 | 8/2017 | Kariguddaiah |
| 2017/0224251 A1 | 8/2017 | Ahmad et al. |
| 2017/0224280 A1 | 8/2017 | Bozkurt et al. |
| 2017/0246473 A1 | 8/2017 | Marinkovich et al. |
| 2017/0281073 A1 | 10/2017 | Drennan et al. |
| 2017/0340221 A1 | 11/2017 | Cronin et al. |
| 2017/0340254 A1 | 11/2017 | Davis et al. |
| 2017/0347940 A1 | 12/2017 | Carr et al. |
| 2018/0021178 A1* | 1/2018 | Locke .................. A61F 13/022 602/43 |
| 2018/0036177 A1 | 2/2018 | Anderson et al. |
| 2018/0161211 A1 | 6/2018 | Beckey |
| 2018/0228436 A1 | 8/2018 | Sonkusale et al. |
| 2018/0242894 A1 | 8/2018 | Brauker et al. |
| 2018/0267012 A1 | 9/2018 | Scherer |
| 2018/0317794 A1 | 11/2018 | Mackellar et al. |
| 2018/0333107 A1 | 11/2018 | Sada et al. |
| 2018/0360665 A1 | 12/2018 | Melone |
| 2019/0008694 A1 | 1/2019 | Piotrowski et al. |
| 2019/0021911 A1 | 1/2019 | Askem et al. |
| 2019/0029572 A1 | 1/2019 | Wisniewski et al. |
| 2019/0038214 A1 | 2/2019 | Mikhail et al. |
| 2019/0060126 A1 | 2/2019 | Ribble et al. |
| 2019/0076298 A1 | 3/2019 | Quintanar et al. |
| 2019/0076669 A1 | 3/2019 | Alvarez et al. |
| 2019/0082242 A1 | 3/2019 | Duesterhoft et al. |
| 2019/0137436 A1 | 5/2019 | Lillehoj et al. |
| 2019/0139632 A1 | 5/2019 | Adams et al. |
| 2019/0166285 A1 | 5/2019 | Mistry et al. |
| 2019/0167115 A1 | 6/2019 | Dorodvand et al. |
| 2019/0175104 A1 | 6/2019 | Malik |
| 2019/0216350 A1 | 7/2019 | Sullivan et al. |
| 2019/0223751 A1 | 7/2019 | Weinstein et al. |
| 2019/0264049 A1 | 8/2019 | Atashbar et al. |

(56) References Cited

U.S. PATENT DOCUMENTS

| | | |
|---|---|---|
| 2019/0290496 A1 | 9/2019 | Brownhill et al. |
| 2019/0298263 A1 | 10/2019 | Clasbrummel |
| 2019/0328234 A1 | 10/2019 | Seibel et al. |
| 2019/0328315 A1 | 10/2019 | LaBelle et al. |
| 2019/0333627 A1 | 10/2019 | Johnson |
| 2019/0336077 A1 | 11/2019 | Kuhn et al. |
| 2019/0343397 A1 | 11/2019 | Meisal |
| 2019/0361917 A1 | 11/2019 | Tran et al. |
| 2019/0365571 A1 | 12/2019 | O'Mahony et al. |
| 2019/0374163 A1 | 12/2019 | Faarbaek et al. |
| 2019/0388667 A1 | 12/2019 | Xu |
| 2020/0008299 A1 | 1/2020 | Tran et al. |
| 2020/0020165 A1 | 1/2020 | Tran et al. |
| 2020/0054218 A1 | 2/2020 | Xi |
| 2020/0061379 A1 | 2/2020 | Bogie et al. |
| 2020/0069242 A1 | 3/2020 | Burns et al. |
| 2020/0069280 A1 | 3/2020 | Behzadi et al. |
| 2020/0069409 A1 | 3/2020 | Klueh et al. |
| 2020/0093571 A1 | 3/2020 | Shanjani et al. |
| 2020/0100019 A1 | 3/2020 | Wagner et al. |
| 2020/0100711 A1 | 4/2020 | Choudhury et al. |
| 2020/0105422 A1 | 4/2020 | Ribble et al. |
| 2020/0107772 A1 | 4/2020 | Hu |
| 2020/0121428 A1 | 4/2020 | Pai et al. |
| 2020/0129085 A1 | 4/2020 | Reuel et al. |
| 2020/0138361 A1 | 5/2020 | Amiot et al. |
| 2020/0169722 A1 | 5/2020 | Fisker et al. |
| 2020/0179089 A1 | 6/2020 | Serval et al. |
| 2020/0188180 A1 | 6/2020 | Akbari et al. |
| 2020/0214566 A1 | 7/2020 | Allen et al. |
| 2020/0214637 A1 | 7/2020 | Brownhill et al. |
| 2020/0214817 A1 | 7/2020 | Shanjani et al. |
| 2020/0222597 A1 | 7/2020 | Askem et al. |
| 2020/0237218 A1 | 7/2020 | Irazoqui et al. |
| 2020/0253786 A1 | 8/2020 | Harrison et al. |
| 2020/0253787 A1 | 8/2020 | Hoglund et al. |
| 2020/0260066 A1 | 8/2020 | Liu |
| 2020/0261629 A1 | 8/2020 | Hunt et al. |
| 2020/0280680 A1 | 9/2020 | Nichols |
| 2020/0281480 A1 | 9/2020 | Tran |
| 2020/0281512 A1 | 9/2020 | Grubb et al. |
| 2020/0281529 A1 | 9/2020 | Grubb et al. |
| 2020/0289329 A1 | 9/2020 | Cole et al. |
| 2020/0289347 A1 | 9/2020 | Gowans et al. |
| 2020/0297244 A1 | 9/2020 | Brownhill et al. |
| 2020/0297255 A1 | 9/2020 | Martinez et al. |
| 2020/0312453 A1 | 10/2020 | Räisänen et al. |
| 2020/0315488 A1 | 10/2020 | Rogers et al. |
| 2020/0334813 A1 | 10/2020 | Salah et al. |
| 2021/0145359 A1 | 5/2021 | Hunt |
| 2021/0169417 A1 | 6/2021 | Burton |
| 2022/0215545 A1* | 7/2022 | Adiri ............... A61B 5/0015 |

* cited by examiner

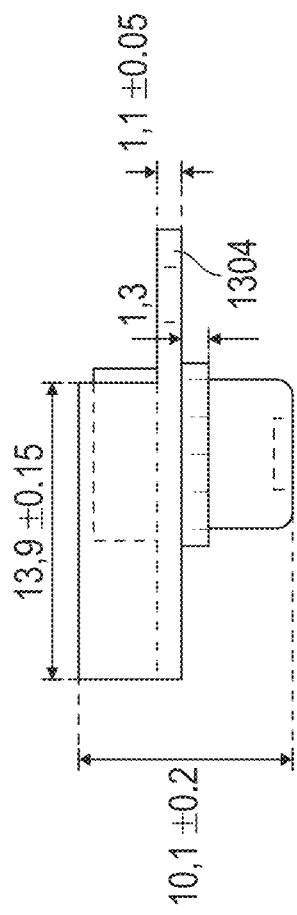
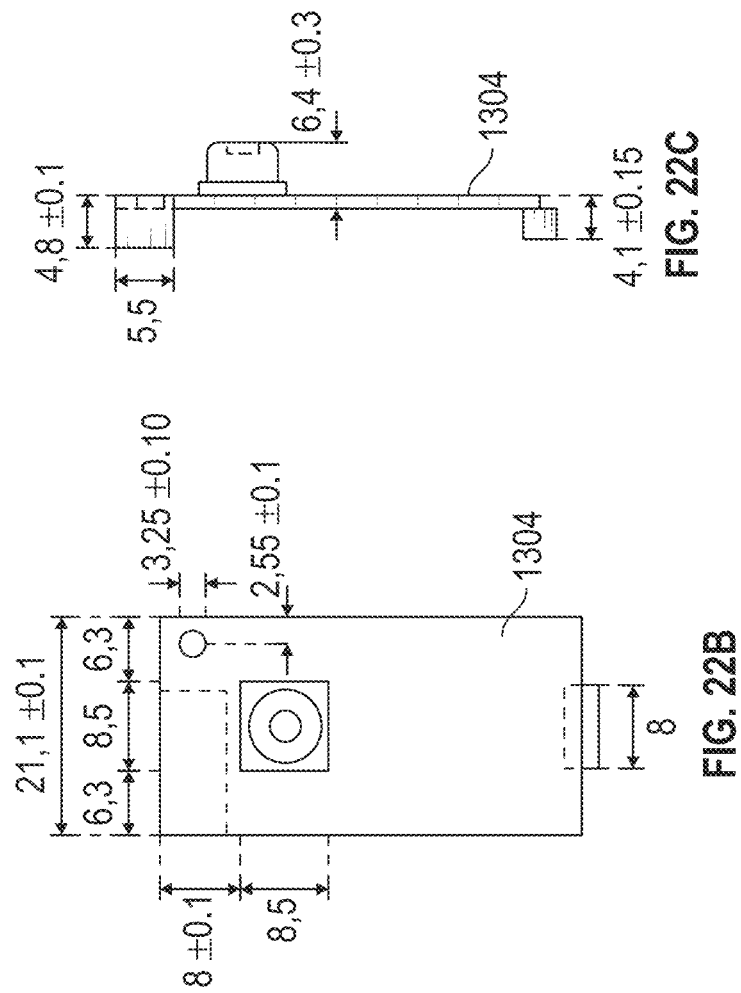
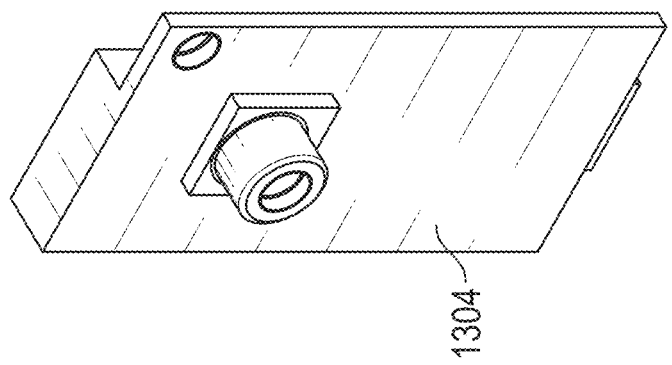
FIG. 22A FIG. 22B FIG. 22C FIG. 22D

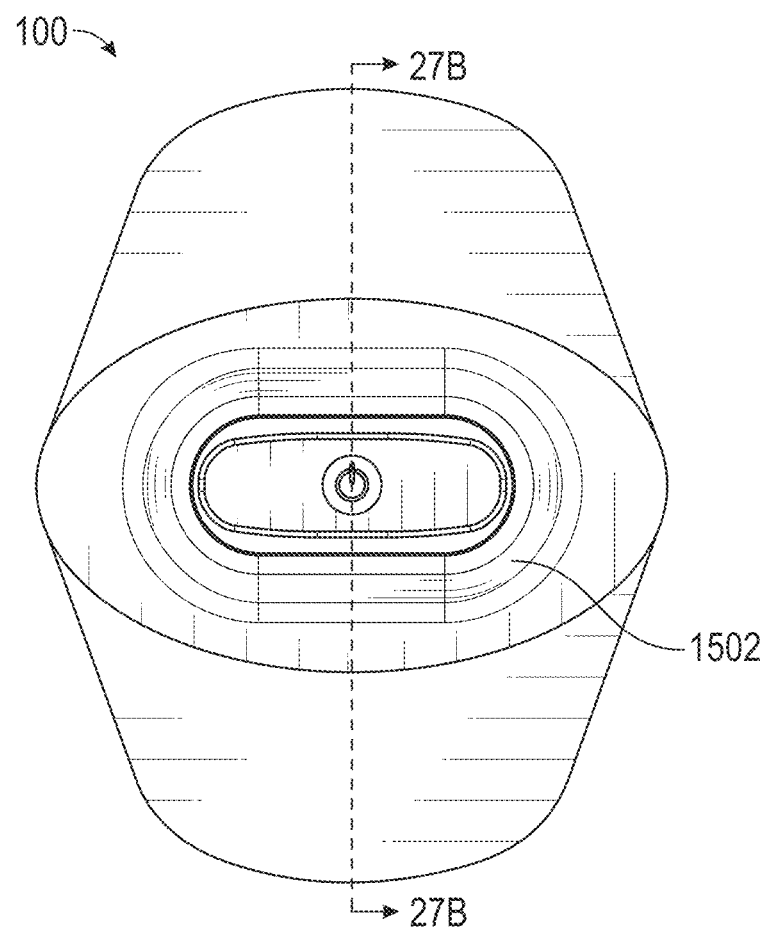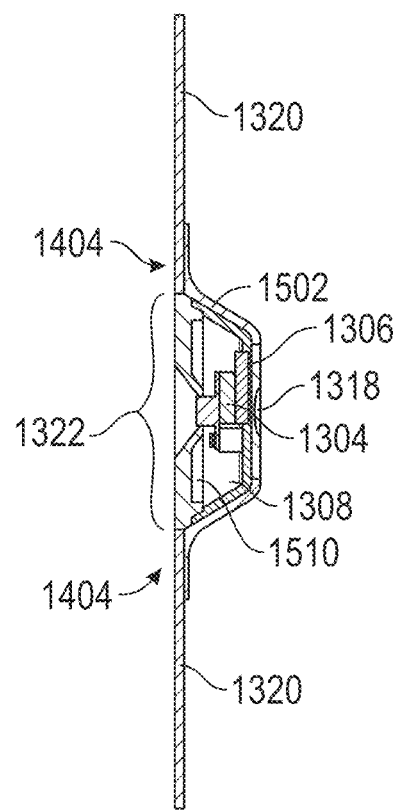
FIG. 27A
FIG. 27B

CONNECTED BODY SURFACE CARE MODULE

CROSS-REFERENCE TO RELATED APPLICATIONS

The present application is a continuation of U.S. patent application Ser. No. 17/806,846, filed on Jun. 14, 2022 and titled "CONNECTED BODY SURFACE CARE MODULE," which claims priority to U.S. Provisional Patent Application No. 63/202,506, filed on Jun. 14, 2021 and titled "CONNECTED BODY SURFACE CARE MODULE," U.S. Provisional Patent Application No. 63/266,392, filed on Jan. 4, 2022 and titled "CONNECTED BODY SURFACE CARE MODULE," and U.S. Provisional Patent Application No. 63/267,475, filed on Feb. 2, 2022 and titled "CONNECTED BODY SURFACE CARE MODULE." Any and all applications for which a foreign or domestic priority claim is identified in the Application Data Sheet, or any correction thereto, are hereby incorporated by reference and made part of this specification under 37 C.F.R. § 1.57.

BACKGROUND

Field

This application relates, in general, to a body care device with a sensor device, and in one arrangement, to a wearable body surface care device with a camera.

Description of the Related Art

There exist various body surface care devices. For example, some devices are used for analysis of skin, such as devices that provide monitoring through imaging and volume measurements.

BRIEF DESCRIPTION OF THE DRAWINGS

Embodiments of various inventive features will now be described with reference to the following drawings. Throughout the drawings, reference numbers may be re-used to indicate correspondence between referenced elements. The drawings are provided to illustrate example embodiments described herein and are not intended to limit the scope of the disclosure.

FIG. 22A is a perspective view of the PCB from FIG. 13A.

FIG. 22B is a front plan view of the PCB from FIG. 13A.

FIG. 22C is a side view of the PCB from FIG. 22B.

FIG. 22D is an upper plan view of the PCB from FIG. 13A.

FIG. 27A is a top plan view of another embodiment of the treatment and analysis module that is similar to the module of FIG. 23A except the one or more legs extend from the housing at a location below the platform.

FIG. 27B is a cross-section view through the module in FIG. 27A showing the one or more legs in the extended configuration.

DETAILED DESCRIPTION OF ILLUSTRATIVE EMBODIMENTS

Figure 1:
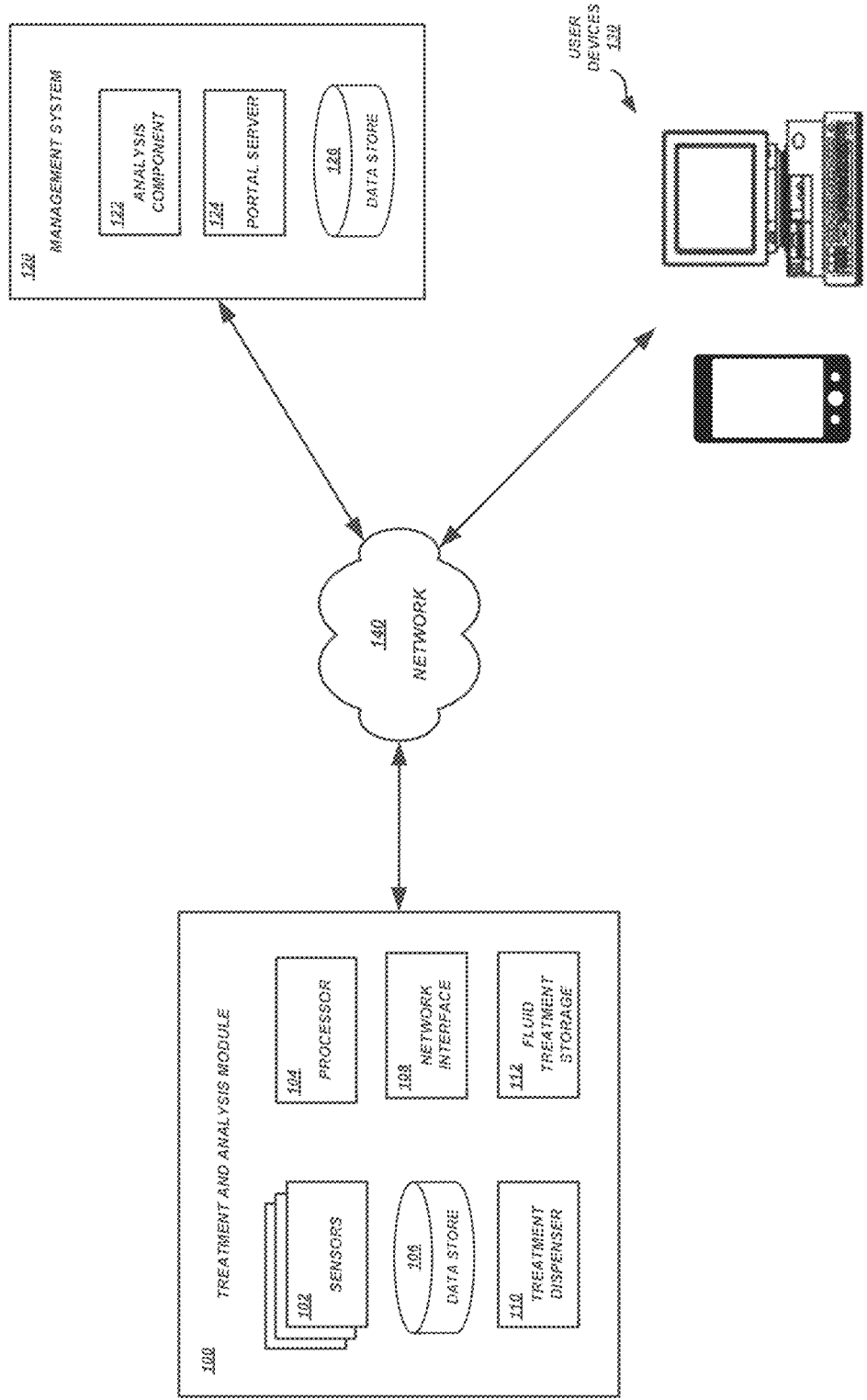
FIG. 1 is a diagram of a network environment including a treatment and analysis module, a management system, and one or more user devices according to some embodiments.

The present disclosure is directed to a wearable treatment and analysis module that is positioned on or near a body surface region of interest. The module provides remote access to sensor data, treatment administration, and/or other health care regimens via a network connection with a user device and/or management system.

Some conventional systems use sensors to measure aspects of body surface regions. Other conventional systems facilitate administration of treatment to body surfaces. However, such systems may not be remotely accessible and/or controllable. Moreover, use of wearable medical articles such as bandages, casts, and the like may inhibit use of such sensor systems and treatment systems.

Some aspects of the present disclosure address one or more of the issues noted above, among others, by providing a treatment and analysis module configured to be mounted to a bandage, wrap, cast, or other wearable medical article and positioned in proximity to a body surface region of interest, such as a wound (e.g., from an injury, disease, or surgery). The treatment and analysis module is remotely accessible to facilitate access to sensor data, treatment instructions, and the like. Thus, the treatment and analysis module aids health care professionals in monitoring and managing the treatment for post-surgical patients or patients with wounds or other skin conditions without removing the bandage, wrap, or cast. The remote monitoring and treatment management provided by the treatment and analysis module also allows for accelerated patient discharge from medical facilities.

Additional aspects of the present disclosure provide automated analysis of sensor data to detect body surface conditions. In some embodiments, machine learning models may be trained and used to detect body surface conditions (e.g., wounds, diseases, etc.), to determine the severity of the conditions, and/or to evaluate the change in the body surface conditions over time. For example, image analysis models may be used to classify images as depicting various body surface conditions. As another example, scoring models may be used to grade the degree and/or severity of the body surface conditions. In some embodiments, different machine learning models may be trained and targeted for use in classifying or otherwise evaluating different types of wounds, such as wounds from different types of injuries and/or surgeries. For example, sensor data from a particular treatment and analysis module regarding a particular type of wound may be evaluated using one machine learning model or set of models, while sensor data from a different treatment and analysis module regarding a different type of wound may be evaluated using a different machine learning model or set of models.

Further aspects of the present disclosure provide wearable medical articles and/or treatment and analysis modules configured for particular types of wounds or other applications. In some embodiments, a treatment and analysis module configured for a particular type of wound may include a particular set of one or more sensors that provide data that is advantageous in monitoring and/or treating the particular type of wound. A treatment and analysis module configured for a different type of wound may include a different set of sensors that provide data advantageous in monitoring and/or treating the different type of wound. The sets of sensors may be different such that one set of sensors may include additional, fewer, and/or alterative sensors or sensor configurations than the other set of sensors. Differences between different wearable medical articles and/or treatment and analysis modules are not necessarily limited to different sensor configurations. In some embodiments, a wearable medical article and/or treatment and analysis module may be sized and/or shaped to target or be suitable for a particular type of wound. In some embodiments, a wearable medical article and/or treatment and analysis module may be sized, shaped, or otherwise configured for robotic placement. For example, a treatment and analysis module may include features such as structural registration points, alignment aids, or the like to facilitate being held, manipulated, and placed by a medical robot onto or near a wound.

Various aspects of the disclosure will now be described with regard to certain examples and embodiments, which are intended to illustrate but not limit the disclosure. Although the examples and embodiments described herein will focus, for the purpose of illustration, on specific devices, data, treatments, and algorithms, one of skill in the art will appreciate the examples are illustrative only, and are not intended to be limiting, essential, or exhaustive. In addition, any feature, process, device, or component of any embodiment described and/or illustrated in this specification can be used by itself, or with or instead of any other feature, process, device, or component of any other embodiment described and/or illustrated in this specification.

Example Network Environment for Remote Access to Treatment and Analysis Module FIG. 1 shows a network environment including a treatment and analysis module 100, a management system 120, and one or more user devices 130. The individual devices may communicate via one or more communication networks 140.

A communication network 140—also referred to simply as a "network"—may be a publicly accessible network of linked networks, possibly operated by various distinct parties, such as the internet. In other embodiments, a network 140 may include a private network, personal area network, local area network, wide area network, cable network, satellite network, cellular telephone network, etc. or a combination thereof, some or all of which may or may not have access to and/or from the internet.

The treatment and analysis module 100 may be, or be part of, a personal care system. The treatment and analysis module 100 may include various modules, components, and data stores to implement monitoring of characteristics of a user tissue or other body surface region (e.g., epidermis, oral mucosa, dental enamel, etc.), application of treatments (e.g., topical fluids, ozone, ultraviolet light, negative pressure wound therapy, etc.), and communication of monitoring and treatment information to and/or from other devices and systems, such as the management system 120 and/or user devices 130.

The treatment and analysis module 100 may include one or more sensors 102 to monitor and generate data regarding user skin characteristics. In some embodiments, the one or more sensors 102 may include a visualization element, such as a camera sensor, to capture images and/or generate other visualization data regarding the skin of a user. Such visualization data may be used to monitor a wound or other skin aspect over time, to diagnose a skin condition, to determine a treatment for a skin condition, and/or to monitor the treatment of a skin condition over time. In some embodiments, the one or more sensors 102 may also or alternatively include a temperature sensor to determine the temperature of the user's body surface region and/or the ambient temperature. In some embodiments, the one or more sensors 102 may also or alternatively include an accelerometer to assess movements and activities of the patient. In some embodiments, the one or more sensors 102 may also or alternatively include a pH sensor to determine the pH level of the user's body surface region. In some embodiments, the one or more sensors 102 may also or alternatively include a moisture sensor to determine the moisture content of the user's body surface region and/or the ambient moisture around a location of the user's body surface region. In some embodiments, the one or more sensors 102 may also or alternatively include a pressure sensor to determine the pressure, such as pressure within a cast, bandage, or other enclosure to which the treatment and analysis module 100 is mounted. The example sensors 102 described herein are illustrative only, and are not intended to be limiting, required, or exhaustive of the sensors 102 that may be included in a treatment and analysis module 100. In some embodiments, one treatment and analysis module 100 may be configured for use with a particular type of suture site or other wound, and may include a particular set of one or more sensors 102 that provide data that is advantageous in monitoring and/or treating the particular type of wound. Another treatment and analysis module configured for a different type of suture site or other wound may include a different set of sensors (e.g., additional, fewer, and/or alterative sensors or sensor configurations).

The treatment and analysis module 100 may include a processor 104, such as a system on a chip ("SOC") or other microprocessor to process data and commands. In some embodiments, the processor 104 may process data from one or more sensors 102 and/or the data store 106, execute one or more analysis or detection algorithms, receive and execute commands from other devices via a network interface 108, or the like. In some embodiments, the data store 106 may be a substantially persistent data store, such as flash memory, hard disk, or the like. The network interface 108 may be a wired or wireless network interface, such as a network adapter card and/or a wireless antenna (e.g., a Wi-Fi antenna, a Bluetooth® antenna, etc.).

The treatment and analysis module 100 may include components to store and administer treatment to the body surface region of a user. For example, treatment may be a topical fluid, such as a spray, lotion, ointment, or gas. The fluid treatment may be stored in a fluid treatment storage 112, and dispensation of the fluid treatment may be performed using a treatment dispenser 110. In some embodiments, the fluid treatment storage 112 may be a fluid-tight container in fluid communication with the treatment dispenser 110. The treatment dispenser 110 may include an aperture through which fluid from the fluid treatment storage 112 can be dispensed onto a body surface region of a user. In some embodiments, the treatment dispenser 110 may include or be controlled by a mechanical actuator to actively expel fluid treatment (e.g., to urge fluid from a nozzle) or to permit the release of pressurized fluid treatment (e.g., to open a valve to allow fluid to pass). As another example, treatment may include waveform-based treatments, such as ultraviolet light or ultrasound. The treatment dispenser 110 for such treatments may include corresponding emission devices, such as ultraviolet light emitting diodes ("LEDs") and/or ultrasonic transducers.

In some embodiments, the treatment and analysis module 100 may be a removable component of a home-use hand-held personal care device such as, for example, a facial beauty device or hair apparatus. With reference to an illustrative embodiment of such a home-use hand-held personal care device (disclosed in U.S. Patent Application Publication No. 2020/0280680, which is incorporated by reference herein and forms part of this disclosure), the personal care device may include a platform that allows for application of a various modules. The platform may be adapted to incorporate aspects of the present disclosure, such as permitting application of the treatment and analysis module 100 instead of, or in addition to, a separate camera, and/or a second treatment dispenser for other treatments (e.g., a brush, an energy-delivery applicator, etc.). A user can attach a module to the personal care device at the platform, analyze and/or treat skin or other body surface region with the personal care device using the attached module, remove the module from the platform, attach a second module at the platform, etc. In some embodiments, the treatment and analysis module 100 may be configured for permanent or semi-permanent incorporation within an exterior housing of personal care devices. For example, the sensor(s) 102, processor 104, data store 106, and/or network interface 108 may be integrated into or coupled to a circuit board. In this configuration, the circuit board assembly and other components of the module 100 may be installed within the housing of a personal care device, such as a negative pressure wound therapy device, optical coherence tomography device, or micro-elastography device.

In some embodiments, the treatment and analysis module 100 may be a removable component of a personal wound care device, such as a bandage or cast. The treatment and analysis module 100 may be removably integrated with, mounted to, or otherwise attached to the personal wound care device and positioned on or near a region of interest, such as a suture site or other wound. The position may be selected to facilitate visualization of the region of interest (e.g., via a camera sensor), monitor other aspects of the region of interest (e.g., via other sensors such as a temperature and/or moisture sensor), and/or apply fluid treatment to the region of interest. Examples of personal wound care devices are described below.

In some embodiments, treatment and analysis module 100 (or a wearable medical article to which the treatment and analysis module 100 is coupled) may be sized and/or shaped to target a particular type of wound. For example, one or more dimensions (e.g., length, width, height) of the treatment and analysis module 100 may be configured based on one or more dimensions of, or the severity or type of wound present on, the body surface region on which the treatment and analysis module 100 is to be placed. In some embodiments, a treatment and analysis module 100 may be sized, shaped, or otherwise configured for robotic placement. For example, a treatment and analysis module 100 may include features such as structural registration points, alignment aids, or the like to facilitate being held, manipulated, and placed by a robotic surgical system onto a body surface region.

Figure 2:
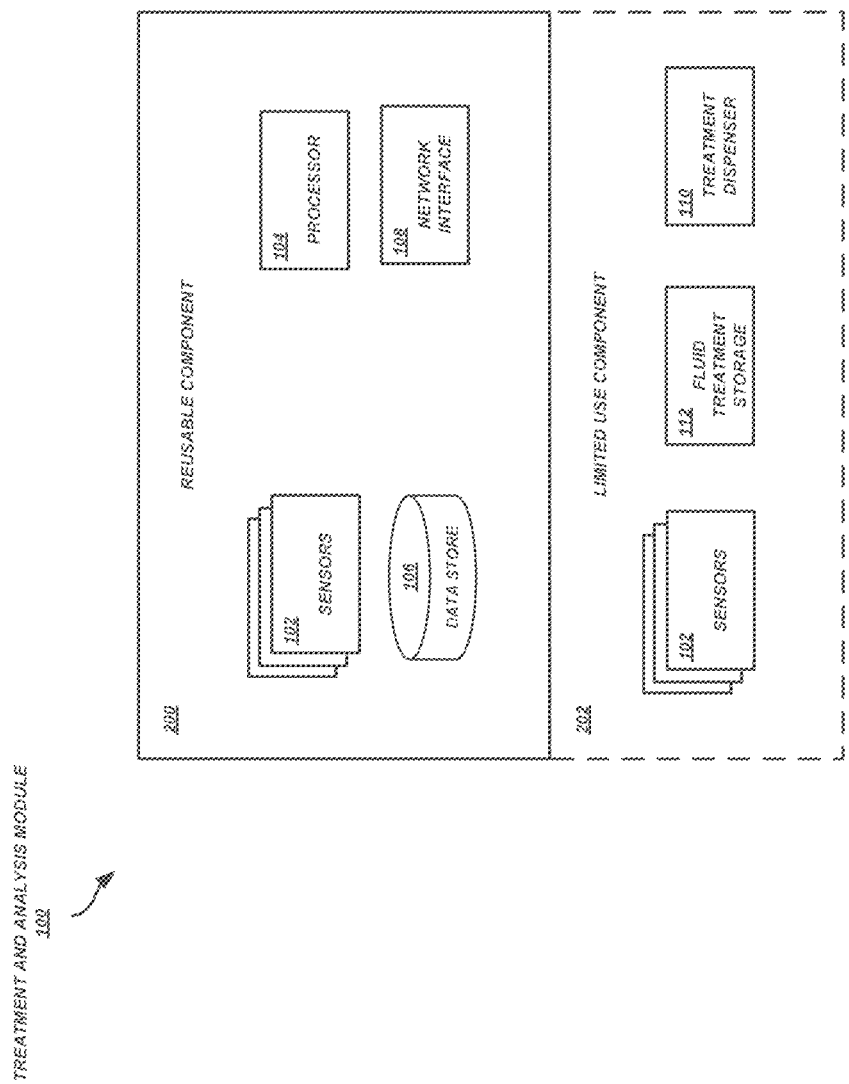
FIG. 2 is a diagram of a treatment and analysis module with a reusable component and a limited use component according to some embodiments.

In some embodiments, the treatment and analysis module 100 or components thereof may be designed for a single use or otherwise for a limited quantity or duration of use. For example, if portions of the treatment and analysis module 100 come into physical content with a region of a user's body surface (e.g., a wound, dental enamel, or oral mucosa), the treatment and analysis module 100 as a whole may be limited use. As another example, components of the portions of the treatment and analysis module 100 that contact the body surface region may be limited use, while other portions of the treatment and analysis module may be reusable. As a further example, portions of the treatment and analysis module 100, such as the fluid treatment storage 112, may include exhaustible resources. Such portions may be refillable or replaceable. Examples and details of limited-use treatment and analysis modules 100 or components thereof are shown in FIG. 2 and described in greater detail below.

The management system 120 may include various components for providing the features described herein. Illustratively, the management system 120 may include an analysis component 122 to process data received from the treatment and analysis module 100 (e.g., sensor data, treatment data, etc.), determine treatment instructions, and the like. The management system 120 may also include a portal server 124 that may be configured to provide access to results generated by the analysis component 122, receive instructions or other input regarding the analysis or treatments, and the like. The management system 120 may also include a data store 126 that maintains data regarding treatments, results, users, and the like. The example components and data stores of the management system 120 shown in FIG. 1 are illustrative only, and are not intended to be limiting, required, or exhaustive. In some embodiments, a management system 120 may have fewer, additional, and/or alternative components and data stores.

The management system 120 may be implemented on one or more physical server computing devices that provide computing services and resources to treatment and analysis modules 100 and user devices 130. In some embodiments, the management system 120 (or individual components thereof, such as the analysis component 122, portal server 124, data store 126, etc.) may be implemented on one or more host devices, such as blade servers, midrange computing devices, mainframe computers, desktop computers, or any other computing device configured to provide computing services and resources. For example, a single host device may execute one or more analysis components 122, one or more portal servers 124, one or more data stores 126, some combination thereof, etc. The management system 120 may include any number of such hosts.

In some embodiments, the features and services provided by the management system 120 may be implemented as web services consumable via communication network 140. In further embodiments, the management system 120 (or individual components thereof) is provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

The individual user devices 130 may be any of a wide variety of computing devices, including personal computing devices, terminal computing devices, laptop computing devices, tablet computing devices, electronic reader devices, wearable computing devices, mobile devices (e.g., smart phones, media players, handheld gaming devices, etc.), and various other electronic devices and appliances. A user device 130 may be used to access data generated by a treatment and analysis module 100 or management system 120, to provide data and/or instructions to a treatment and analysis module 100 or management system 120, etc.

The treatment and analysis module 100, also referred to herein as a "wearable module" or "module," can be controlled or monitored by application software executing on a user device 130. In some embodiments, an individual who is wearing or operating a treatment and analysis module 100 (e.g., as part of a hand-held personal care device or a personal wound care device) may use a user device 130 to interact with the treatment and analysis module 100. In some embodiments, an individual who is remotely managing or operating a treatment and analysis module 100 (e.g., a health care professional monitoring and managing the care of a patient wearing a personal wound care device or operating a hand-held personal care device) may use a user device 130 to interact with the treatment and analysis module 100 and/or the management system 120. In some embodiments, application software to interact with the treatment and analysis module 100 and/or management system 120 may be provided to the user device 130 over a network connection. For example, a user may enter a code or scan an encoded image (e.g., a barcode, quick response or "QR" code, or the like) and be directed to a network resource (e.g., a server on the internet or an intranet) from which the application software may be downloaded. As another example, a user may manually access a network resource and download the application software.

With reference to an illustrative embodiment, the treatment and analysis module 100 may include an application programming interface ("API"). The API can be implemented within or called by the user device 130 using the software application. It will be appreciated that the module 100, user device 130, and/or management system 120 may communicate with each other via the network 140 using specialized API calls that enable one of the modules, devices, or systems to request that another module, device, or system generate responsive data to be returned via an API response. It will be further appreciated that particular aspects or functionality of the API described herein may be implemented at different modules, devices, or systems illustrated in FIG. 1. For example, the user device 130 may implement aspects of the API related to generating user interfaces that display images captured by the module 100, while a management system 120 may implement aspects of the API that employ one or more machine learning models to analyze images provided to the management system 120 by the module 100 or user device 130. The particular module, device, or system that implements particular functionality described herein, such as functionality or features described herein as being provided by the API, may depend on the processing capabilities of the given device in the given embodiment. For example, a user device 130 may be configured to execute image analysis locally or to request that such image analysis be performed remotely at the management system 120, depending on the configuration of the management system 120, or on the processing capabilities of a particular user device 130 (e.g., desktop computer, mobile phone) on which the application is operating.

In some embodiments, an API and/or application software executing on one or more of the module 100, management system 120, or user device 130 can provide any or all of following functionalities: power on or off the module 100; take before and after images via a camera sensor of the module 100; instruct the user through the user device 130 on how to perform functions of the module 100 (e.g., take images, store or access image files, schedule treatment regimens); display images on the user device 130, singularly or side-by-side, captured by a camera sensor of the module 100; calculate and monitor measurements of aspects of a region of a user's body surface (e.g., wound area, wound volume, lesion area, lesion volume, wrinkle depth, fine line frequency, epidermal layer exfoliation, skin hydration) based on data provided by one or more sensors of the module 100; and/or provide detailed images to the management system 120 or another user device 130 for evaluation.

The management system 120 and/or user device 130 can process images from a camera of the module 100. In some arrangements, an API can be used for capturing an image with a camera sensor 102. The camera sensor 102 can use the API to provide image data via Wi-Fi or Bluetooth to the management system 120, a user device 130, other devices, or some combination thereof. For example, application software executing on a user device 130 can allow a user to program or control the operation of the module 100 via an API. The module 100 can provide for acquisition of a digital image of a region of a user's body surface at an increased magnification, such as at a magnification of about: 2×, 10×, 50×, 400×, and various intermediate values. In some embodiments, as described in greater detail below with respect to FIG. 3, the module 100 includes a camera sensor with zoom-in functionality that increases the magnification of the camera.

In some embodiments, the module 100 includes a holographic high-resolution camera sensor configured to provide non-line-of-sight ("NLoS") imaging. For example, the camera sensor may use synthetic wavelength holography in which light is indirectly scattered onto objects, including objects that may not be imaged using a conventional camera sensor due to being partially or completely obstructed by tissue (e.g., skin, bone, muscle) or other objects. Scattered light captured by a holographic camera sensor may be used to construct an image that exposes partially or completely obscured regions of interest.

In some embodiments, the module 100 includes a three-dimensional wound assessment monitor ("3D-WAM") camera sensor. Advantageously, such a camera sensor is able to measure wound size in three dimensions. A laser, such as a vertical-cavity surface-emitting laser ("VCSEL"), works in the near-infrared spectroscopy ("NIR") range (e.g., 940 nm) to generate 2D and 3D data in one shot with a multipart image, incorporating range, intensity and confidence maps.

The module 100 may generate digital photographs that one or more user devices 130 or the management system 120 can analyze to determine information relating to a condition of the skin, such as, for example, wound size, wound shape, wound depth, wound color, debris in the wound, etc. Storage of images (e.g., in a data store 106 of the module 100 or a data store 126 of the management system 120) can enable presentation of "before-and-after" visual results via a user interface displayed by a user device 130. For example, a user such as a wearer of the module 100 or a health care professional can cause the module 100 to take a "before" image before treating a body surface region, then cause dispensation of treatment to the body surface region via the treatment dispenser 110, and then cause the module to take an "after" image of the body surface region. In this way, the module 100 and remote access to images captured by the module 100 can be used to provide a recovery tracker that allows a user to evaluate a treatment administered to a body surface region. For example, a user can use the module 100 to take a series of images of the body surface region over the course of time (e.g., over days, weeks, months) and compare the images to one another to evaluate whether a treatment regimen applied to the body surface region is effective at improving a condition (e.g., wound healing). In some embodiments, the module 100 can allow a user to watch live digital image and/or video feed on a user device 130.

Example Treatment and Analysis Module

With reference to FIG. 2, illustrative embodiments of a treatment and analysis module 100 will be described. In some embodiments, as shown, a portion of the treatment and analysis module 100 can be implemented as a limited use component 202. For example, the limited use component 202 may be configured to contact or otherwise be exposed an oral surface of a user (e.g., dental enamel, dentin, oral mucosa), a wound of a user, or some other body surface region. Such exposure may be advantageous for the operation of certain components of the treatment and analysis module 100, such as one or more of the sensors 102 or a treatment dispenser 110. By implementing such components as (or as a part of) a limited use component 202, contamination via exposure to a region of a user's body surface can be minimized through limited use of the content(s). As another example, the limited use component 202 may be or include a reservoir for an exhaustible resource, such as a fluid treatment storage 112. By implementing such components as (or as a part of) a limited use component 202, mechanisms to replenish the exhaustible resource do not need to be incorporated. Rather, the limited use component 202 can be replaced with a new component 202 that has a fresh supply of the exhaustible resource.

The limited use component 202 may be removably attached to a reusable substrate for use. In some embodiments, the treatment and analysis module 100 may include a reusable component 200 to which the limited use component 202 may be removably attached. The reusable component may include additional components of the treatment and analysis module 100 that are not included in the limited use component 202 or that may be alternatives to components of the limited use component 202. For example, the reusable component may include more durable and/or expensive components of the treatment and analysis module 100, such as the processor 104, data store 106, and network interface 108. One or more sensors 102 may also be included, such as those that do not need direct contact or exposure to the body surface region of the user (e.g., a motion sensor, an ambient moisture sensor, an ambient temperature sensor). In some embodiments, one or more sensors 102 that do require exposure to the body surface region of the user may be included in the reusable component 202. For example, a camera sensor may be included in the reusable component 202 due to the expense, complexity, and/or other characteristics of the camera for which limited use and replacement may not be desirable. In these arrangements, the limited use component 202 may include a protected exposure portion, such as a sealed window or filtered aperture, through which the sensor of the reusable component 200 may gain exposure to a body surface region of the user.

In certain arrangements, the reusable component 200 or the treatment and analysis module 100 as a whole can be waterproof or water-resistant, allowing the reusable component 200 or module 100 to be submerged or brought into contact with water without damage. For example, the module 100 can be adapted to allow a user to use the module 100 in a shower or a bathtub. The housing of the module 100 can form a water-tight seal that prevents water from entering the internal space of the module 100, thereby protecting the internal electronics of the module 100 from being contacted by water. The housing of the module 100 can form a water-tight seal with the personal care device to which the module is attached.

Figure 3:
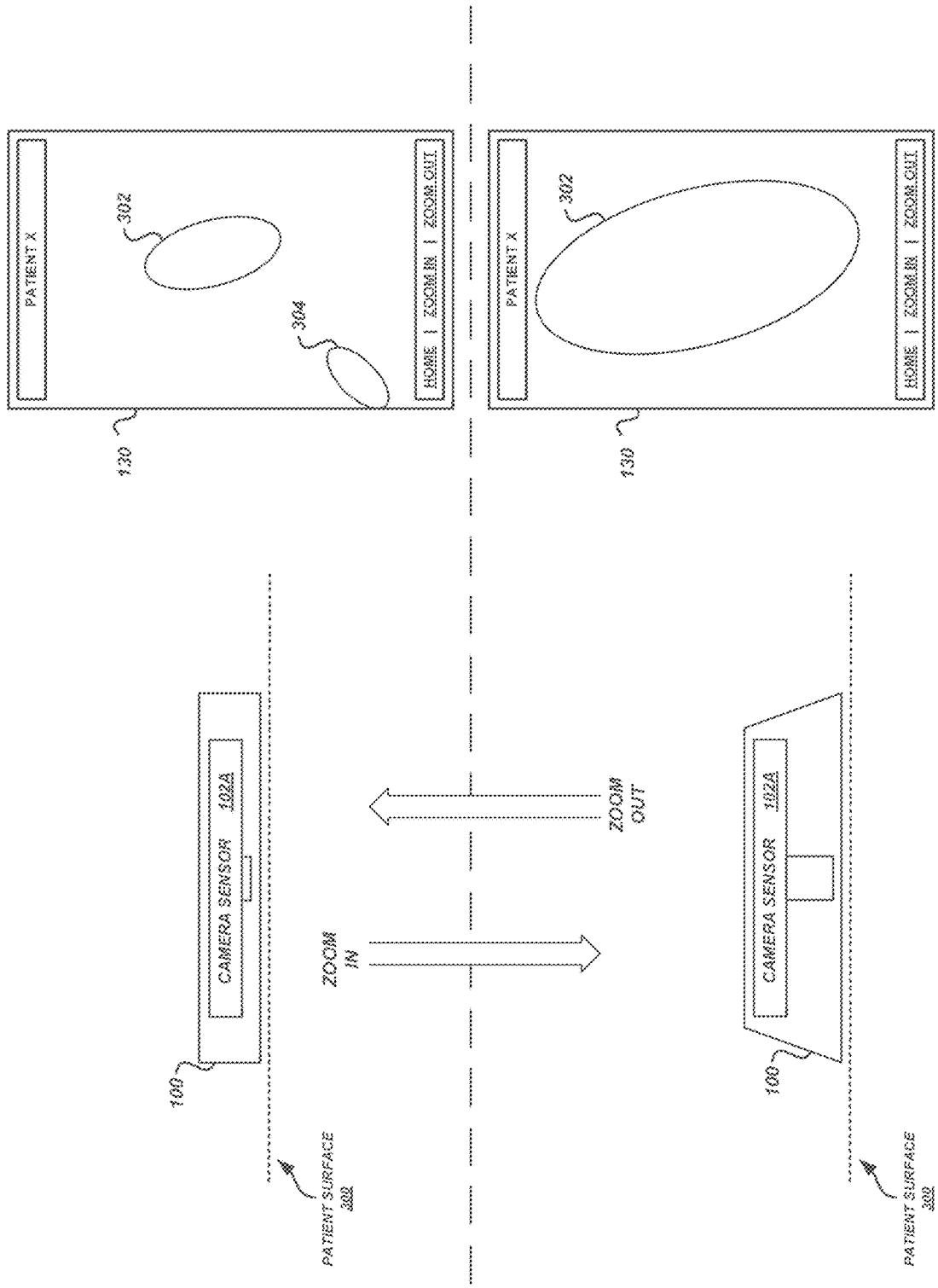
FIG. 3 is a diagram of a treatment and analysis module with a camera sensor configured to move from a low-profile state, in which a first view is obtained for presentation on a user device, to a raised-profile state, in which a second view is obtained for presentation on the user device.

FIG. 3 illustrates a treatment and analysis module 100 with a camera sensor 102A configured to move from a low-profile state to a raised-profile state. In the low-profile state, shown in the upper half of the diagram, a first view of a body surface region 300 is obtained, showing surface portions of interest 302 and 304. In the raised-profile state, shown in the lower half of the diagram, a second view is obtained showing a zoomed-in view of portion of interest 302. In some embodiments, the first view may be a wider-angle view than the second view due to the optical configuration of the camera sensor 102A. For example, the camera sensor 102A may be configured to transition from the low-profile state to the raised profile state in order to zoom in on a particular subregion of the body surface region 300. The transition may be caused by manual application of force (e.g., a user turns a zoom ring, applies pressure, etc.). In some embodiments, the module 100 and/or the camera sensor 102 may include a motorized subsystem for transitioning from the low-profile state to the raised-profile state and vice versa. Images captured in the different states may show wide-angle and zoomed-in views, respectively, on a user device 130.

Example Process for Use and Management of Operation of Module

Figure 4:
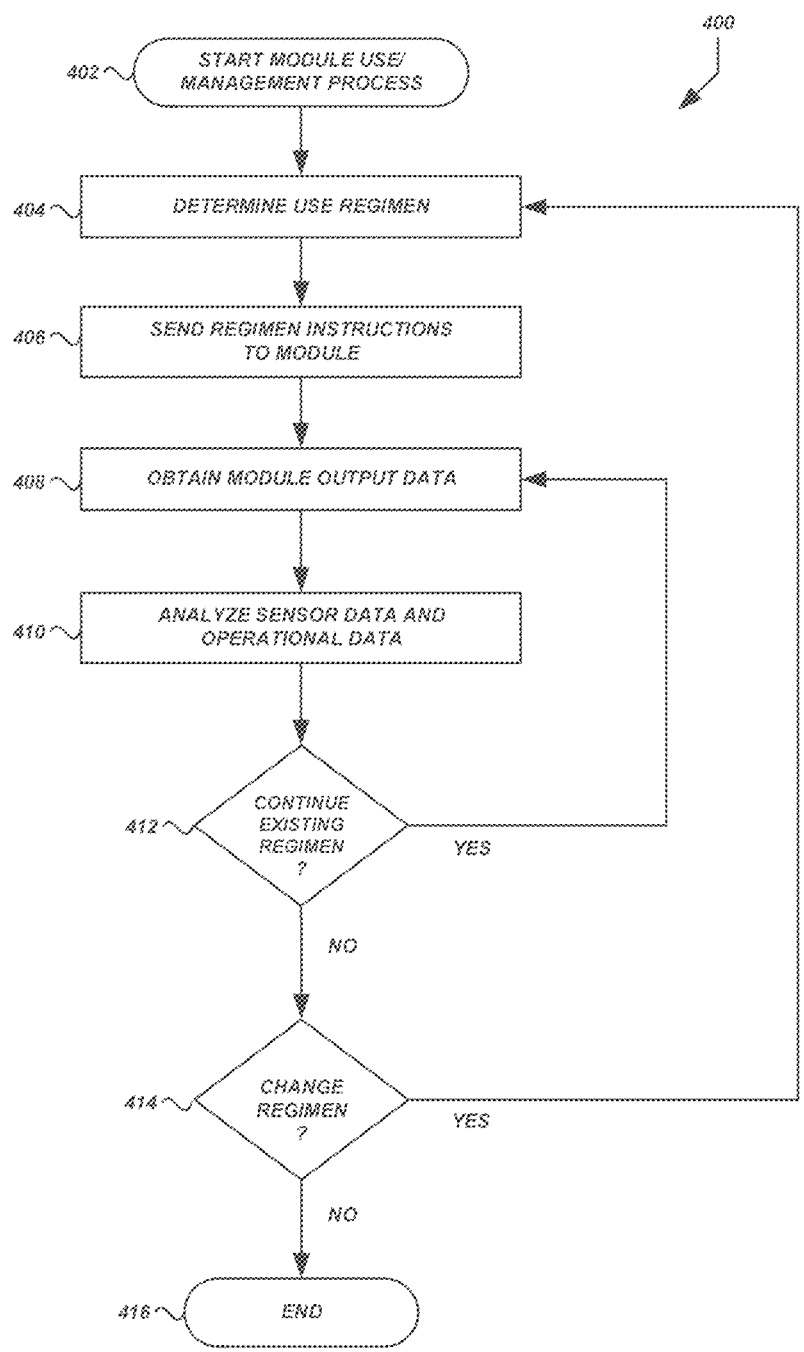
FIG. 4 is a flow diagram of an illustrative process for analyzing treatment and sensor data and implementing regimens according to some embodiments.

FIG. 4 is a flow diagram of an illustrative process 400 that may be executed to use and/or manage the operation of a treatment and analysis module 100. The process 400 or portions thereof may be executed by a user device 130 and/or management system 120, individually or in combination. Advantageously, execution of the process 400 allows for remote access to data generated by a treatment and analysis module 100, and remote control of operations of the treatment and analysis module 100. For example, the process 400 allows for implementation and analysis of a monitoring regimen in which sensor data is generated for analysis. As another example, the process 400 allows for implementation of a treatment regimen in which a treatment is administered to a wearer of the module 100. The wearer of the module 100 may also be referred to as a "subject" of the sensor data generated by and/or treatment administered by the module 100.

Portions of the process 400 will be described with further reference to the illustrative data flows and interactions between the treatment and analysis module 100, management system 120, clinician user device 130A, and patient user device 130B shown in FIG. 5.

The process 400 begins at block 402. The process 400 may begin in response to an event, such as when a clinician device 130A connects to the management system 120 to initiate a regimen for use of the treatment and analysis module 100. In some embodiments, process 400 or portions thereof may be performed on a predetermined or dynamically-determined schedule. For example, output data from the module 100 (images and/or other sensor data) may be obtained periodically, such as hourly, daily, or weekly. The module 100 may be programmed to initiate the capture and/or transfer of the output data, or another system such as the management system 120 or a user device 130 may request the output data from the module 100. In some embodiments, process 400 or portions thereof may be performed on-demand, such as when a user interacts with the module 100, a clinician device 130A, or a patient device 130B. In this way, process 400 may produce real time or substantially real time implementation and analysis. When the process 400 is initiated, a set of executable program instructions stored on one or more non-transitory computer-readable media (e.g., hard drive, flash memory, removable media, etc.) may be loaded into memory (e.g., random access memory or "RAM") of a computing device, such as a computing device of management system 120. In some embodiments, the process 400 or portions thereof may be implemented on multiple processors, serially or in parallel.

At block 404, the system executing the process 400 may determine a regimen for use of the module 100. In one embodiment, a regimen may specify a treatment to be administered by the module 100. For example, the module 100 may be configured to administer a topical fluid, such as a spray, lotion, or ointment. Administration of the treatment may be a one-time on-demand administration, or it may be scheduled for one or more future times according to a predetermined or dynamically determined schedule. In another embodiment, a regimen may specify sensor data to be generated, stored, and/or transmitted to a separate system such as the management system 120 or user device 130. For example, the regimen may specify a set of one or more sensor data items to be generated and transmitted. Generation and transmission of the set of sensor data items may be specified as a one-time on-demand process, or may be scheduled for one or more future times according to a predetermined or dynamically determined schedule.

Determination of the regimen may be based on a selection or other input from a user, such as a wearer of the module 100 or a health care professional. For example, a user device 130 (e.g., a clinician device 130A or a patient device 130B) may present regimen options that can be selected and implemented. A user may activate an option, and the activation may indicate determination of the particular regimen to be implemented.

In some embodiments, the regimen may be automatically generated or suggested using a recommendation algorithm. The recommendation algorithm may take input, such as information regarding the subject (e.g., demographic information, information regarding the current state of the user's body surface region being monitored and/or treated, etc.) and/or information regarding treatments used by the subject.

For example, the recommendation algorithm may be a collaborative filtering algorithm, a content-based filtering algorithm, or a combination of algorithms.

In a collaborative filtering implementation, a model may be trained to generate recommendations of treatments or other regimens that were effective for similar subjects. The model may be used to evaluate information about the subject, such as features derived from the subject's demographic information and/or information regarding the current state of the user's body surface region being treated. The model may then output a recommendation of a treatment or other regimen that was effective for other subjects with same or similar features.

In a content-based filtering implementation, a model may be trained to generate recommendations of treatments or other regimens that are similar to treatments or other regimens used by the subject. The model may be used to evaluate information about the subject, such as features derived from the subject's prior treatment history (e.g., treatments that were effective) or the subject's stated treatment preferences. The model may then output a recommendation of a treatment or other regimen with the same or similar features.

At block 406, the system executing the process 400 may send regimen instructions to the module 100. In some embodiments, regimen instructions may be sent in the form of an executable function call and/or data identifying the regimen. For example, the data may represent a treatment identifier, treatment quantity, scheduled treatment time(s), sensor identifier, scheduled sensor data recording/transmission time(s), etc.

Figure 5:
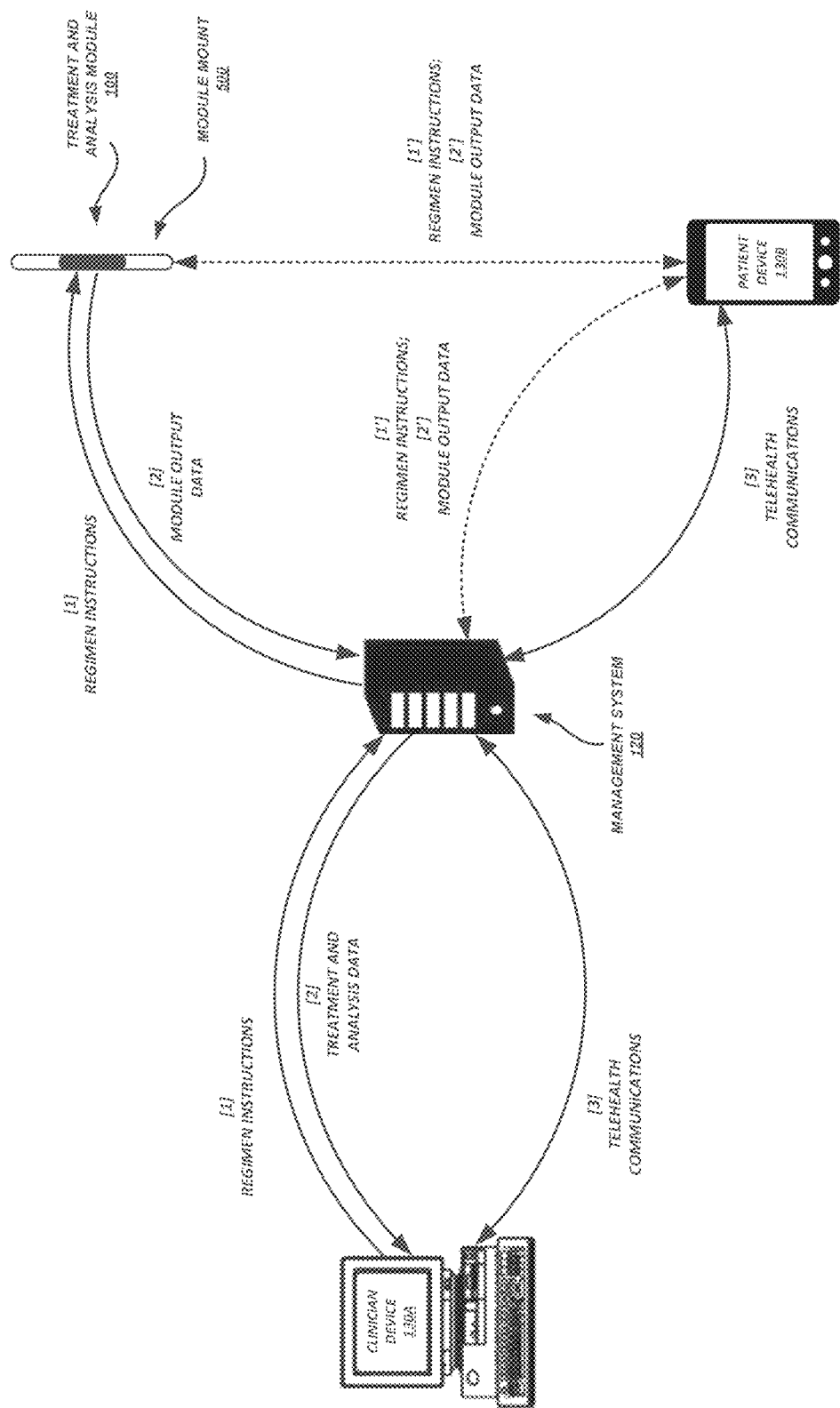
FIG. 5 is a diagram of illustrative data flows and interactions between user devices, a management system, and a treatment and analysis module according to some embodiments.

FIG. 5 illustrates an example in which a clinician device 130A generates and transmits regimen instructions to the management system 120 at [1]. The management system 120 then provides the regimen instructions to the treatment and analysis module 100. As shown, the treatment and analysis module 100 may be positioned on a subject via a module mount 500, such as a bandage, cast, strap, or other wearable medical article to which the module 100 is coupled. For example, the mount 500 may be worn such that the module 100, or individual sensors thereof (e.g., a camera sensor), is positioned over a particular body surface region of interest, such as a wound.

In some embodiments, the regimen instructions generated by the clinician device 130 may reference, include, or otherwise be associated with an identifier of a destination for the regimen instructions. For example, a unique account identifier of a user account of the wearer of the module 100 (e.g., a user account of a patient under the care of a clinician operating the clinician device 130A), or a unique identifier of the module 100 itself, may be selected or otherwise specified by the operator of the clinician device 130A. In some embodiments, the unique identifier may be numeric, or alpha-numeric. The management system 120 may maintain communication data that specifies where or how communications are to be sent to the module 100 identified in connection with the regimen instructions. For example, communication data associated with the identifier of the destination for the regimen instructions may be an internet protocol ("IP") address of a recipient, such as the module 100 or patient device 130B. Using this communication data, the management system 120 may transmit the regimen instructions. Instructions may be transmitted directly to the module 100 if the module is configured with network communication capabilities and is accessible to the management system 120. In some implementations, instructions may be transmitted to an intermediary device that is in communication with the module 100, such as the patient device 130B, indicated as [1']. A communication path between the patient device 130B and module 100 can be established to provide the regimen instructions, or data derived therefrom, to the module 100.

Returning to FIG. 4, at block 408 the system executing the process 400 may obtain data from the module 100. The data may include sensor data, data regarding a treatment administered by the module 100, other data, or some combination thereof. In some embodiments, sensor data may be or include an image of a body surface region of the wearer of the module 100, a temperature of the body surface region, an ambient temperature, a measurement of moisture of the body surface region, a measurement of ambient moisture, a measurement of pH of the body surface region, other measurements, or some combination thereof. In some embodiments, treatment data may represent a confirmation of application of the treatment, a quantity of treatment administered, or the like.

The system executing the process 400 (e.g., management system 120 or a user device 130) may obtain the data automatically, on demand, or in response to an event. For example, a clinician device 130A may request output data from the module 100. The request may be sent to the management system 120, which may provide the request to the module 100 directly or via an intermediary such as the patient device 130B, in a manner similar to that described with respect to providing regimen instructions. The module 100 may generate, access, or otherwise obtain the requested data and provide it to the requesting device. For example, as shown in FIG. 5, the module 100 may generate and provide output data (e.g., an image) at [2] to a clinician device 130A, directly or via the management system 120. As another example, the module may generate and provide output data at [2'] to a patient device 130B, which may or may not send the output data to the clinician device 130A, directly or via the management system 120.

At block 410, the system executing the process 400 may analyze the module output data. Analysis of the module output data may be performed (e.g., at the management system or a user device 130) using one or more models to determine one or more metrics, conditions, states, and/or recommendations. In some embodiments, an image analysis model system may be used to determine a current state of a body surface region or a change over time of the body surface region, as described in greater detail below. Data regarding the current state and/or change over time of the body surface region may in some embodiments be used to generate a recommendation such as a recommendation regarding a treatment to be administered.

In some embodiments, different machine learning models may be trained and targeted for use in classifying or otherwise evaluating different types of wounds, such as wounds from different types of injuries and/or surgeries. For example, a clinician may access the management system 120 via clinician device 130A and specify a type of surgery that was performed and/or a type of wound being analyzed. The clinician may do so at various times, such as when the treatment and analysis module 100 is first configured for the patient, or when data is received for analysis. The management system 120 may select, based on the specified surgery or wound type, a model or set of models to use to analyze sensor data from the treatment and analysis module 100. Other surgeries and/or wounds may result in selection of different models, and in some cases may result in evaluation of different sensor data. To facilitate automated and consistent use of models targeted for particular surgeries or wounds, the management system 120 may maintain data that maps surgery/wound types to models, sensor data, and the like.

At decision block 412, the management system 120 or a user device 130 may determine whether to continue an existing regimen. If so, the process 400 may return to block 408 for acquisition and analysis of further module output data, such as after administration of another treatment, after passage of a period of time, etc. Otherwise, if the existing regimen is not to continue, the process 400 may proceed to decision block 414.

In some embodiments, a decision of whether to continue an existing regimen may be based on a recommendation for a treatment or other aspect of the regimen, such as a recommendation (e.g., generated as described in greater detail above with respect to block 404). If the recommended treatment and/or other aspect of the regimen is the same, the existing regimen may continue. In some embodiments, a decision of whether to continue an existing regimen may be based on a classification and/or a score representing the current state of the subject's body surface region, such as a classification and/or score generated as described in greater detail below. In some embodiments, the decision may be based on a change in classification and/or score representing the current state of the subject surface region over time. An example process for determining such a change is described in greater detail below.

The decision of whether to continue an existing regimen may be interactive. For example, classification data, scoring data, and/or treatment recommendations may be generated and displayed on an interface of a clinician device 130A or patient device 130B. A user of the device displaying the information may determine whether to continue the existing regimen, and activate a user interface control representing the decision (e.g., a button to continue or a button to stop the current regimen). Depending upon the selected option, the current regimen may be continued or stopped.

In some embodiments, as shown in FIG. 5, the clinician device 130A may communicate with the patient device 130B at [3]. The communications may include text, video, and/or audio interactions between users of the devices 130A and 130B. For example, a user of a clinician device 130A may communicate with the subject using the patient device 130B to discuss an analysis of module output data, treatment regimens, or the like. Based on these communications, the user of the clinician device 130A and/or the subject using patient device 130B may determine whether or not to continue an existing regimen, and may indicate the determination on a user interface of the respective device 130A or 130B. In some embodiments, the clinician device 130A and/or patient device 130B may prompt for or otherwise receive input regarding post-operative pain (e.g., a pain score), range of motion, swelling, total blood loss, pre- and post-operative hematocrit level differences, or the like. Such input may be stored at the clinician device 130A, patient device 130B, and/or management system 120 for use in determining and monitoring a treatment regimen.

At decision block 414, the management system 120 or a user device 130 may determine whether to change the regimen that is to be performed by the module 100. If so, the process 400 may return to block 404, where the new regimen or change to existing regimen is determined. Otherwise, if treatment is not to continue, the process 400 may terminate at block 416.

In some embodiments, a decision of whether to change an existing regimen may be based on a classification and/or a score representing the current state of the subject's body surface region, or on a change in such classification and/or score, as described above. In some embodiments, the decision of whether to continue an existing regimen may be interactive, as described above. For example, the determination may be made based on classification, scoring, or other analysis results generated and displayed on an interface of a clinician device 130A or patient device 130B, communications between a clinician device 130A and patient device 130B, etc. Based on the displayed data and/or communications, the user of the clinician device 130A and/or the patient device 130B may determine whether or not to change the existing regimen or stop the regimen.

Example Process for Image Analysis and Scoring

Figure 6:
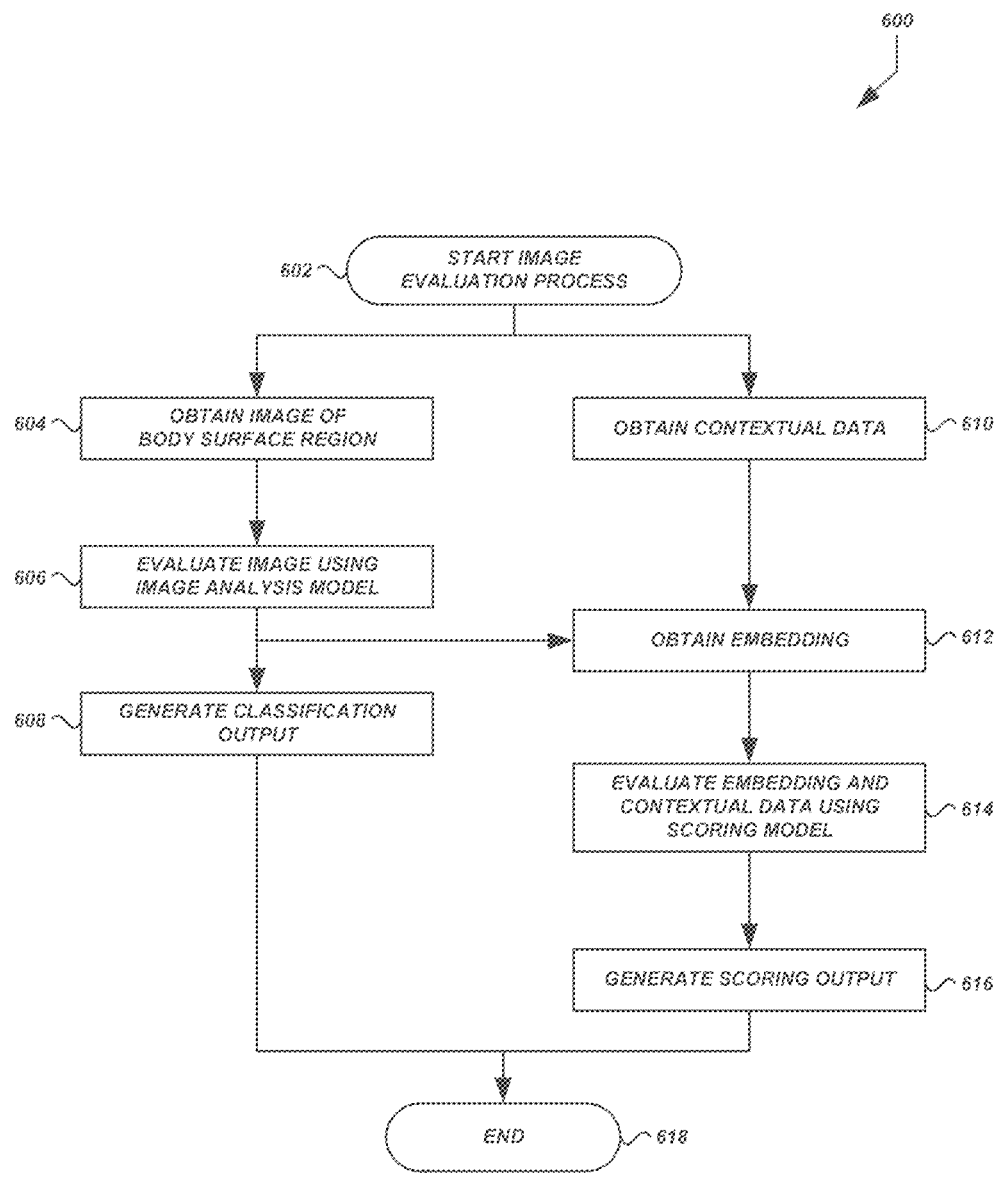
FIG. 6 is a flow diagram of an illustrative process for analyzing sensor data and contextual data according to some embodiments.

FIG. 6 is a flow diagram of an illustrative process 600 that may be executed to analyze image(s) obtained from the module 100. Analysis of an image of a patient body surface may include a comparison of the image to a database of images of "normal" results and "concerning" results, and/or use of a model trained based on such images. In some embodiments, a concerning result may cause generation of a message to the patient to submit images and analytics to a clinician (e.g., a doctor or other medical practitioner). In some embodiments, a concerning result may cause generation of a message to a clinician (e.g., rather than instructing the patient to do so).

In some embodiments, different machine learning models may be trained and targeted for use in classifying or otherwise evaluating different types of wounds, such as wounds from different types of injuries and/or surgeries. For example, a clinician may access the management system 120 via clinician device 130A and specify a type of surgery that was performed and/or a type of wound being analyzed. The clinician may do so at various times, such as when the treatment and analysis module 100 is first configured for the patient, or when data is received for analysis. The management system 120 may select, based on the specified surgery or wound type, a model or set of models to use to analyze images (and, in some cases, other sensor data) from the treatment and analysis module 100. Other surgeries and/or wounds may result in selection of different models. To facilitate automated and consistent use of models targeted for particular surgeries or wounds, the management system 120 may maintain data that maps surgery/wound types to models.

The process 600 or portions thereof may be executed by a user device 130 and/or management system 120, individually or in combination. For example, process 600 may be performed to analyze module output data from the module 100, such as during block 410 of process 400. Portions of the process 600 will be described with further reference to the illustrative image analysis model system 700 shown in FIG. 7.

The process 600 begins at block 602. The process 600 may begin in response to an event, such as when the management system 120 obtains an image captured by the module 100, when a user device 130 connects to the management system 120 to initiate analysis of an image (or set of images) captured by the module 100, or on a predetermined or dynamically-determined schedule. In some embodiments, process 600 or portions thereof may be performed on a predetermined or dynamically-determined schedule. For example, output data from the module 100 (images and/or other sensor data) may be obtained periodically, such as hourly, daily, or weekly. The module 100 may be programmed to initiate the capture and/or transfer of the output data, or another system such as the management system 120 or a user device 130 may request the output data from the module 100. In some embodiments, process 600 or portions thereof may be performed on-demand, such as when a user interacts with the module 100, a clinician device 130A, or a patient device 130B. In this way, process 600 may produce real time or substantially real time analysis. When the process 600 is initiated, a set of executable program instructions stored on one or more non-transitory computer-readable media (e.g., hard drive, flash memory, removable media, etc.) may be loaded into memory (e.g., random access memory or "RAM") of a computing device, such as a computing device of management system 120. In some embodiments, the process 600 or portions thereof may be implemented on multiple processors, serially or in parallel.

At block 604, the system executing the process 600 may obtain one or more images of a body surface region. The image may be captured by the module 100 and provided to a user device 130 and/or the management system 120. For example, an image of a region of a patient's skin may be captured, such as an image of a wound or skin condition. As another example, an image of a region of a patient's mouth may be captured, such as an image of an enamel surface or oral mucosa. In some embodiments, the images may be captured on demand, such as in response to a request from a clinician device 130A or patient device 130B, or in response to a direct user interaction with the module 100. The images may be obtained in the form of digital image files, such as bitmap images, tag image file format ("TIFF") images, Joint Photographic Experts Group ("JPEG") images, or the like.

Figure 7:
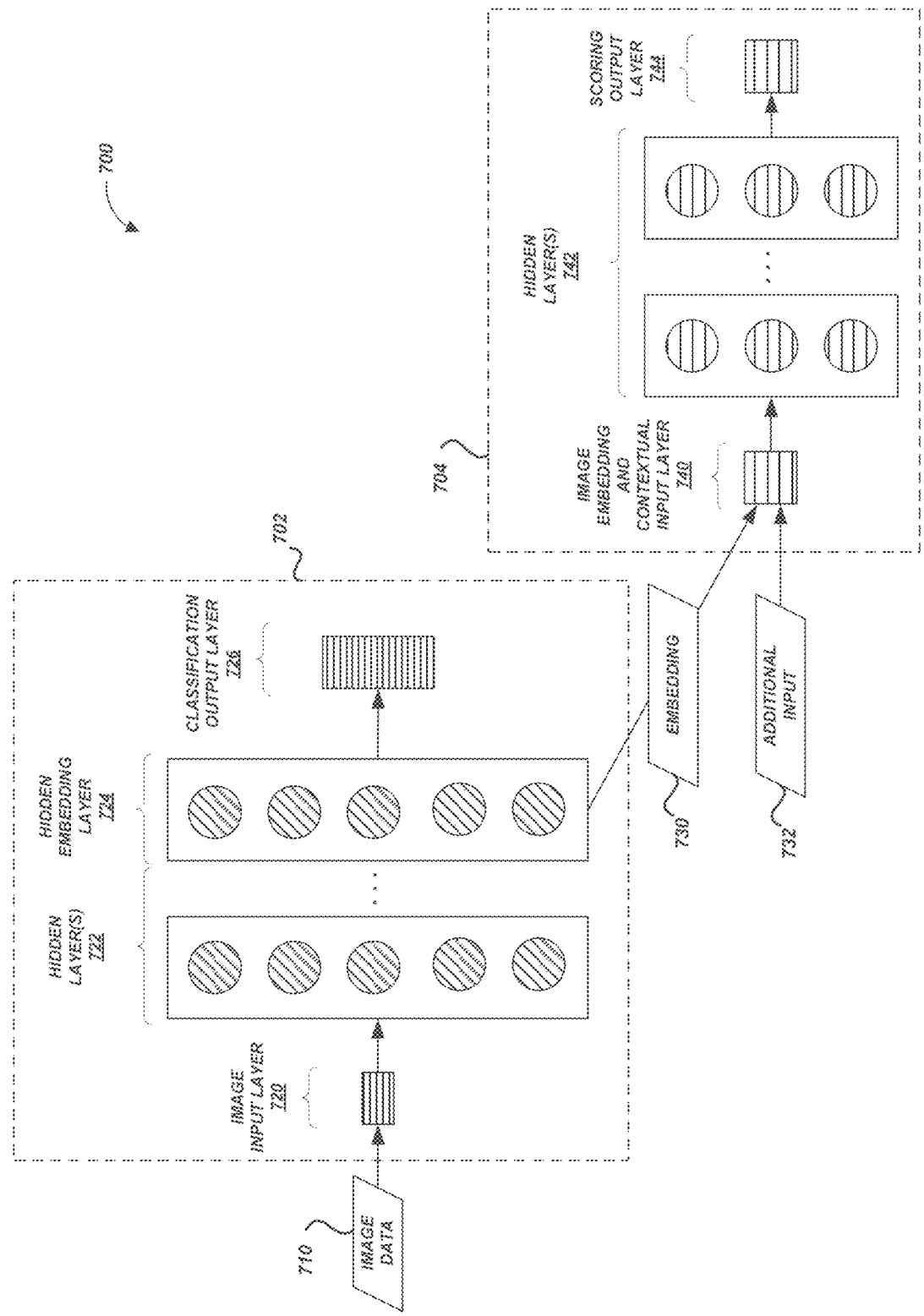
FIG. 7 is a diagram of an illustrative model system for analyzing sensor data and contextual data according to some embodiments.

At block 606, the system executing the process 600 may evaluate an image using an image analysis model or system of models, such as a machine learning model or system of such models trained to perform particular evaluations using images. FIG. 7 illustrates an example model system 700 that may be used to evaluate an image. In some embodiments, as shown, the model system 700 includes a classification model 702 and a regression model 704. The models 702 and 704 may be implemented as artificial neural networks. For example, the classification model 702 may be implemented as a convolutional neural network ("CNN") trained to classify images in any number of classes, and the regression model 704 may be implemented as a deep neural network ("DNN") trained to generate scores.

The classification model 702 may be trained to classify an image as depicting one of a set of conditions or condition severities. For example, the classification model 702 may be trained to classify an image as depicting a wound infection, a wound of a particular volume, a lesion that is a candidate for debridement, a skin abnormality, or the like. As another example, the classification model 702 may be trained to classify an image into one of a set of severity classes, such as wound severity, degree of acne, or other body surface condition severities. The set of severity classes may include a "normal" class, a "moderate" class, and a "severe" class. The training of the model may be performed using supervised or unsupervised methods. In one specific, non-limiting embodiment, the classification model 702 may be a ResNet-152 model.

The management system 120 or an external computing system may obtain training data input including a set of labeled training images (e.g., hundreds, thousands, or more individual labeled images). Various subsets of the set of labeled training images may depict body surface regions with the various conditions and/or condition severities that the model is to be trained to detect. Additional subsets of the set of labeled training images may depict body surface regions with no such conditions. The management system 120 may train the classification model 702 using the training data input, and the resulting trained classification model 702 may be deployed for use in analyzing and classifying images. In some embodiments, the set of labeled training images may be separated into two or more subsets, including one subset used to train the model, and another subset of images not used to train the model, but rather used to test the ability of the model to accurately classify. Segmenting the training data in this way can help to avoid overfitting the model to the training data. In some embodiments, the training data may be separated into k segments, or "folds" (where k is an integer greater than two) and a cross-validation procedure such as k-fold cross-validation, may be used to train and test the model.

In the embodiment illustrated in FIG. 7, the classification model 702 includes an image input layer 720 at which image data 710 is accepted (e.g., an image file, a vector derived from the image file, or some other representation of an image to be evaluated), one or more hidden layers 722 (e.g., convolutional layers, max pooling layers, fully connected layers, etc.), an embedding layer 724 (e.g., a last fully-connected layer before an output layer), and a classification output layer 726 (e.g., a layer of nodes at which sigmoid functions are evaluated to produce classification scores). The data generated at the embedding layer 724 may be structured as a vector representation of the features generated by the model 702 from the image input data. This vector representation may serve as an image embedding 730 that may be input to other models of the model system 700 for evaluation and production of output other than the classification output that the classification model 702 is trained to generate. For example, the image embedding 730 may be one input to the regression model 704.

In some embodiments, evaluation of an image of a patient body surface may include a comparison of the image to a database of images of "normal" results, a database of images of specific skin/wound conditions or otherwise "concerning" results, or to individual images that have been previously classified as "normal," indicative of specific skin or wound conditions, or otherwise "concerning." Similarity scores or other indicia of similarity may be generated as a result of comparing an image (or set of images) of a patient body surface region to previously classified images.

Returning to FIG. 6, at block 608 the system executing the process 600 may generate classification output based on evaluation of the image. In some embodiments, output produced by the output layer 726 of the classification model 702 may include one or more classification determinations, such as data indicating the particular class, of the classes for which the model 702 is trained to make classifications, in which the current image input data is most likely properly classified. For example, a classification determination may indicate the presence or absence of a body surface condition (e.g., a wound, a disease, etc.), or the severity of the body surface condition. As another example, the classification determination may indicate the volume or severity of a wound. As yet another example, the classification determination may indicate whether a body surface region is a candidate for debridement.

At block 610, the system executing the process 600 may obtain contextual data associated with the image being analyzed. The contextual data may represent one or more contextual data items regarding the subject whose body surface region is depicted in the image being analyzed, the location of the subject, and/or various other data that can be used to evaluate the confidence of the image classification. In some embodiments, the contextual data may include, but is not limited to: sensor data from one or more sensors 102 of the module 100, demographic data regarding the subject whose body surface region is depicted in an image (e.g., age, gender), skin tone data regarding the skin tone of the subject, location data representing the geographic location of the subject, weather data regarding the weather (e.g., temperature, humidity, UV index, wind conditions, etc.) at the geographic location of the subject, treatment data representing any treatment that the subject is using on the body surface region, subject-provided data (e.g., information provided by the subject regarding their activities, subjective evaluations, etc.), other contextual data, or some combination thereof. The example contextual data items described herein are illustrative only, and are not intended to be limiting, required, or exhaustive.

At block 612, the system executing the process 600 may obtain embedding data representing the image being analyzed. For example, the embedding data may be generated during evaluation of the image by the classification model 702, as described in greater detail above.

At block 614, the system executing the process 600 may evaluate the embedding data and contextual data using a scoring model or system of models, such as a machine learning model or system of such models trained to perform particular evaluations using images.

In one specific, non-limiting embodiment, the regression model 704 of the model system 700 shown in FIG. 7 may be trained to generate a score representative of a state of a body surface region, such as a state of health. Such a score may be referred to as a "state score" to distinguish it from other scores (e.g., scores representative of a confidence in a classification generated by the classification model 702). The training of the model may be performed using supervised or unsupervised methods. For example, the management system 120 or an external computing system may obtain labeled training data input including a set of image embeddings to user in a supervised training method. Each image embedding may be associated with a set of contextual data, such as the contextual data described above. Labels applied to the training data input items represent the scores to be generated for labeled training data input items by the trained model 704. The management system 120 may train the regression model 704 using the training data input, and the resulting trained regression model 704 may be deployed for use in analyzing images and additional data to generate state scores.

In the embodiment illustrated in FIG. 7, the regression model 704 includes an image embedding and contextual data input layer 740 at which an image embedding 730 and contextual input data 732 are accepted, one or more hidden layers 742, and a scoring output layer 744. The scoring output layer 744 may generate one or more scores, such a score in a range between a minimum and maximum value (e.g., 0-100). For example, the score may represent current state of health of a body surface region, where a higher score indicates a higher state of health. As another example, the score may represent current degree of severity of a health condition of a body surface region, where a higher score indicates a higher degree of severity.

Returning to FIG. 6, at block 616 the system executing the process 600 may generate scoring output based on evaluation of the image embedding and contextual data using the scoring model. For example, output produced by the output layer 744 of the regression model 704 may include one or more scores, as described above.

Example Process for State Change Analysis

Figure 8:
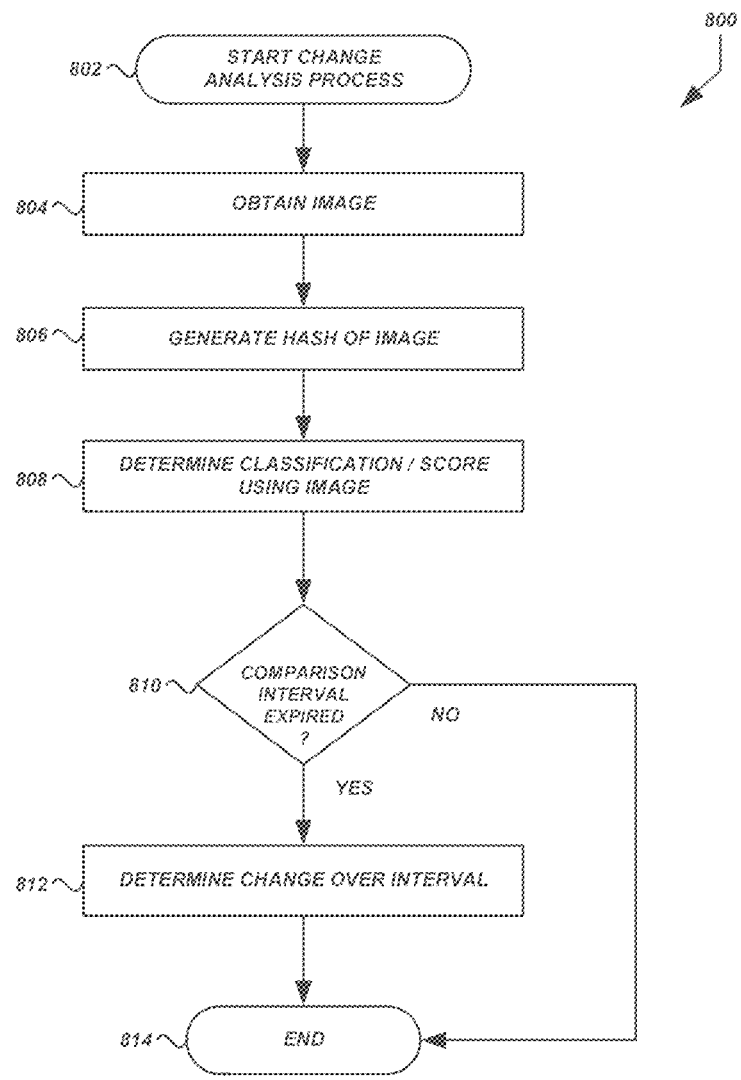
FIG. 8 is a flow diagram of an illustrative process for analyzing changes in sensor data and contextual data according to some embodiments.

FIG. 8 is a flow diagram of an illustrative process 800 that may be executed to analyze image(s) obtained from the module 100 and determine a change in state of a body surface region over time. The process 800 or portions thereof may be executed by a user device 130 and/or management system 120, individually or in combination. For example, process 800 may be performed to analyze module output data from the module 100, such as during block 410 of process 400.

The process 800 begins at block 802. The process 800 may begin in response to an event, such as when the management system 120 obtains an image captured by the module 100, when a user device 130 connects to the management system 120 to initiate analysis of an image (or set of images) captured by the module 100, or on a predetermined or dynamically-determined schedule. In some embodiments, process 800 or portions thereof may be performed on a predetermined or dynamically-determined schedule. For example, output data from the module 100 (images and/or other sensor data) may be obtained periodically, such as hourly, daily, or weekly. The module 100 may be programmed to initiate the capture and/or transfer of the output data, or another system such as the management system 120 or a user device 130 may request the output data from the module 100. In some embodiments, process 800 or portions thereof may be performed on-demand, such as when a user interacts with the module 100, a clinician device 130A, or a patient device 130B. In this way, process 800 may produce real time or substantially real time analysis. When the process 800 is initiated, a set of executable program instructions stored on one or more non-transitory computer-readable media (e.g., hard drive, flash memory, removable media, etc.) may be loaded into memory (e.g., random access memory or "RAM") of a computing device, such as a computing device of management system 120. In some embodiments, the process 800 or portions thereof may be implemented on multiple processors, serially or in parallel.

At block 804, the system executing the process 800 may obtain an image of a body surface region. The image may be captured by the module 100 and provided to a user device 130 and/or the management system 120. For example, an image of a region of a patient's skin may be captured, such as an image of a wound or skin condition. As another example, an image of a region of a patient's mouth may be captured, such as an image of an enamel surface or oral mucosa. In some embodiments, the images may be captured on demand, such as in response to a request from a clinician device 130A or patient device 130B, or in response to a direct user interaction with the module 100. The images may be obtained in the form of digital image files.

At block 806, the system executing the process 800 may generate an encoded version of the image, such as a hash. The encoded version may be stored for later use in comparison operations with prior or subsequent images of the same body surface region to determine whether there has been a change in the condition of the body surface region.

In some embodiments, the encoded version may be an average hash. For example, the image may be converted to grayscale and scaled to a standard size, such as an image that is 255×255 pixels. An average of pixel values may be calculated, and individual pixels or subsets thereof may be compared to the average. If the pixels are darker than average, a particular value (e.g., 1) may be added to the hash for the pixel location, and if the pixels are lighter than average, a different value (e.g., 0) may be added to the hash for the pixel location.

In some embodiments, the encoded version may be a distance hash. For example, the image may be converted to grayscale and scaled to a standard size. For each row, each pixel value may be compared to the value of an adjacent pixel, such as the pixel to the immediate right. If the current pixel value is darker than the value of the adjacent pixel, a particular value (e.g., 1) may be added to the hash for the pixel location, and if lighter than the adjacent pixel, a different value (e.g., 0) may be added to the hash for the pixel location.

In some embodiments, the encoded version may be an embedding. For example, an embedding generated during the classification and scoring process and illustrated in FIG. 7 may be stored for use in subsequent comparisons and other analyses.

The example image encoding methods and formats described herein are illustrative only, and are not intended to be limiting, required, or exhaustive.

At block 808, the system executing the process 800 may determine a classification and/or a score for the image. In some embodiments, the classification and/or score may be generated as described in greater detail above and illustrated in FIG. 7.

At decision block 810, the system executing the process 800 may determine whether a time interval for comparison has expired. If so, the process 800 may proceed to block 812. Otherwise, if the time interval for comparison has not expired, the process 800 may terminate at block 814. The time interval for comparison may be predetermined or dynamically determined. For example, the time interval may be set such that the process 800 proceeds to block 812 on a daily, weekly, or monthly basis.

At block 812, the system executing the process 800 may determine the change in the subject's body surface region over the time interval. The change may be determined using the encoded representations of images for the current image and an image preceding the time interval, classification data generated for the respective images, scoring data generated for the respective images, other data, or some combination thereof.

In some embodiments, encoded representations of the current image and a prior image may be compared to determine the difference between the encoded representations. For example, a Manhattan distance or a Euclidian distance between two encoded representations may be determined. Output may be generated indicating the degree to which the encoded representations differ based on the determined distances.

In some embodiments, the scores of the current image and a prior image may be compared to determine the difference between the encoded representations. For example, the score for the current image may be subtracted from the score for a prior image, or vice versa. The difference may represent the degree to which the condition of the body surface region has changed. Illustratively, the degree may correspond to a degree of healing of a wound, a degree of improvement or deterioration of a condition, or the like.

In some embodiments, the classifications of the current image and a prior image may be compared to determine the difference between the encoded representations. For example, each classification may be assigned a numerical value in increasing or decreasing degree of severity. The numerical value for the classification of the current image may be subtracted from the numerical value for the classification of the prior image, or vice versa. The difference may represent the degree to which the condition of the body surface region has changed. Illustratively, the degree may correspond to a degree of healing of a wound, a degree of improvement or deterioration of a condition, or the like.

The change(s) determined at block 812 may be presented to a user (e.g., via a user interface of a user device 130) and/or stored for future analysis, reporting, or the like (e.g., stored on a user device 130 or at the management system 120).

Figure 9:
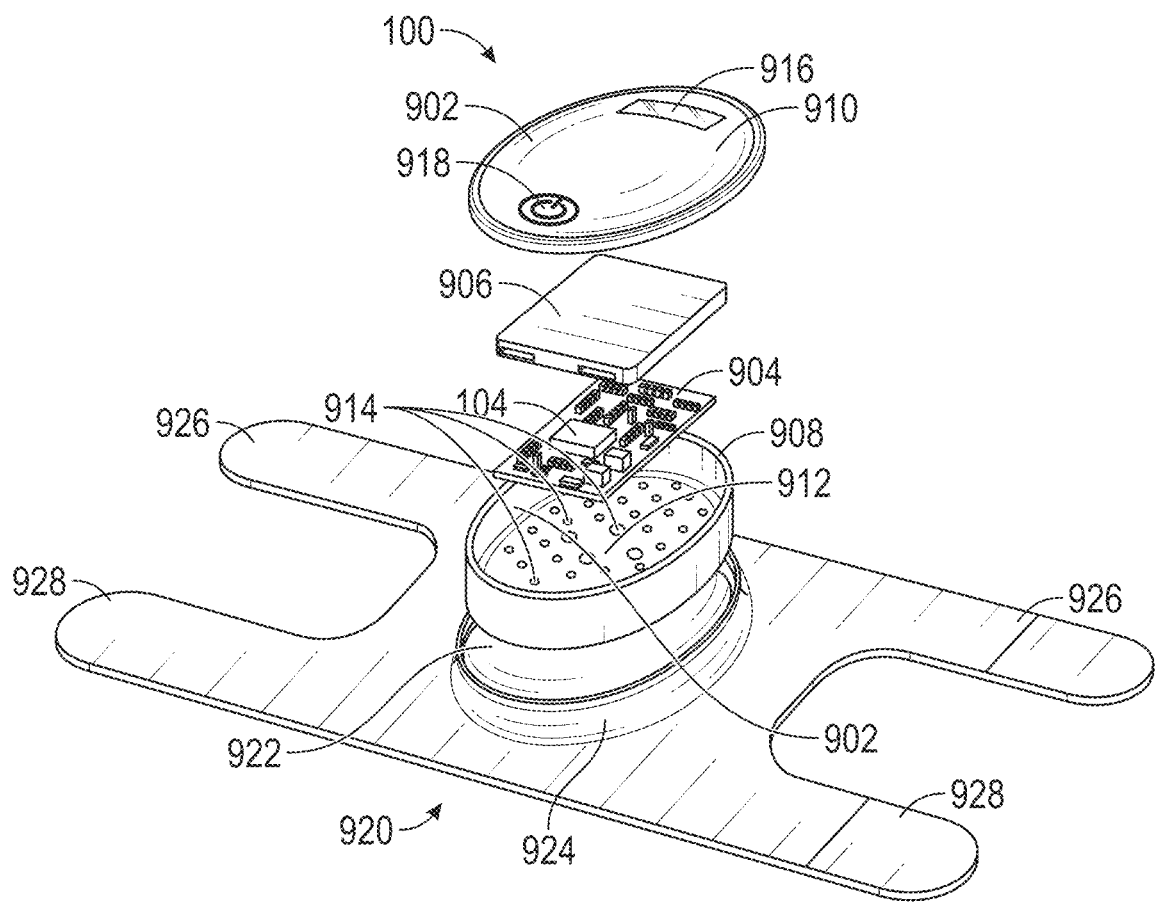
FIG. 9 is a perspective, exploded view of an embodiment of the module and an associated fitted wrap.

Example of Wearable Treatment and Analysis Module for Wounds and Other Skin Conditions As seen in FIG. 9, an illustrated embodiment of the wearable treatment and analysis module 100 includes a housing 902, a circuit board 904, and onboard battery 906. The housing 902 as shown generally has an oval shape formed by a lower base 908 and an upper lid 910. The shape and structure of the housing, however, can differ and preferably will be suited for specific applications. For example, in some embodiments, only a portion of an upper portion of the housing 902 can be removed, and in other embodiments, two or more side-by-side components can define part or all of the housing 902. Additionally, the coupling between the base 908 and the lid 910 (or between other components that define the housing 902) can be releasable or permanent.

In the illustrated embodiment, the lower base 908 has lower surface 912 with a concave shape that generally approximates a surface of the patient's body against which it will rest. The lower surface 912 preferably has a sufficient size to extend over and beyond the margins of the patient's wound that it's designed to cover. A flange or similar mounting structure (not shown in FIG. 9) can extend from a lower portion of the base 908 to facilitate attachment of the module 100 to the patient. For example, a flange may be mounted to or embedded within a surgical foam pad that is sized and/or shaped to cover or substantially cover a wound and, in some cases, the body surface around or adjacent to the wound. The surgical foam pad may have an aperture to provide would access to the module 100 or components thereof (e.g., optical access for a camera sensor; environmental access for a temperature or moisture sensor, etc.).

With the lid 910 attached to the base 908, the housing 902 defines an internal space. That space preferably is sufficiently large to house the printed circuit board 904 (with all its components as described below) and to provide the field depth needed for any optical elements (e.g., camera sensor 102) of the module 100. The space, however, should be minimized so as to provide the housing 902 with a slim profile and to be more form fitting. As such, the module 100 can be lighter in weight and lower in profile as it sits over the patient's wound area so as to minimize discomfort and skin irritation. The minimized profile and size also allow the module 100 to be placed within bandages, casts and the like for a wide range of wearables, including but not limited to compression bandages, negative pressure wound therapy devices, optical coherence tomography devices, and microelastography devices.

While in the illustrated embodiment the housing 902 has a fixed profile, in other embodiments the profile can be increase before application or can be temporally increased during application to the patient. In one form, telescoping components of the housing 902 can provide for increased height to enlarge the field of view or coverage for one or more components of the module 100 (e.g., for a camera sensor 102). A user (e.g., a healthcare provider) can increase the housing's profile manually or the module 100 can include an actuating system—for example, having one or more electric or pneumatic actuators—to move the telescoping components or to move the camera sensor 102 (or other components within the housing 902 (e.g., the circuit board 904)) relative to the patient's wound or skin.

As illustrated in FIG. 9, the lower surface 912 of the housing 902 supports a series of optical elements 914, for example, LEDs and lens(es). The LEDs can be used to illuminate the skin or wound to enhance imaging, for light therapy to help improve or heal the skin condition or wound, or both. LEDs or other optical elements 914 that emit light to improve or heal a skin condition or wound may be configured to emit light in one or more wavelengths, such as visible light, infrared light, or other wavelengths. A controller/processor 104 on the circuit board 904 controls the LEDs, and the battery powers the LEDs. Alternatively, the circuit board 904 can support the LEDs with the LEDs aligning with apertures in the bottom surface 912 of the housing 902.

Each lens of the module 100 can be auto-focusing, rotatable or otherwise movable, and/or able to zoom in or out. These features allow the user—or controller 104 if automated—to capture images of all or substantially all of the affected area (e.g., the wound) or targeted skin area, as well as to image segments of the affected or targeted area (e.g., the wound's margins and healed boundaries). For these purposes, the controller 104 control each lens with the battery 906 supplying power thereto. In other embodiments, the lens can be fix. Additional filters (either physical or software) can be used to enhance the images.

The lower surface 912 of the housing 902 also can include one or more apertures. Such apertures can form part of the treatment dispenser 110 to apply a treatment agent (e.g., a therapeutic, topical fluids, ozone, etc.) to the patient's skin/wound. In some embodiments, the aperture(s) can also form part of the negative pressure wound therapy; fluids within a space between the wound and the bottom surface 912 of the module housing 902 are drawn through the aperture(s) to reduce the pressure within that space.

Moreover, as noted above, the module 100 can also or alternatively provide waveform-based treatments, such as ultraviolet light or ultrasound. The treatment dispenser 110 for such treatments may include corresponding emission devices, such as ultraviolet light emitting diodes (as part of an array of LEDs supported by the circuit board 904 or the bottom surface 912 of the housing 902) and/or ultrasonic transducers. The ultrasonic transducers can extend through or be supported on the lower surface 912 of the module housing 902.

The printed circuit board 904 can be rigid but preferably is flexible, and supports and interconnects a plurality of the module's components including the controller/processor 104, sensors 102, data storage 106, and network interface 108. In some embodiments, the circuit board 904 also can support and interconnect at least some components of the treatment dispenser 110 and/or the fluid treatment storage 112. For example, in some embodiments, the treatment dispenser 110 can include a dispensing medicant pump or the like that draws fluid from the fluid treatment storage 112 when operated by the controller 104.

At least some of the sensors 102 are positioned on the printed circuit board 904 to correspond to the apertures and lens(es) supported by the lower surface 912 of the housing 902. For example, the camera sensor 102 is located on the printed circuit board 904 such that it aligns with a lens or aperture on the lower surface 912 of the housing base 908 when the printed circuit board 904 is positioned and secured in the housing 902. In some embodiments, this position lies generally at the center of the lower surface 912.

The battery 906 supplies power to the components on the printed circuit board 904 and to the LEDs on the lower surface 912 of the housing 902, and is attached to these components by one or more detachable leads. The battery 906 preferably is rechargeable either by an external port on the housing 902 or by induction. The size of the battery preferably allows the module 100 to operate for at least one day before requiring charging, but is not too large to dramatically increase the module's profile. In some embodiments, the battery 906 can be replaced while the module 100 is attached to the patient by removing the housing upper lid 910 and disconnecting and replacing the battery 906.

In some embodiments such as the one shown in FIG. 9, the module 100 also can include a digital screen displace 916 (e.g., a touch screen) on the upper surface of the module, for example on the upper lid 910. Indicator lights (not shown) can also or alternatively be used to provide information to the user, for example to indicate a low battery condition. The module 100 can operate a similar UI/UX to the that used with a user device to provide controls for the module and/or to communicate data (e.g., an image of the covered wound). The module 100 will also include a screen driver and additional processing software or firmware for this purpose. As seen in FIG. 9, the module also can include an on-off button 918 positioned on its upper lid 910

Figure 10:
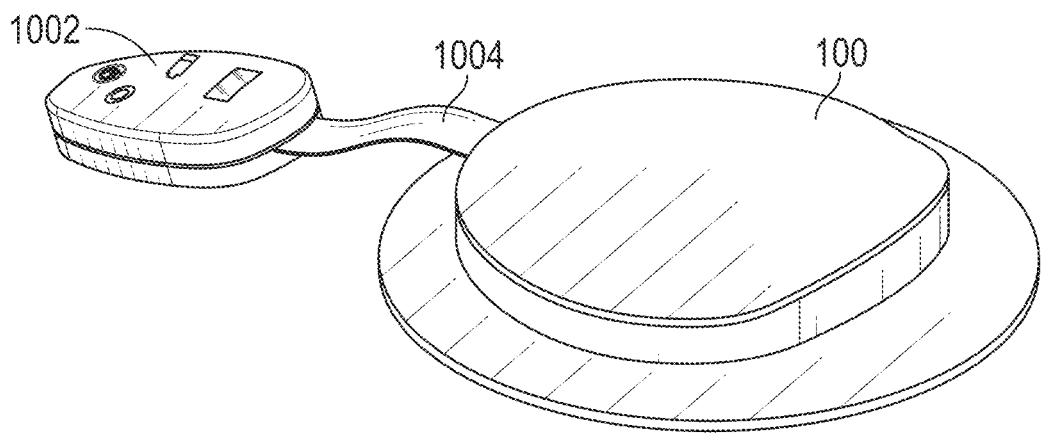
FIG. 10 is a perspective view of another embodiment of the module attached to a patient by an adhesive pad.

While in the illustrated embodiment of FIG. 9 the battery 906 and all of the components attached to the printed circuit board 904 are located within the module housing 902, in other embodiments, such as seen in FIG. 10, certain components of the module 100 can be located in a separate device 1002 that is attached to the module 100. For example, some or all of the battery, processor, data storage, network interface can be located in the separate device 1002 and attached to the module 100 by a cable 1004. This approach allows the module 100 to be slimmer and more form fitting; allows the module 100 to be fully enclosed/wrapped and controlled without taking off bandages; and reduces the profile and weight over the patients' wound area. The separate device 1002 can be similarly worn by the patient at a location remote from the wound or be attached to the worn module 100 when gathering data (e.g., when imaging).

The module 100 can be attached to the patient in a variety of ways including being fitted within bandages (including elastic compression bandages such as those used after total knee replacement and other joint replacement surgeries), wraps, and casts. For example, as FIG. 9 illustrates, the module 100 can be form fit on and worn outside an associated wrap 920. The wrap 920 includes an aperture 922 sized to receive at least the lower surface 912 of the module 100. Interconnecting structures operate between the module housing 902 and the wrap 920 to secure the module 100 to the wrap 920. In some embodiments, the module 100 can be released from the wrap 920, in others its permanently affixed. The wrap 920 preferably is formed of a biocompatible, breathable, skin-friendly material at least on its underside (that is, the side in contact with the patient's skin) and has a relatively large central portion 924 to support the module 100 on the patient. In the illustrated embodiment, the wrap 920 includes two pairs of legs 926, 928 that extend from the central section 924. Each leg parings 926, 928 interconnects using a hook-and-loop fastener (e.g., Velcro®). That is, one leg 926, 928 includes the loop portion and other corresponding leg 926, 928 includes the hook portion. Each leg pairings 926, 928 can be wrapped around the patient—for example, around the patient's forearm—and attached to each other. In this manner, the wrap 920 secures the module 100 onto the patient's skin. The wrap 920 additionally can include an adhesive layer on its lower surface in some applications.

Figure 11:
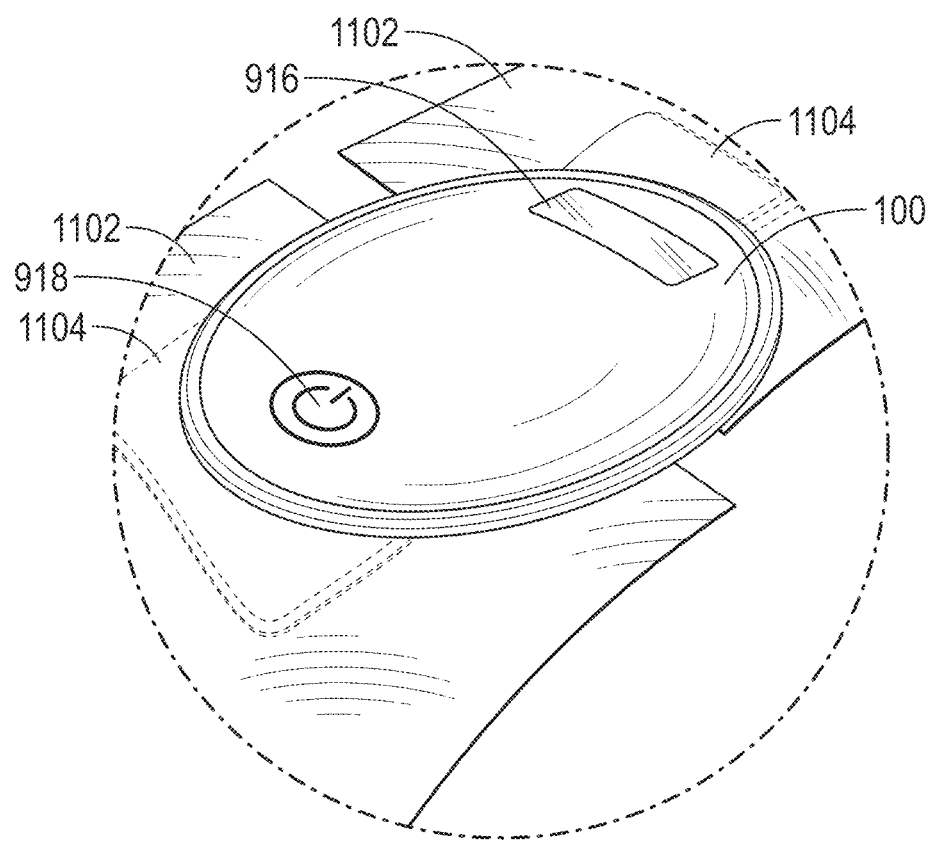
FIG. 11 is a perspective view of the module embodiment of FIG. 9, shown fully assembled and attached to a patient with conventional bandages and gauze.
Figure 12:
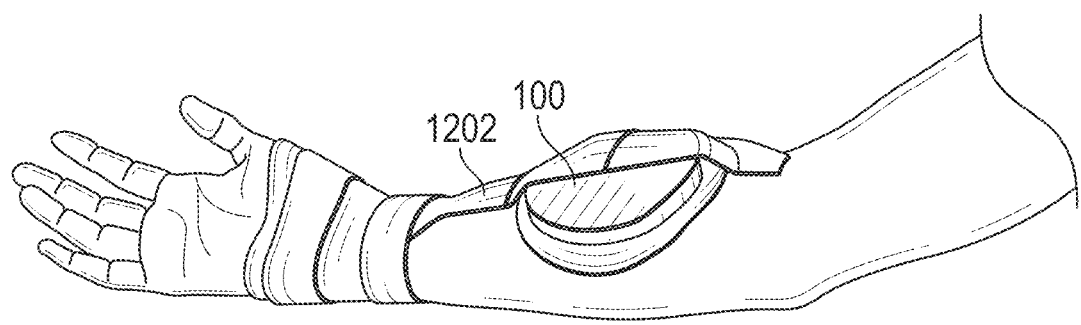
FIG. 12 is a perspective view of the module embodiment of FIG. 9, shown fully assembled and attached to a patient with a conventional wrap.

By way of additional examples, FIG. 11 illustrates the module 100 attached to a patient using standard adhesive coverings 1102. In this example, gauze 1104 is located between portions of the module 100 and patient's skin, beneath the coverings 1102. FIG. 12 illustrates another example with the module 100 attached beneath or embedded within a wearable medical article such as a wrap 1202. In some embodiments, the module 100 can be placed on a patient and then encased in a cast (e.g., arm cast) or other protective shell. In other embodiments, the module can be sutured to the skin, although this is less preferred.

In some embodiments, the housing 902 of the module 100 may be form, in whole or in part, from a material configured to permit wireless communication from a network interface 108 within the housing. If the network interface 108 is or includes a high-speed wireless antenna, such as a 5G antenna, the housing 902 may be formed of material that does not interfere, or does not substantially interfere, with communications to and/or from the network interface 108. For example, the housing 902 may be formed of or include any of the following materials from DuPont®: Crastin polybutylene terephthalate (PBT); Zytel HTN range of high-temperature polyamides; or Hytrel thermoplastic polyester elastomer.

Figure 13A:
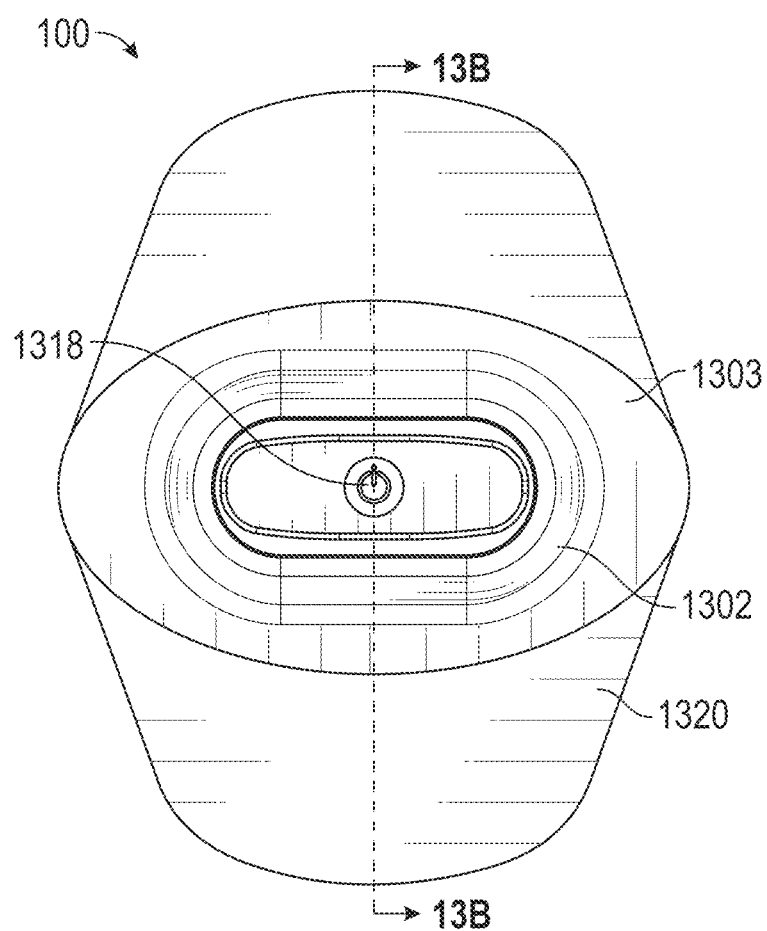
FIG. 13A is a top plan view of another embodiment of the treatment and analysis module that comprises a housing forming a receptacle.
Figure 13B:
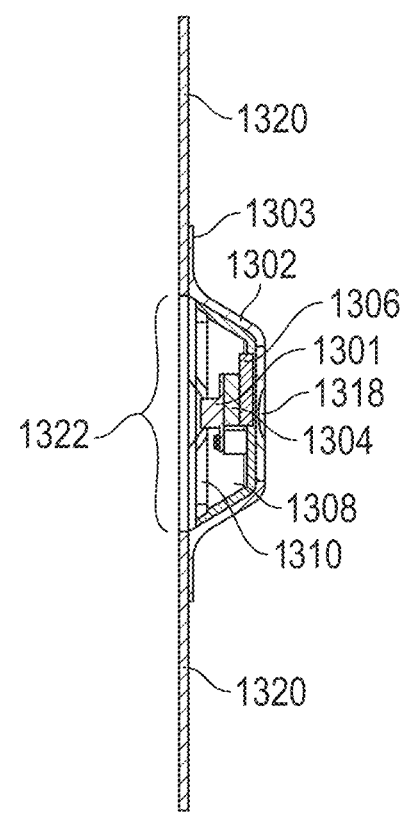
FIG. 13B is a cross-section view through the module in FIG. 13A showing a camera sensor and a battery disposed in the receptacle of the housing.

Example of Wearable Treatment and Analysis Module for Wounds and Other Skin Conditions FIG. 13A is a top plan view of another embodiment of the treatment and analysis module 100. FIG. 13B is a cross-section view through the module 100 in FIG. 13A. In the illustrated embodiment, the module 100 comprises a housing 1302 forming a receptacle 1308. In the illustrated embodiment, an outer surface of the housing 1302 has a generally tapering oval shape. Of course, the shape of the housing 1302 is not limited to the illustrated shape and can instead have any other shape. For example, the shape and structure of the housing 1302 can differ and preferably will be suited for specific applications. While in the illustrated embodiment the housing 1302 has a fixed profile, in other embodiments disclosed herein the profile can be increase before application or can be temporally increased during application to the patient.

Figure 20:
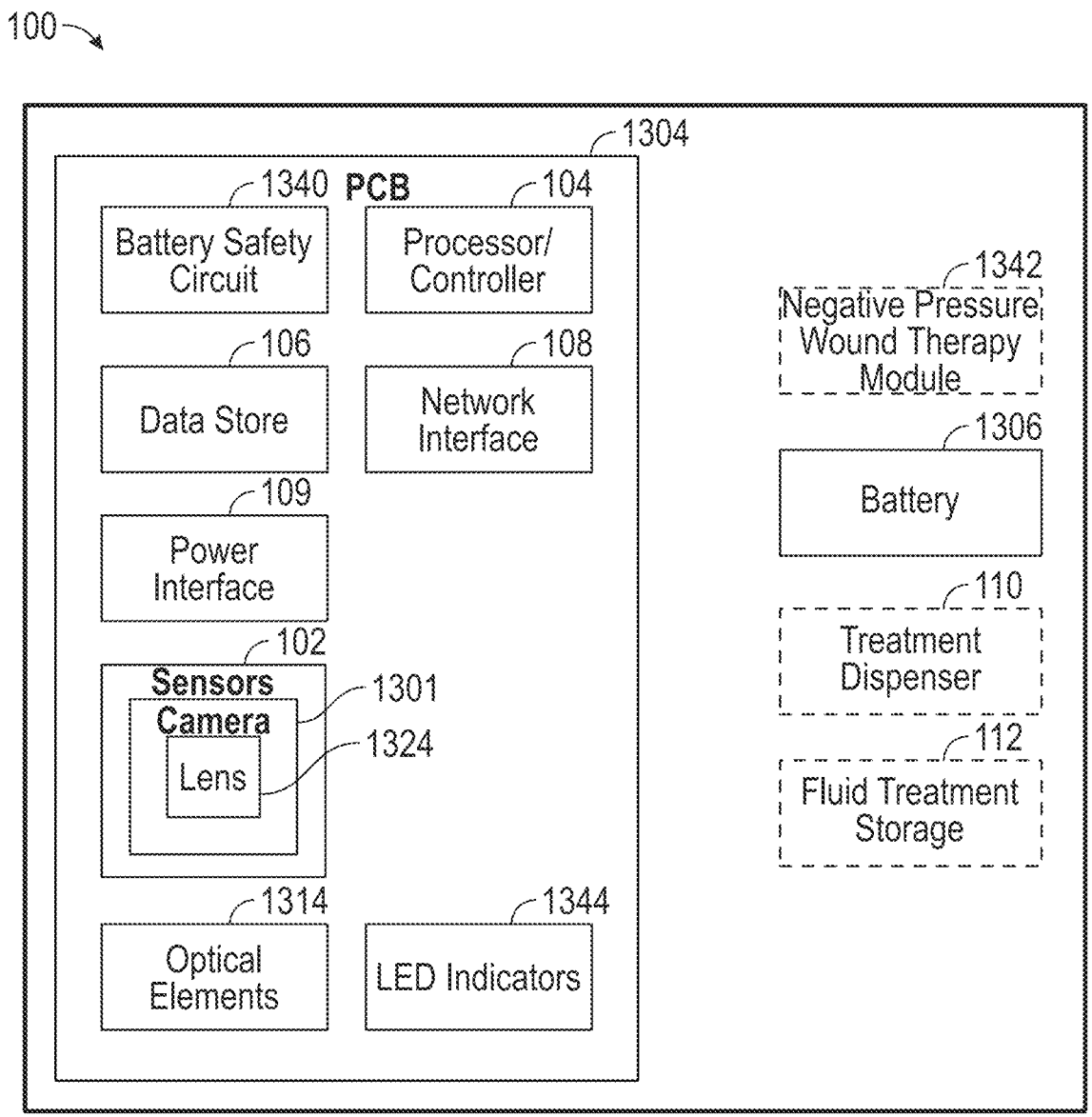
FIG. 20 is a schematic view of the module from FIG. 13A.

In certain embodiments, the module 100 includes the network interface 108 (FIG. 20). The network interface 108 allows the module 100 to transmit and receive data. The network interface 108 can be a wired or wireless interface, such as a network adapter card and/or a wireless antenna (e.g., a Wi-Fi antenna, a Bluetooth® antenna, etc.). Similarly, the power interface 109 (FIG. 20) can be a wired or wireless interface, such as a receiver configured to receive power via a time-varying electromagnetic field (e.g., inductive coupling, resonant inductive coupling, capacitive coupling, magneto dynamic coupling, microwaves, and light waves, etc.) and convert the power back to an electric current. While illustrated as having a continuous outer surface in FIG. 13A, in certain embodiments, the network interface 108 and/or the power interface 109 can include one or more connectors accessible through the housing 1302. Of course, in embodiments that wirelessly transmit and receive data and/or receive wireless power, the module 100 need not include accessible connectors accessible through the housing 1302.

In certain embodiments, the housing 1302 comprises a flange 1303. In certain embodiments, the flange 1303 extends in an outward direction from a lower opening (FIG. 17) into the receptacle 1308. In the illustrated embodiment, a distance the flange 1303 extends away from the lower opening varies around the perimeter of the lower opening.

In certain embodiments, a surgical foam pad may be sized and/or shaped to cover or substantially cover a wound and, in some cases, the body surface around or adjacent to the wound. The surgical foam pad may have an aperture to provide would access to the module 100 or components thereof (e.g., optical access for a camera sensor; environmental access for a temperature or moisture sensor, etc.). The flange 1303 may be mounted to or embedded within the surgical foam pad.

In certain embodiments, the module 100 comprises a platform 1320. In certain embodiments, the platform 1320 is configured to be secured, directly or indirectly, to the patient. In the illustrated embodiment, the platform 1320 has a generally oval planar shape. Of course, the platform 1320 can have any shape. In the illustrated embodiment, at least a portion of the platform 1320 extends beyond an outer perimeter of the flange 1303 to increase a contact area between the module 100 and the patient. In certain embodiments, a lower surface of the platform 1320 has a concave shape that generally approximates a surface of the patient's body against which it will rest. In certain embodiments, the lower surface of the platform 1320 has a sufficient size to extend over and beyond the margins of the patient's wound that it is designed to cover. In certain embodiments, the platform 1320 has a higher degree of flexibility than the housing 1302 to allow the platform 1320 to more easily bend so as to, for example, wrap about a limb or follow the curvature of a torso of the patient. In certain embodiments, a wrap or similar mounting structure (not shown in FIG. 13A) attaches to the platform 1320 for facilitating attachment of the module 100 to the patient. In certain embodiments, the platform 1320 includes an adhesive for adhering the module 100 to the patient.

In certain embodiment, the housing 1302 and the platform 1320 are manufactured as separate structures before being assembled together. In certain embodiments, the housing 1302 and the platform 1320 are assembled using an adhesive or other coupling structure known to a person having ordinary skill in the art. In certain embodiment, the housing 1302 and the platform 1320 are manufactured as a unitary structure. In certain embodiments that do not include the platform 1320, the flange 1303 of the housing 1302 can instead be sized and shaped to be secured, directly or indirectly, to the patient.

In the illustrated embodiment, the platform 1320 comprises an opening 1322 aligned with the lower opening into the receptacle 1308. In this way, the platform 1320 does not block access to the receptacle 1308 when the housing 1302 is coupled to the platform 1320.

In certain embodiments, one or more sensors/components are located in the receptacle 1308. In certain embodiments, the one or more sensors/components comprise any of the sensors/components described with respect to FIGS. 1, 2, and 20. For example, in certain embodiments, the one or more sensors/components comprise a camera sensor 1301 and a battery 1306. As is explained below, in certain embodiments, the camera sensor 1301 and the battery 1306 are configured to be separately removable from the receptacle 1308 for ease of recycling.

In the illustrated embodiment, the camera sensor 1301 is disposed on a printed circuit board ("PCB") 1304. In embodiments that include the PCB 1304, the PCB 1304 can be rigid but preferably is flexible, and supports and interconnects a plurality of the one or more sensors/components. For example, in certain embodiments, the PCB 1304 supports not only the camera sensor 1301 but also additional sensors/components. In certain embodiments, the camera sensor 1301 is configured as a standalone device disposed in the receptacle 1308 along with the battery 1306. In certain embodiments, no PCB 1304 is employed.

In certain embodiments, the module 100 comprises a cover 1310. In certain embodiments, the cover 1310 is sized and shaped to releasably secure in the lower opening into the receptacle 1308. When the cover 1310 is attached to the housing 1302, the receptacle 1308 is defined therebetween. In certain embodiments, the receptacle 1308 is sufficiently large to house the one or more sensors/components. In embodiments that include the PCB 1304 supporting the one or more sensors/components, the receptacle 1308 is sized to house the PCB 1304 (with all its sensors/components). In certain embodiments, a depth of the receptacle 1308 is selected to provide the field depth needed for the camera sensor 1301 or any other optical elements (e.g., for fluorescence imaging, light therapy, etc.) of the module 100. A size of the receptacle 1308 can be minimized so as to provide the housing 1302 with a slim profile and to be more form fitting. As such, the module 100 can be lighter in weight and lower in profile as it sits over the patient's wound area so as to minimize discomfort and skin irritation. The minimized profile and size also allow the module 100 to be placed within bandages, casts and the like for a wide range of wearables, including but not limited to negative pressure wound therapy devices, optical coherence tomography devices, and micro-elastography devices.

In certain embodiments, a film or foam dressing (e.g., surgical foam) is employed. For example, in certain embodiments, the dressing can cover the wound or area of interest on the patient. In certain embodiments, the dressing can be used to attach the module 100 to the patient. In certain embodiments, the dressing can comprise a foam with hydrophilic properties and an outer layer of hydrophobic properties with adhesive borders. For dressings that are not transparent, a hole can be cut in the dressing over the wound before attaching the module 100. In this way, the wound or area of interest on the patient is viewable by the camera sensor 1301.

In certain embodiments, a thickness of the dressing placed between the skin of the patient and the platform 1320 is selected to achieve a desirable spacing between the housing 1302 and the skin of the patient. For example, in certain embodiments, thicker (or multiple layers) dressing can be selected to increase a distance between the housing 1302 and the skin of the patent. In this way the housing 1302 can move from a low-profile state to a raised-profile state. This adjustability can be advantageous since it changes a field of view of the camera sensor 1301. In some embodiments, a first view may be a wider-angle view than a second view due to the optical configuration of the camera sensor 1301. For example, the camera sensor 1301 may be configured to transition from the low-profile state to the raised profile state in order to zoom in on a particular subregion of the skin of the patient. In addition to or in lieu of changing a thickness of the dressing, the adjustability may be obtained by manual application of force (e.g., a user turns a zoom ring, applies pressure, etc.). In some embodiments, the module 100 and/or the camera sensor 1301 may include a motorized subsystem for transitioning from the low-profile state to the raised-profile state and vice versa. Images captured in the different states may show wide-angle and zoomed-in views, respectively. In certain embodiments, as disclosed herein, one or more structures telescope from the module 100 to transitioning the module 100 from the low-profile state to the raised-profile state and vice versa.

Figure 14A:
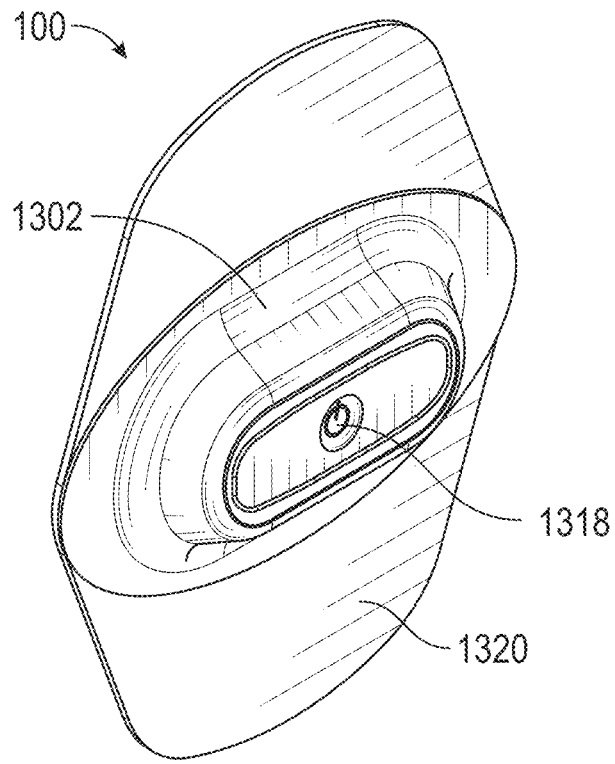
FIG. 14A is a left isometric view of the module from FIG. 13A showing a platform of the housing configured to be secured relative to a patient.
Figure 14B:
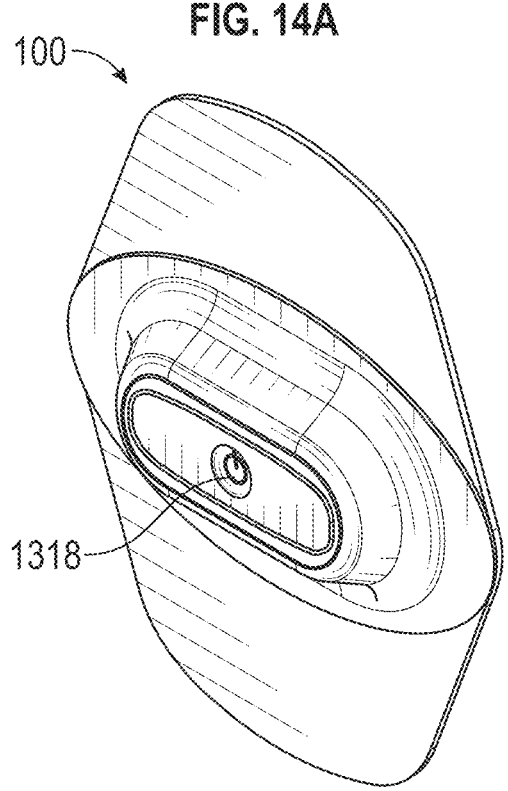
FIG. 14B is a right isometric view of the module from FIG. 13A.

FIG. 14A is a left isometric view of the module 100 from FIG. 13A showing the platform 1320 of the housing 1302 configured to be secured relative to the patient. FIG. 14B is a right isometric view of the module 100 from FIG. 13A. In certain embodiments such as the one shown in FIGS. 14A-B, the module 100 also can include an on-off button 1318. In certain embodiments, the module 100 comprises a display (not shown) and/or one or more indicator lights 1344 on an upper surface of the housing 1302. In certain embodiments, the display and/or indicator lights 1344 provide information to the healthcare worker or patient, for example, to indicate a low battery condition. In certain embodiments, the flashing of the indicator light 1344 can be seen through a bandage or an audio sound can be heard by the patient to inform the patient of operational status. In certain embodiments, the information can be shared with the user devices 130. The module 100 can operate a similar UI/UX to the that used with the user device 130 to provide controls for the module and/or to communicate data (e.g., an image of the covered wound). The module 100 can include a screen driver and additional processing software or firmware for this purpose.

Figure 15A:
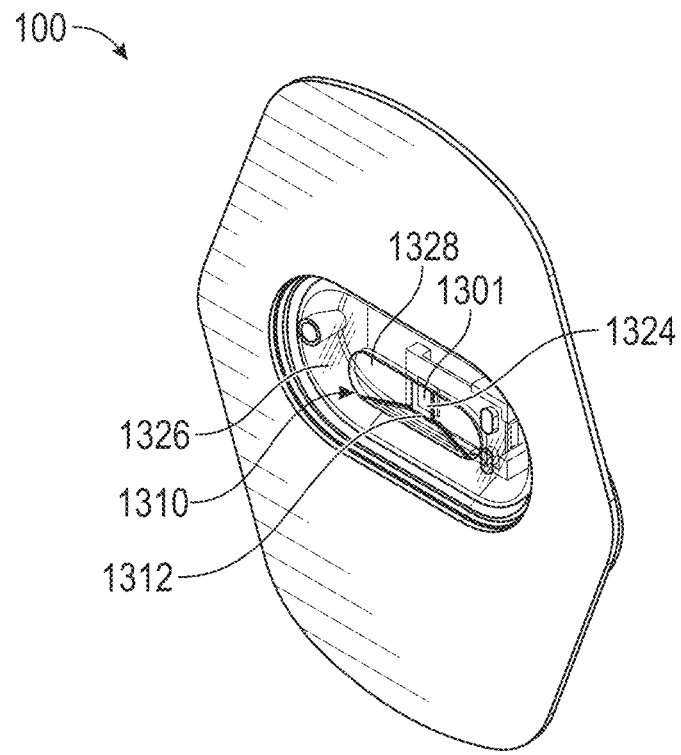
FIG. 15A is a back isometric view of the module from FIG. 13A showing an aperture in a cover aligned with a camera lens of the camera sensor.
Figure 15B:
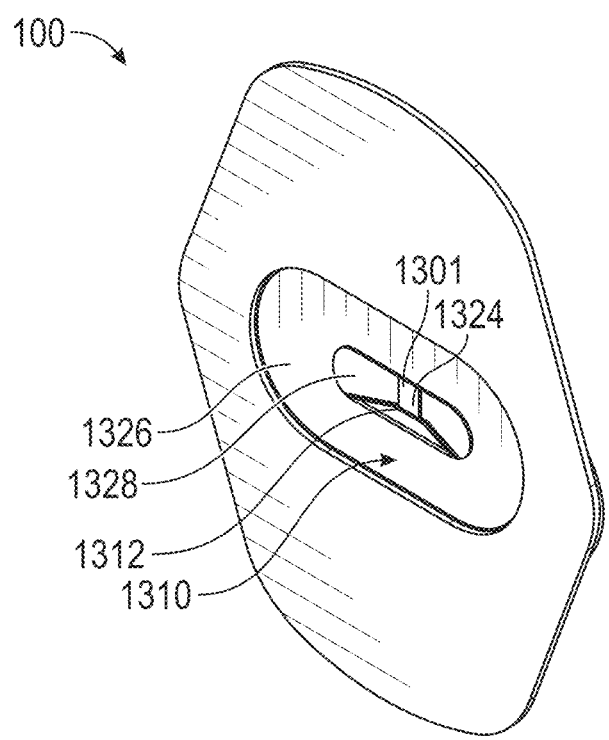
FIG. 15B is a back isometric view similar to FIG. 15A except the cover is opaque.
Figure 16A:
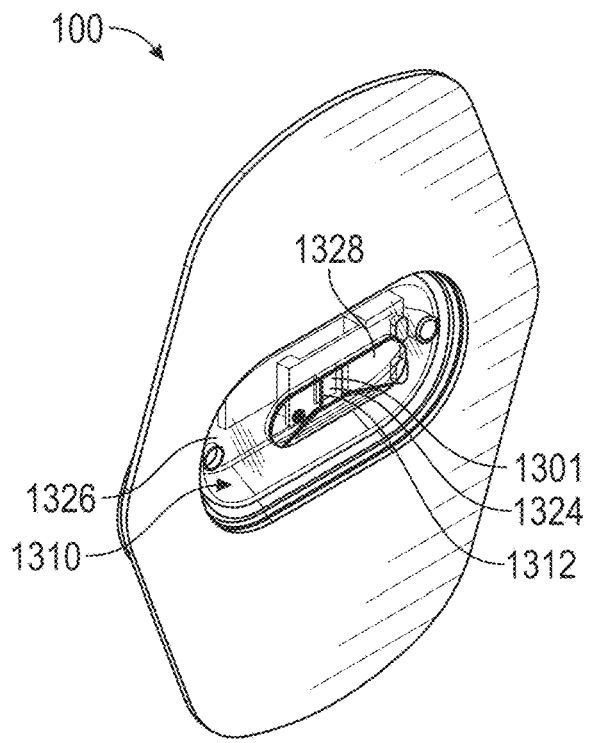
FIG. 16A is another back isometric view of the module from FIG. 13A.
Figure 16B:
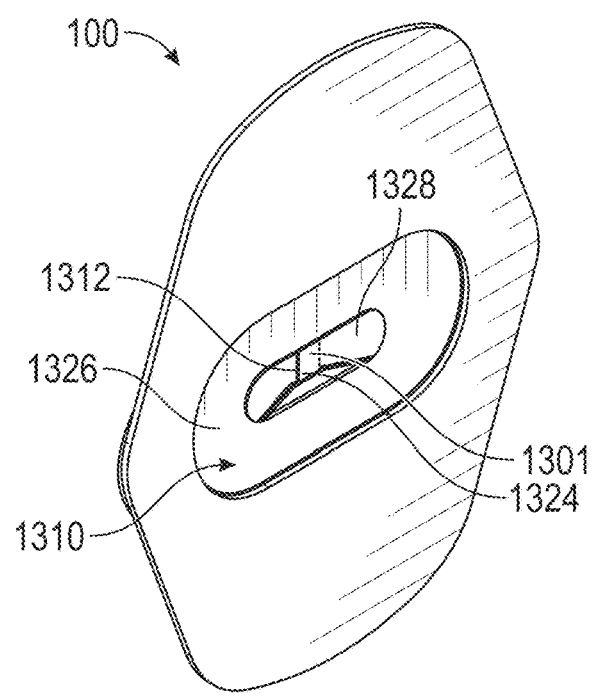
FIG. 16B is another back isometric of the module from FIG. 13A.

FIG. 15A is a back isometric view of the module 100 from FIG. 13A showing an aperture 1312 in the cover 1310 aligned with a camera lens 1324 of the camera sensor 1301. FIG. 15B is a back isometric view similar to FIG. 15A except the cover 1310 is opaque. FIGS. 16A and 16B are back isometric views of the module 100 from FIG. 13A.

As is illustrated in FIGS. 15A and 16A, the camera sensor 1301 is supported by the PCB 1304. In the illustrated embodiment, the camera sensor 1301 is positioned on the PCB 1304 to correspond to the aperture 1312 in the cover 1310. In this way, the camera lens 1324 has an unobstructed view of the wound or area of the patient's skin. In certain embodiments, the cover 1310 need not comprise the aperture 1312. For example, in certain embodiment, a portion of the cover 1310 that is aligned with the camera lens 1324 is transparent allowing the camera lens 1324 to have an unobstructed view of the wound or area of the patient's skin.

In certain embodiments, the camera module 1301 (and or PCB 1304) is secured within the receptacle 1308 by one or more fasteners 1334 so as to inhibit undesirable movement of the camera sensor 1301 relative to the module 100. For example, the camera sensor 1301 can be located on the PCB 1304 such that the camera sensor 1301 aligns with the aperture 1312 in the cover 1310 when the PCB 1304 is positioned and secured in the housing 1302 and the cover 1310 is secured to the opening into the receptacle 1308. In some embodiments, this position lies generally at the center of the cover 1310. In certain embodiments, the aperture 1312 is sized so as to provide a close fit with a perimeter of the camera sensor 1301. In this way, the aperture 1312 can further inhibit undesirable movement of the camera sensor 1301 relative to the module 100.

In certain embodiments, the cover 1310 comprises an outer portion 1326 and an inner portion 1328. In certain embodiments, the outer portion 1326 has a generally planar shape. In certain embodiments, the inner portion 1328 is sized and shaped to connect an inner edge of the outer portion 1326 with the aperture 1312. In certain embodiments, the inner portion 1328 forms a recess or concave shape in the back of the housing 1302. In certain embodiments, by recessing the aperture 1312 within the housing 1302, the camera sensor 1301 is supported above the patient's skin when the cover 1310 is secured to the opening in the receptacle 1308. In certain embodiments, by raising the camera lens 1324 away from the patient's skin, the camera sensor 1301 achieves a desirable field of view. As explained above, the module 100 can comprises additional structures (dressing thickness and/or manual application of force) to further move or adjust the camera sensor 1301 between a low-profile state and a raised profile state.

Figure 17:
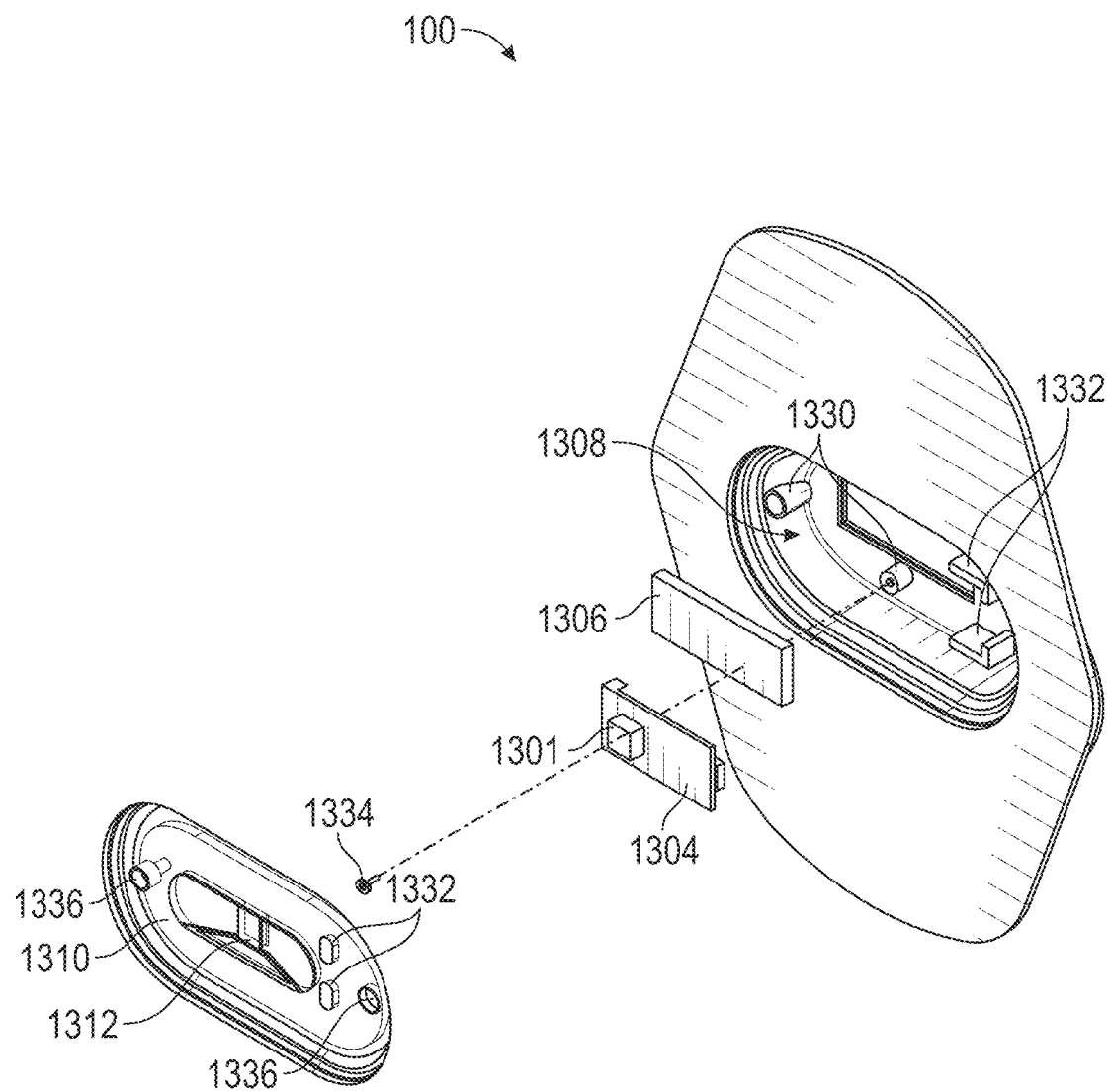
FIG. 17 is an exploded view of the module from FIG. 13A showing the sensor module and the battery removed from the receptacle.
Figure 18:
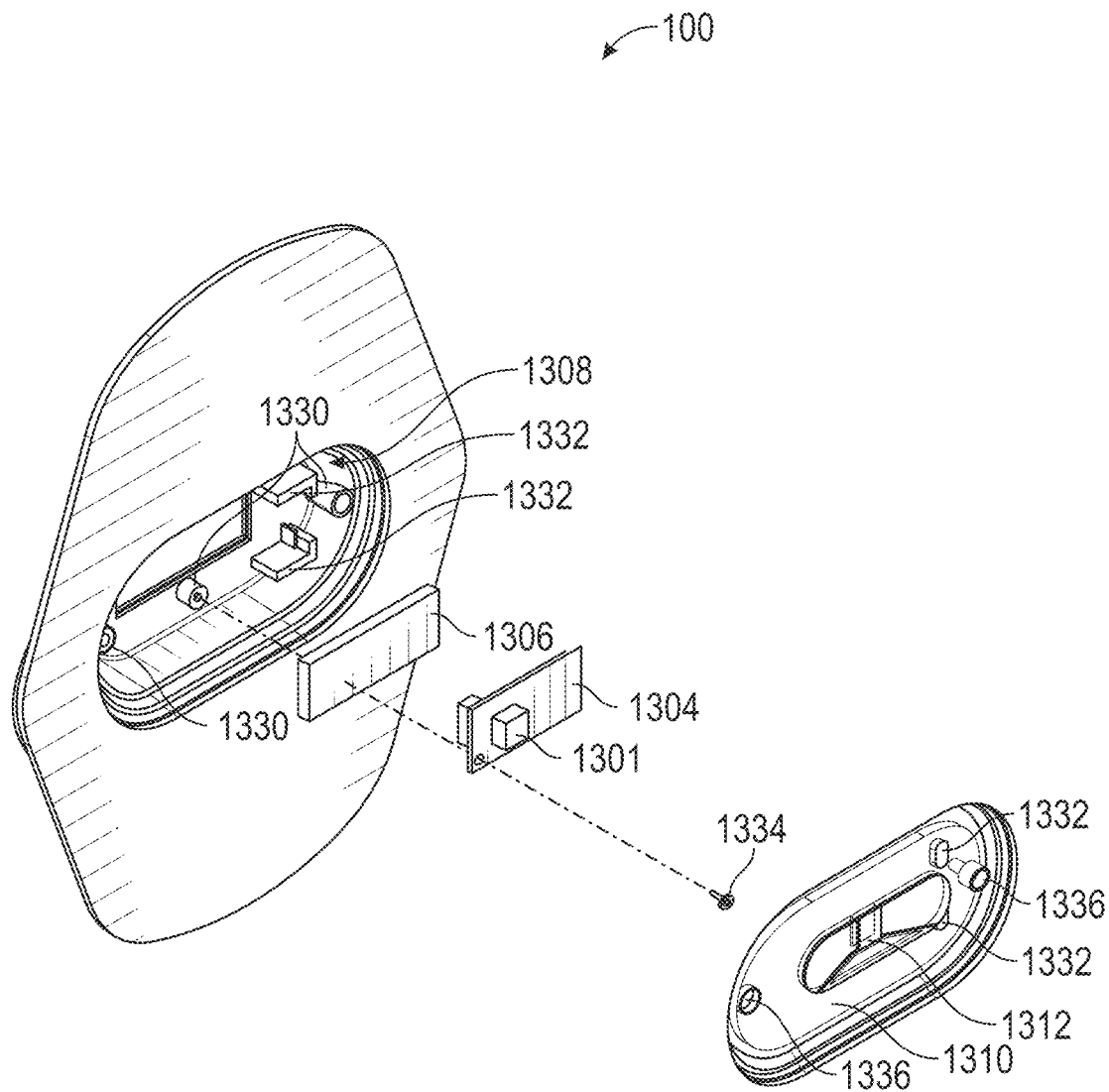
FIG. 18 is another exploded view of the module from FIG. 13A showing the sensor module and the battery removed from the receptacle.

FIG. 17 is an exploded view of the module 100 from FIG. 13A showing the PCB 1304 and the battery 1306 removed from the receptacle 1308. FIG. 18 is another exploded view of the module 100 from FIG. 13A showing the PCB 1304 and the battery 1306 removed from the receptacle 1308. In the illustrated embodiment, the camera sensor 1301 is disposed on the PCB 1304. The PCB 1304 can support one or more sensors/components including the camera sensor 1301. In certain embodiments, the one or more sensors/components comprise any of the sensors/components described with respect to FIGS. 1, 2 and 20 (e.g., controller/processor 104, sensors 102, optical elements 1314, led indicators 1338, battery safety circuit 1340, data storage 106, power interface 109, and/or network interface 108, etc.). In certain embodiments, the PCB 1304 also can support and interconnect at least some components of the treatment dispenser 110 and/or the fluid treatment storage 112. For example, in some embodiments, the treatment dispenser 110 can include a dispensing medicant pump or the like that draws fluid from the fluid treatment storage 112 when operated by the controller 104.

In certain embodiments, the receptacle 1308 comprises a mounting structure for connecting to components (e.g., PCB 1304, battery 1306, cover 1310) of the module 100. In certain embodiments, the components secure to the housing 1302 via one or more complementary engagement structures including, for example, adhesives, fasteners, detents, projections, guide walls, recesses, or other known securement structures. For example, in certain embodiments, the back side of the receptacle 1308 comprises one or more receptacles 1330 and/or guide walls 1332. The one or more receptacles 1330 are configured to receive one or more fasteners 1334 so as to connect the components to the housing 1302. For example, in certain embodiments, a fastener 1334 secures the PCB 1304 to the housing 1302. In certain embodiments, the battery 1306 is located between the one or more guide walls 1332 while also being sandwiched between the PCB 1304 and the back wall of the receptacle 1308. In this way, once the fastener 1334 securing the PCB 1304 to the housing 1302 is removed, the PCB 1304 and the battery 1306 are easily removed from the receptacle 1308.

Figure 19B:
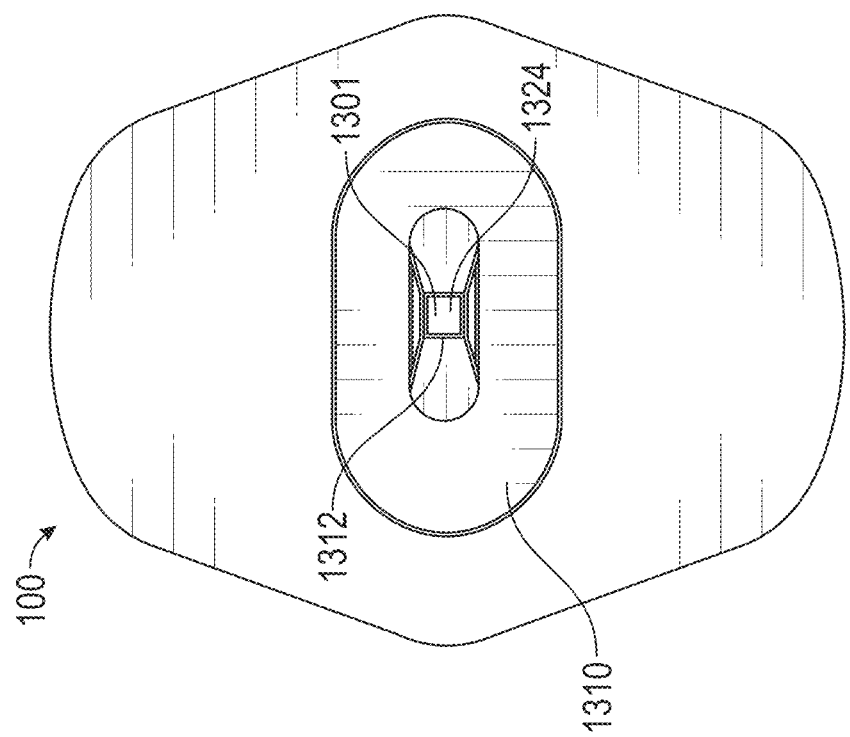
FIG. 19B is a back plan view similar to FIG. 19A except the cover is opaque.
Figure 19A:
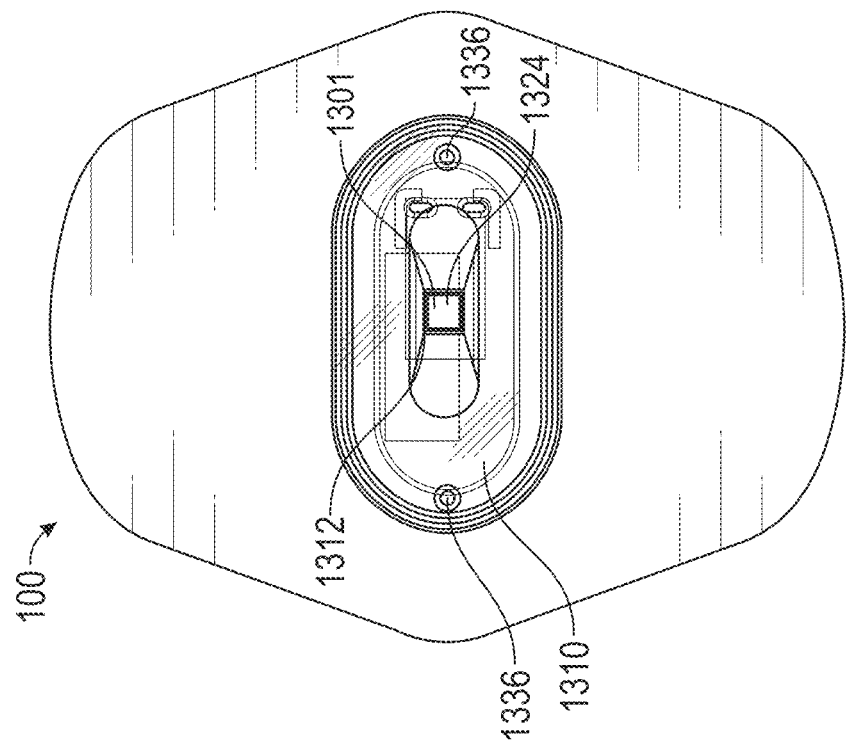
FIG. 19A is a back plan view of the module from FIG. 13A showing the aperture in the cover aligned with the camera lens of the sensor module.

FIG. 19A is a back plan view of the module 100 from FIG. 13A showing the aperture 1312 in the cover 1310 aligned with the camera lens 1324 of the camera sensor 1301. FIG. 19B is a back plan view similar to FIG. 19A except the cover 1310 is opaque. In certain embodiments, a portion of the cover 1310 is press fit into the housing 1302 securing the cover 1310 to the housing 1302. In the illustrated embodiment, the cover 1310 comprises one or more apertures 1336 for receiving the one or more fasteners 1334 (not shown). In certain embodiments, once the one or more fasteners 1334 are disengaged from the one or more receptacles 1330, the cover 1310 can be removed to then lift out components from the receptacle 1308, separate, and separately recycled without further disassembly. For example, in certain embodiments, a healthcare provider at a hospital can place the disassembled components in their recycling program since, for example, the battery 1306 and other components meet requirements for disposal in a landfill. In other embodiments, the module 100 is reusable. For example, the reusable module 100 can be configured for removal and replacement of the battery 1306 along with the healthcare provider being able to change an electronic identifier of the module 100 for the new patient.

FIG. 20 is a schematic view of the module 100 from FIG. 13A. The treatment and analysis module 100 may include one or more sensors 102 to monitor and generate data regarding user skin characteristics. In certain embodiments, the one or more sensors 102 may include a visualization element, such as the camera sensor 1301, to capture images and/or generate other visualization data regarding the skin of the user. Such visualization data may be used to monitor a wound or other skin aspect over time, to diagnose a skin condition, to determine a treatment for a skin condition, and/or to monitor the treatment of a skin condition over time. In certain embodiments, the one or more sensors 102 may also or alternatively include a temperature sensor to determine the temperature of the user's body surface region and/or the ambient temperature. In certain embodiments, the one or more sensors 102 may also or alternatively include an accelerometer to assess movements and activities of the patient. In certain embodiments, the one or more sensors 102 may also or alternatively include a pH sensor to determine the pH level of the user's body surface region. In some embodiments, the one or more sensors 102 may also or alternatively include a moisture sensor to determine the moisture content of the user's body surface region and/or the ambient moisture around a location of the user's body surface region. The example sensors 102 described herein are illustrative only, and are not intended to be limiting, required, or exhaustive of the sensors 102 that may be included in a treatment and analysis module 100.

The treatment and analysis module 100 may include the processor/controller 104, such as a system on a chip ("SOC") or other microprocessor to process data and commands. In some embodiments, the processor 104 may process data from the one or more sensors 102 and/or a data store 106, execute one or more analysis or detection algorithms, receive and execute commands from other devices via the network interface 108, or the like. In some embodiments, the data store 106 may be a substantially persistent data store, such as flash memory, hard disk, or the like.

The network interface 108 may be a wired or wireless network interface, such as a network adapter card and/or a wireless antenna (e.g., a Wi-Fi antenna, a Bluetooth® antenna, etc.). For example, the network interface 108 can utilize RF, infrared or other wireless circuitry (receiver or transmitter, or transceiver) to communicate with a remote device. In certain embodiments, the network interface 108 is implemented as a Wi-Fi module and/or a cellular module. In certain embodiments, the network interface 108 comprises an antenna.

In the illustrated embodiment, the network interface 108 is on the same PCB 1304 as other electronics and located within the housing 1302. In certain embodiments, the Wi-Fi module connects the components of the PCB 1304 to a LAN via a Wi-Fi connection. In certain embodiments, multiple modules 100 with multiple network interfaces 108 connect to a single LAN.

In certain embodiments, the network interface 108 comprises a cellular module. In certain embodiments, the cellular module communicates to the Internet via a mobile carrier's network. Depending on the location and carrier, various standards, such as GPRS, GSM, and CDMA, and the like may apply.

In certain embodiments, a lower surface of the module 100 (e.g., cover 1310) supports a series of optical elements 1314, for example, LEDs and lasers. The optical elements 1314 can be used to illuminate the skin or wound to enhance imaging, for light therapy to help improve or heal the skin condition or wound, or both. In certain embodiments, the optical elements 1314 provide waveform-based treatments, such as ultraviolet light or ultrasound. In certain embodiments, the optical elements 1314 emit UV light (e.g., UVA (315-400 nm), UVB (280-315 nm), and/or UVC (200-280 nm)). Exemplary indications of use for light therapy include using ultraviolet light to treat disorders of the skin (e.g., psoriasis, acne vulgaris, eczema and neonatal jaundice, etc.). For example, the optical elements 1314 can emit UVC to kill pathogens without unacceptable damage to host tissue of the patient. UVB can stimulate wound healing. UV sources can include light-emitting diodes, lasers, and microwave-generated UV plasma. In certain embodiments, the optical elements 1314 emit low level laser therapy for treatment of the wound. In certain embodiments, microwave-generated ultraviolet plasma may be used therapeutically.

In certain embodiments, the optical elements 1314 are configured for fluorescence imaging (e.g., near-infrared fluorescence imaging). In certain embodiments, data obtained from fluorescence imaging visualizes bacteria to assist wound treatment by the healthcare provider. For example, the optical elements 1314 can detect bacterial loads and location with respect to the wound. The bacterial loads can be used by the physician to assess or reassess clinical treatment of the wound.

In certain embodiments, the processor/controller 104 on the PCB 1304 can control the optical elements 1314 while the battery 1306 powers the optical elements 1314. Alternatively, the PCB 1304 can support the optical elements 1314 with the optical elements 1314 aligned with apertures in the cover 1310 of the housing 1302 or employ a transparent cover 1310 without the need for apertures.

In certain embodiments, the battery 1306 supplies power to the one or more sensors/components of the module 100. In certain embodiments, the battery 1306 attaches to the components by one or more detachable leads. The battery 1306 can be rechargeable either by an external port on the housing 1302 or by inductive charging (i.e., wireless) as explained above. In certain embodiments, the battery 1306 is a rechargeable lithium ion battery with a voltage of 3.7. Of course, the type and capacity of the battery 1306 are not limited to the listed type and value and instead can be any other type of battery 1306 having any other capacity or value. In certain embodiments, the battery 1306 is about 4.5 mm thick, 52.5 mm long, and 20.7 mm wide. The dimensions of the battery 1306 can be selected to be similar to the dimensions of the PCB 1304 (e.g., PCB 1304—4.87 mm thick, 52.33 mm long, and 21.05 mm wide) for the exemplary battery 1306 dimensions provided above. The size of the battery 1306 can be selected to allow the module 100 to operate for at least one day before requiring charging. In certain embodiments, the battery 1306 can be recharged while the module 100 is attached to the patient wirelessly or via a wired connection.

In certain embodiments, the module 100 includes a battery safety circuit 1340. For example, in certain embodiments, the battery safety circuit 1340 is configured so that the module 100 complies with International Electrotechnical Commission ("IEC") 62133 (Safety requirements for portable sealed secondary lithium cells, and for batteries made from them, for use in portable applications). In this way, the dimensions of the battery 1306 and its re-chargeable characteristics comply with the standard. In certain embodiments, the battery safety circuit 1340 allows safe inductive charging of the battery 1306. In certain embodiments, the battery safety circuit 1340 is incorporated on the PCB 1304.

In certain embodiments, the module 100 includes the camera lens 1324. In certain embodiments, the camera lens 1324 can be auto-focusing, rotatable or otherwise movable, and/or able to zoom in or out. In certain embodiments, the module 100 includes a manual slide control for angle and viewing. In certain embodiments, the manual slide control is located on a side of the housing 1302 to allow the healthcare provider to adjust the lens 1324 to cover the best viewing distance and angle. In certain embodiments, the module 100 includes a motor slide control for angle and viewing. In certain embodiments, the motor slide control can be controlled remotely. These features allow the user (or controller 104 if automated) to capture images of all or substantially all of the affected area (e.g., the wound) or targeted skin area, as well as to image segments of the affected or targeted area (e.g., the wound's margins and healed boundaries). For these purposes, the processor/controller 104 can control the camera lens 1324 with the battery 1306 supplying power thereto. In other embodiments, the lens 1324 can be fix. Additional filters (either physical or software) can be used to enhance the images.

In certain embodiments, the module 100 includes the treatment dispenser 110 and/or the fluid treatment storage 112. For example, in some embodiments, the treatment dispenser 110 can include a dispensing medicant pump or the like that draws fluid from the fluid treatment storage 112 when operated by the processor 104. A lower surface of the module 100 can include one or more apertures. Such apertures can form part of the treatment dispenser 110 to apply a treatment agent (e.g., a therapeutic, topical fluids, ozone, etc.) to the patient's skin/wound.

In certain embodiments, the aperture(s) can also form part of a negative pressure wound therapy module 1342. For example, in certain embodiments, the negative pressure wound therapy module 1342 can draw fluids from within a space between the wound and the lower surface of the module 100 to reduce the pressure within that space. In certain embodiments, the negative pressure wound therapy module 1342 comprises the space (e.g., a fluid collection container) and a vacuum pump. One or more tubes can channel fluid between the wound dressing, the fluid collection container, and the vacuum pump.

Figure 21A:
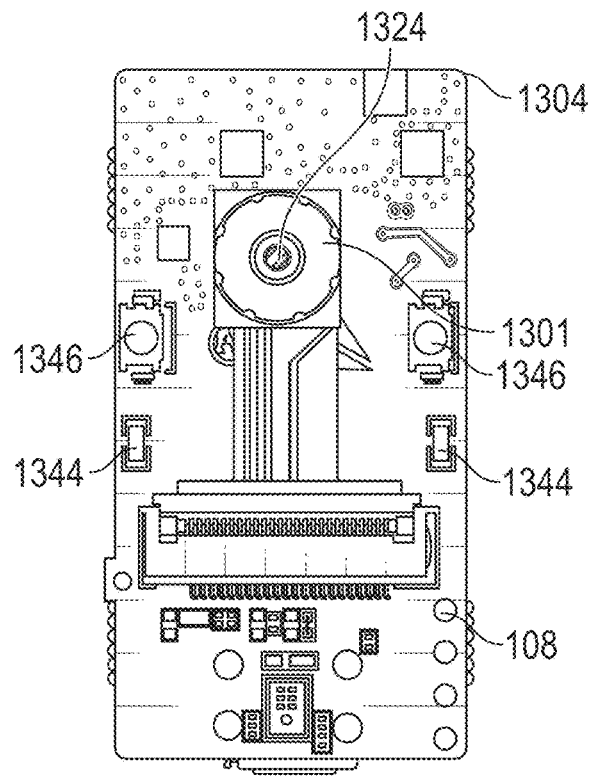
FIG. 21A is a plan top view of the PCB from FIG. 13A.
Figure 21B:
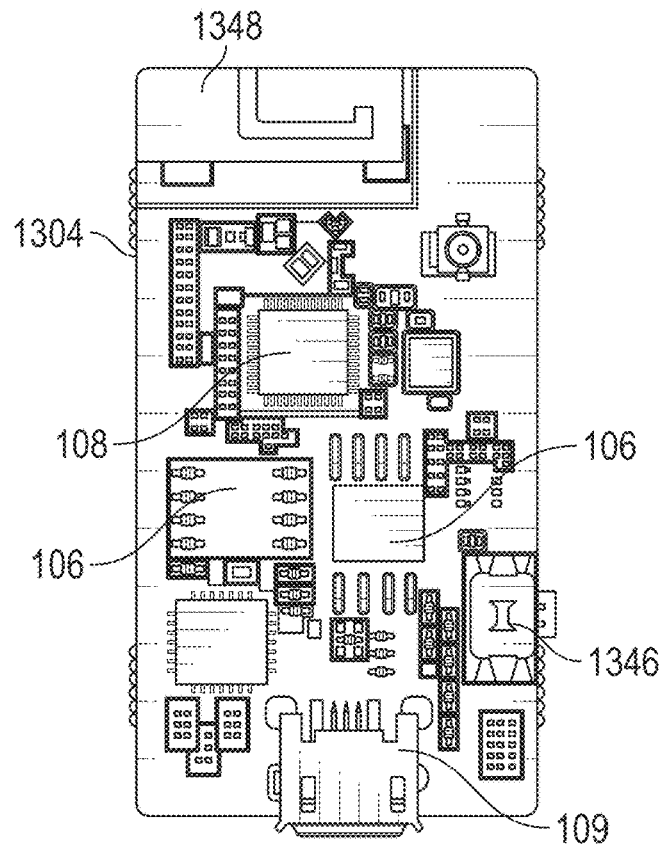
FIG. 21B is a back side view of the PCB from FIG. 21A.

FIG. 21A is a plan top view of an exemplary embodiment of the PCB 1304 (e.g., including camera sensor 1301) from FIG. 13A. FIG. 21B is a back side view of the PCB 1304 from FIG. 21A. FIGS. 21A-B illustrate certain of the one or more sensors/components of the module 100 but are not intended to limit the number of components that can be carried by the PCB 1304 to those illustrated. One or more of any of the components disclosed herein can be carried by the PCB 1304 (or multiple PCBs 1304) and/or module 100.

In certain embodiments, the PCB 1304 comprises an antenna 1348. In certain embodiments, the antenna 1348 is configured as a planar inverted-F antenna (PIFA). In certain embodiments, the network interface 108 of the PCB 1304 comprises a wireless chip. In certain embodiments, the wireless chip is configured as a Wi-Fi and/or Bluetooth chip.

In certain embodiments, the network interface 108 of the PCB 1304 comprises a port for data transmission. In certain embodiments, the port is configured as a serial peripheral interface (SPI) port. In certain embodiments, the antenna 1348 and the port are employed by the network interface 108 to receive and send data by the module 100. The network interface 108 may be a wired or wireless network interface, such as a network adapter card and/or a wireless antenna (e.g., a Wi-Fi antenna, a Bluetooth® antenna, etc.).

In certain embodiments, the PCB 1304 comprises one or more buttons 1346 for controlling/programming the components disposed on the PCB 1304. In certain embodiments, the PCB 1304 comprises one or more LED indicators 1344.

In certain embodiments, the power interface 109 can be a wired or wireless interface, such as a receiver configured to receive power via a time-varying electromagnetic field (e.g., inductive coupling, resonant inductive coupling, capacitive coupling, magneto dynamic coupling, microwaves, and light waves, etc.) and convert the power back to an electric current. In the illustrated embodiment, the power interface 109 is configured as a USB port. Of course, the power interface 109 need not be configured as a USB port and instead can be configured as any other type of port for receiving power. In certain embodiments, the power interface 109 supplies power to all of the components of the PCB 1304. In certain embodiments, the data store 106 may be a substantially persistent data store, such as flash memory, hard disk, or the like.

FIG. 22A is a perspective view of the PCB 1304 from FIG. 13A. FIG. 22B is a front plan view of the PCB 1304 from FIG. 22A. FIG. 22C is a side view of the PCB 1304 from FIG. 22B. FIG. 22D is an upper plan view of the PCB 1304 from FIG. 22A. The dimensions disclosed in FIGS. 22A-D are only exemplary and are not intended to limit the size of the PCB 1304 in any way. As explained above, in certain embodiments, the dimensions of the battery 1306 can be selected to be similar to the dimensions of the PCB 1304 (e.g., PCB 1304—4.87 mm thick, 52.33 mm long, and 21.05 mm wide) for the exemplary battery 1306 dimensions provided above.

Figures 23A, 23B:
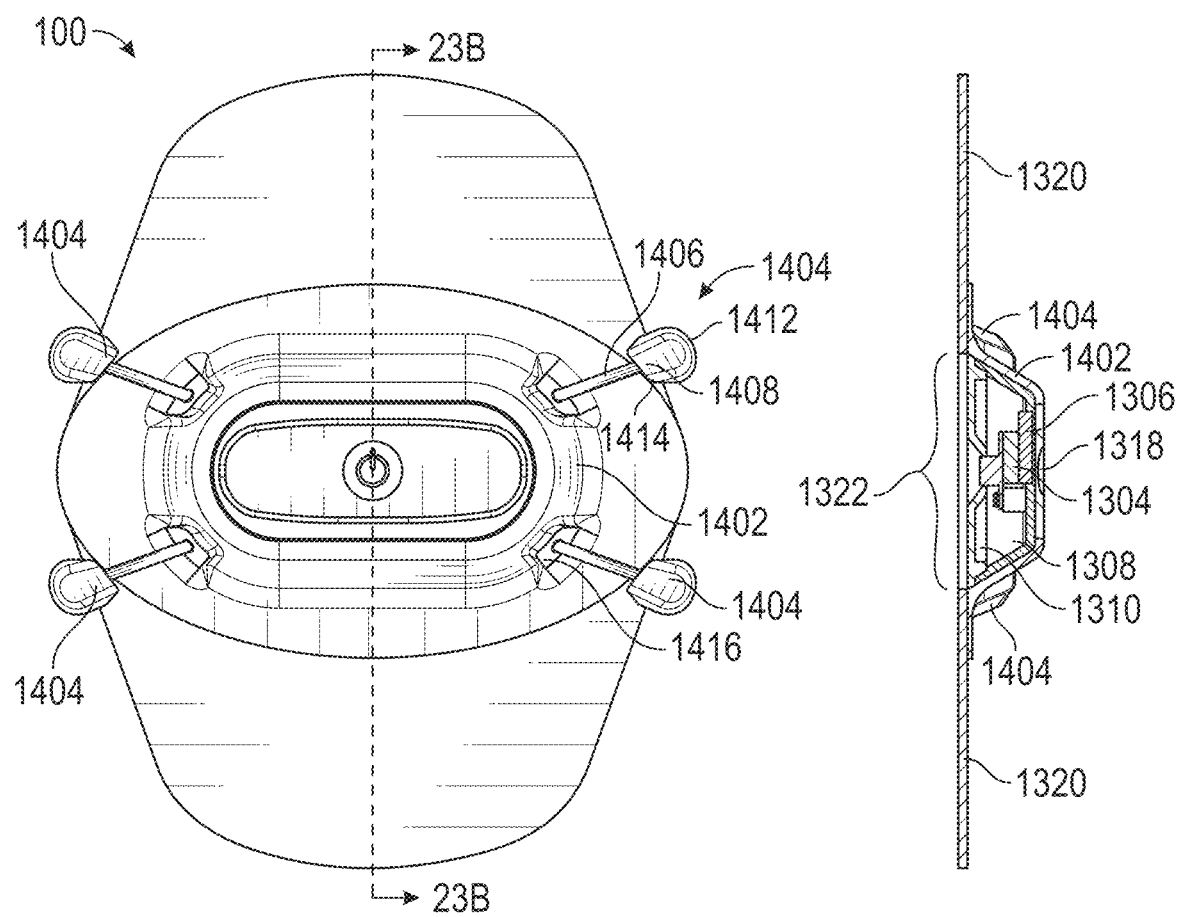
FIG. 23A is a top plan view of another embodiment of the treatment and analysis module that is similar to the module of FIG. 13A except the housing comprises one or more legs in an extended configuration.
FIG. 23B is a cross-section view through the module in FIG. 23A showing the one or more legs in the extended configuration.

FIG. 23A is a top plan view of another embodiment of the treatment and analysis module 100 that is similar to the module 100 of FIG. 13A except the housing 1402 comprises one or more legs 1404 which telescope from the housing 1402. In certain embodiments, the one or more legs 1404 are movable between extended and retracted configurations. In certain embodiments, the one or more legs 1404 are fixed in the extended configuration.

In certain embodiments, the one or more legs 1404 can extend from the module 100 at a location above or below the platform 1320. For example, the one or more legs 1404 in FIGS. 23A to 26B extend from the housing 1402 at a location that is above the platform 1320 while the one or more legs 1404 in FIGS. 27A to 29B extend from the housing 1502 at a location that is below the platform 1320. In certain embodiments that include multiple legs 1404, the multiple legs 1404 can be internally linked so that the multiple legs 1404 move in unison when any one of the legs 1404 is moved between the extended and retracted configurations.

When in the extended configuration, the module 100 can be placed over larger wound areas than when the one or more legs 1404 are in the retracted configuration. In certain embodiments, the one or more legs 1404 allow for the module 100 to be centered or placed in any location on the patient with the one or more legs 1404 extending beyond an outer perimeter of the platform 1320. In certain embodiments, the one or more legs 1404 extend to a dressing encircling the wound. In certain embodiments, the one or more legs 1404 are affixed in place by, for example, surgical/medical tape, or a foam riser that is affixed to the skin of the patient.

In certain embodiments, a surgical foam pad may be sized and/or shaped to cover or substantially cover a wound and, in some cases, the body surface around or adjacent to the wound. The surgical foam pad may have an aperture to provide would access to the module 100 or components thereof (e.g., optical access for a camera sensor; environmental access for a temperature or moisture sensor, etc.). One or more legs 1404 may extend to maintain the module 100 at a height above the body surface and/or to be embedded within the surgical foam pad.

In certain embodiments, the one or more legs 1404 provide for increased height to enlarge the field of view or coverage for one or more components of the module 100 (e.g., for the camera sensor 1301). In this way, the user (e.g., a healthcare provider) can increase the housing's profile manually by extending the one or more legs 1404. In certain embodiments, the module 100 can include an actuating system (e.g., one or more electric or pneumatic actuators) to extend the one or more legs 1404 or to move the camera sensor 1301 (or other components within the housing 1402 (e.g., the PCB 1304)) relative to the patient's wound or skin.

The one or more legs 1404 in FIG. 23A are in the extended configuration. The illustrated embodiment comprises four legs 1404. However, the module 100 can comprise more or fewer legs 1404 than is illustrated in FIG. 23A. FIG. 23B is a cross-section view through the module 100 in FIG. 23A showing the one or more legs 1404 in the extended configuration. In the illustrated embodiment, each leg 1404 comprises a rod 1406 having a distal end 1408. In certain embodiments, the rod 1406 and the distal end 1408 comprise different materials. For example, in certain embodiments, the rod 1406 comprises stainless steel while the distal end 1408 is an over molded plastic to the rod 1406. Of course the material of the rod 1406 need not be stainless steel and instead can be any other material.

As is illustrated in FIG. 23A, an outer portion 1412 of the distal end 1408 can have a generally U-shape as viewed in FIG. 23A. As also illustrated in FIG. 23A, an inner portion 1414 of the distal end 1408 can have a surface that matches a pad 1416 on an outer surface of the housing 1402. In certain embodiments, the inner portion 1414 contacts the pad 1416 when the leg 1404 is in the retracted configuration. Of course the shapes of the inner portion 1414 and pad 1416 are not limited to the illustrated shapes.

Figure 24B:
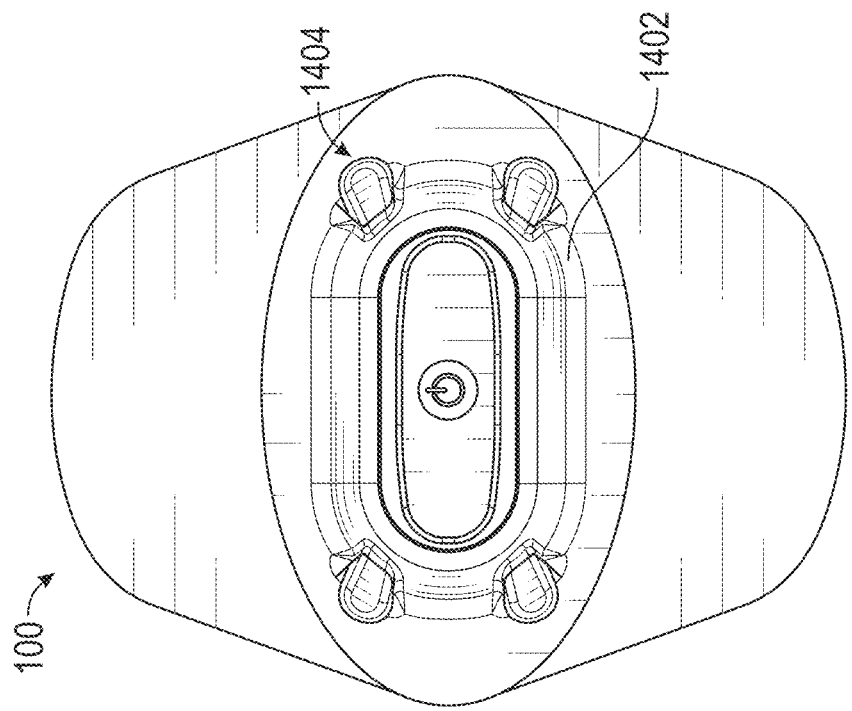
FIG. 24B is a top plan view similar to FIG. 24A except the one or more legs are in the retracted configuration.
Figure 24A:
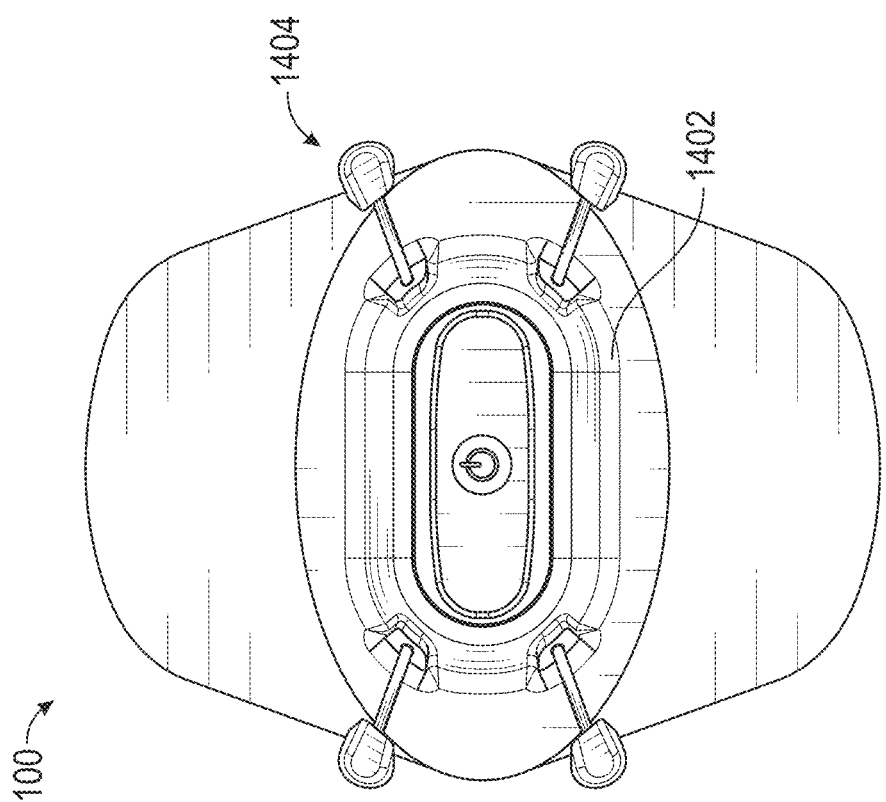
FIG. 24A is a top plan view of the module from FIG. 23A showing the one or more legs in the extended configuration.
Figure 25B:
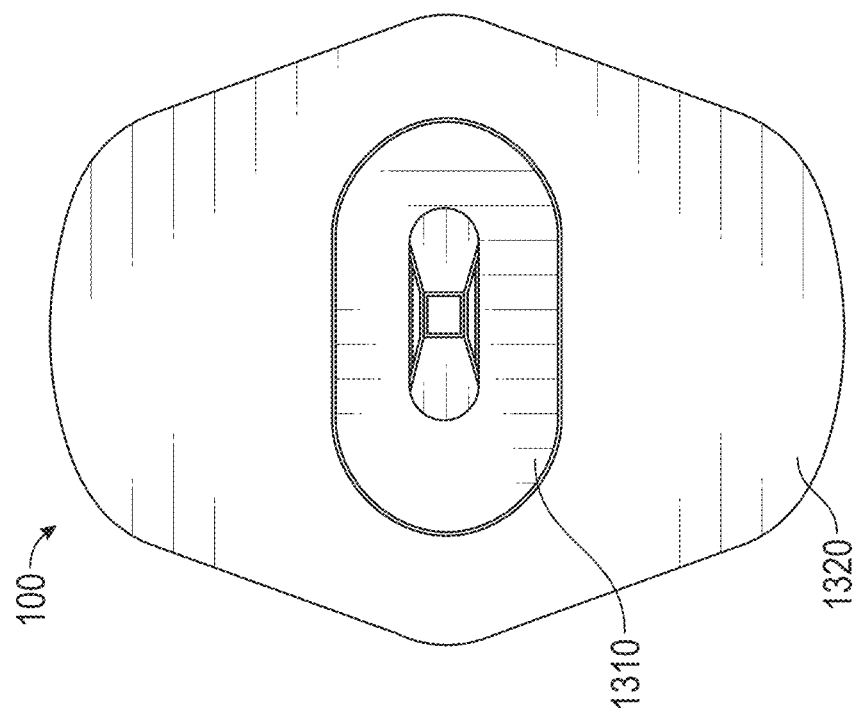
FIG. 25B is a back plan view similar to FIG. 25A except the one or more legs are in the retracted configuration hidden behind the platform.
Figure 25A:
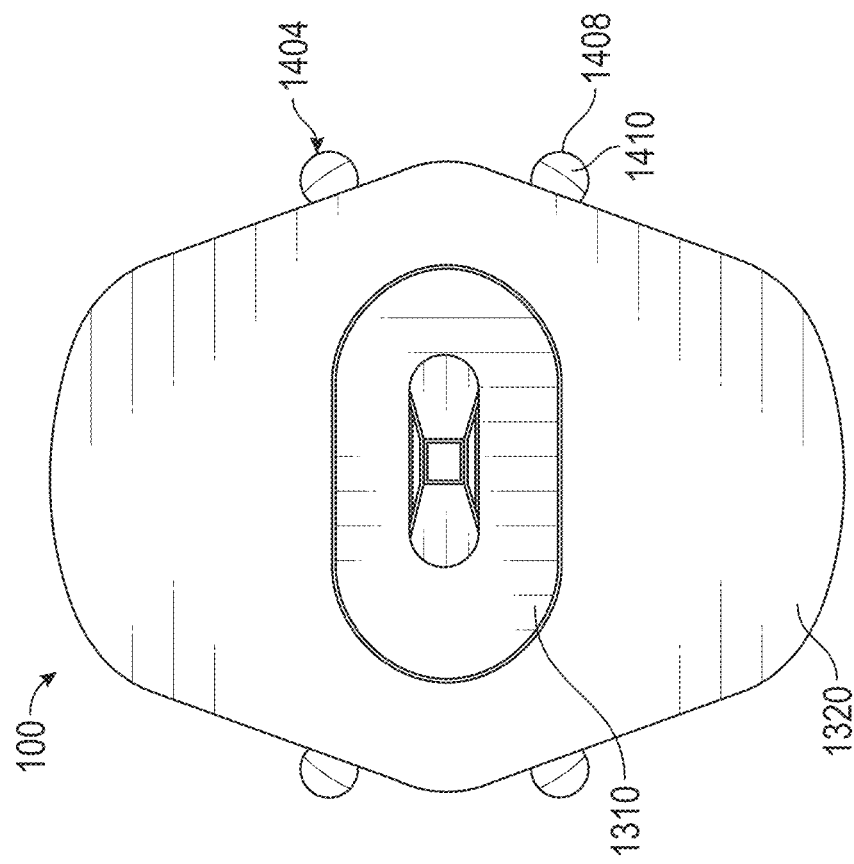
FIG. 25A is a back plan view of the module from FIG. 23A showing the one or more legs extending beyond an outer perimeter of the platform when in the extended configuration.

FIG. 24A is a top plan view of the module 100 from FIG. 23A showing the one or more legs 1404 in the extended configuration. FIG. 24B is a top plan view similar to FIG. 24A except the one or more legs 1404 are in the retracted configuration. FIG. 25A is a back plan view of the module 100 from FIG. 23A showing the one or more legs 1404 extending beyond an outer perimeter of the platform 1320 when in the extended configuration. FIG. 25B is a back plan view similar to FIG. 25A except the one or more legs 1404 are in the retracted configuration hidden behind the platform 1320. In certain embodiments, the distal end 1408 is sized larger than the rod 1406. In this way, the distal end 1408 comprises a contact surface 1410 that has a width greater than a width of the rod 1406. In certain embodiments, the contact surface 1410 provides sufficient stability to the module 100 when the contact surface 1410 is secured relative to the patient.

Figure 26B:
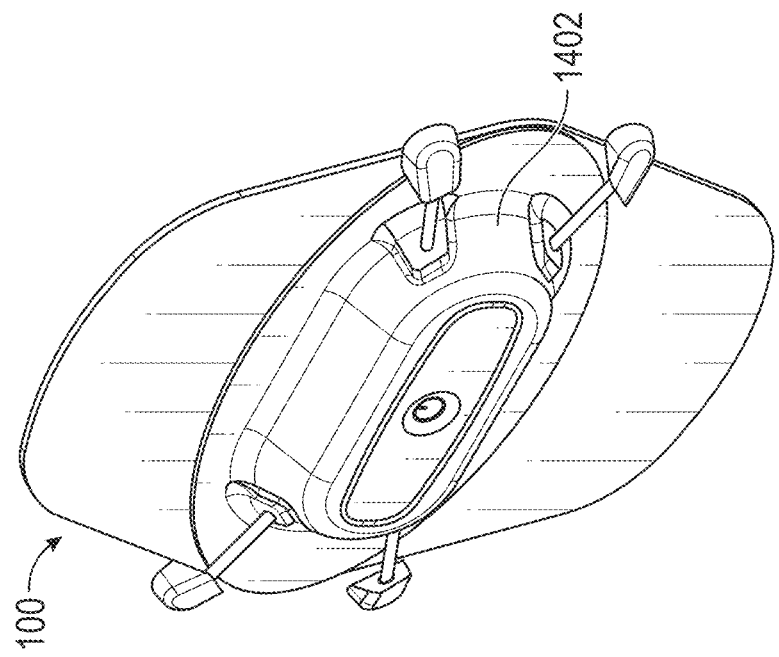
FIG. 26B is a right isometric view of the module from FIG. 23A showing the one or more legs in the extended configuration.
Figure 26A:
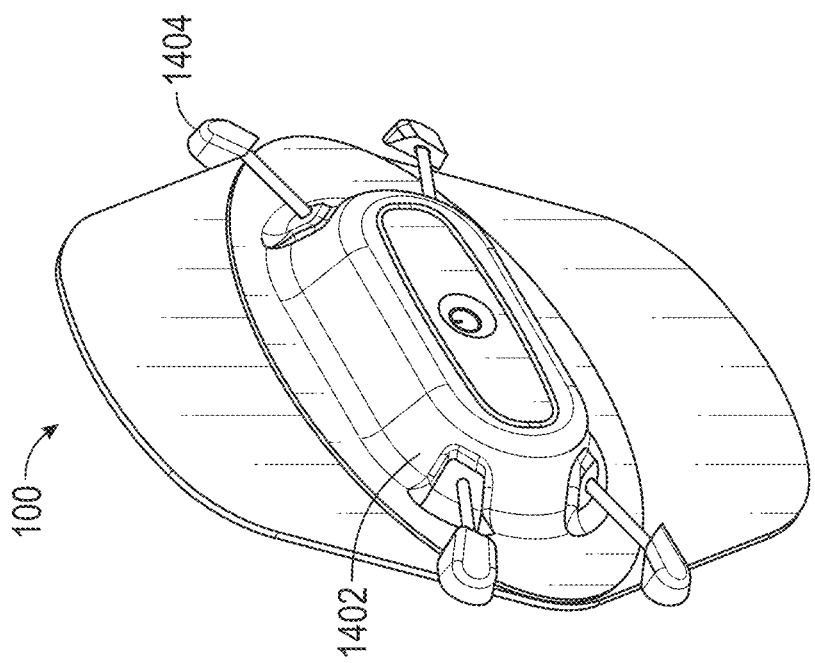
FIG. 26A is a left isometric view of the module from FIG. 23A showing the one or more legs in the extended configuration.

FIG. 26A is a left isometric view of the module 100 from FIG. 23A showing the one or more legs 1404 in the extended configuration. FIG. 26B is a right isometric view of the module 100 from FIG. 23A showing the one or more legs 1404 in the extended configuration.

FIG. 27A is a top plan view of another embodiment of the treatment and analysis module 100 that is similar to the module 100 of FIG. 23A except the one or more legs 1404 extend from the housing 1502 at a location below the platform 1320. In the illustrated embodiment, the one or more legs 1404 extend from the cover 1510. FIG. 27B is a cross-section view through the module 100 in FIG. 27A showing the one or more legs 1404 in the extended configuration.

In certain embodiments, the one or more legs 1404 are movable between extended and retracted configurations. In certain embodiments that include multiple legs 1404, the multiple legs 1404 can be internally linked so that the multiple legs 1404 move in unison when any one of the legs 1404 is moved between the extended and retracted configurations.

Figure 28B:
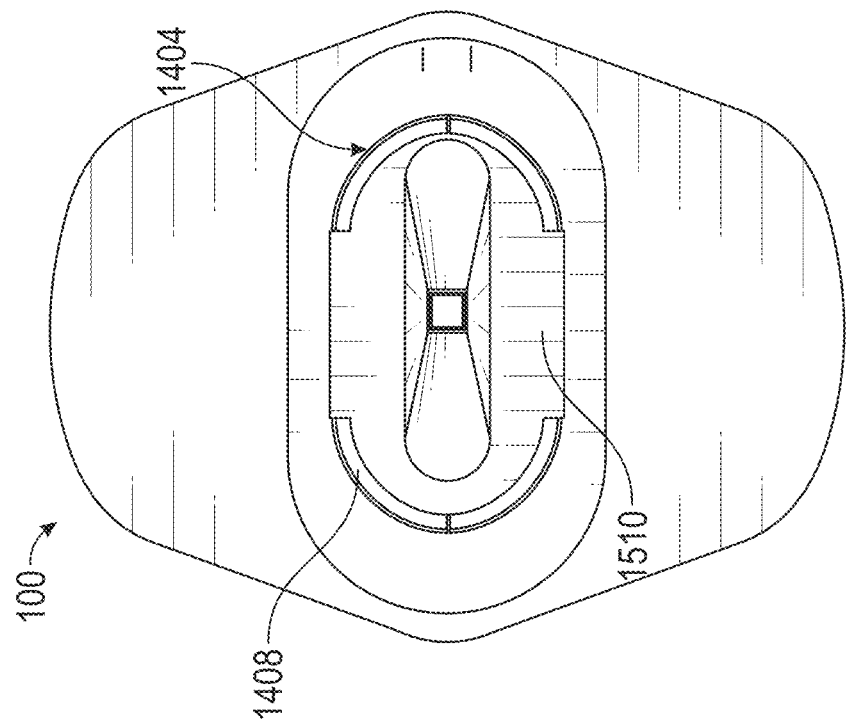
FIG. 28B is a back plan view similar to FIG. 28A except the one or more legs are in the retracted configuration.
Figure 28A:
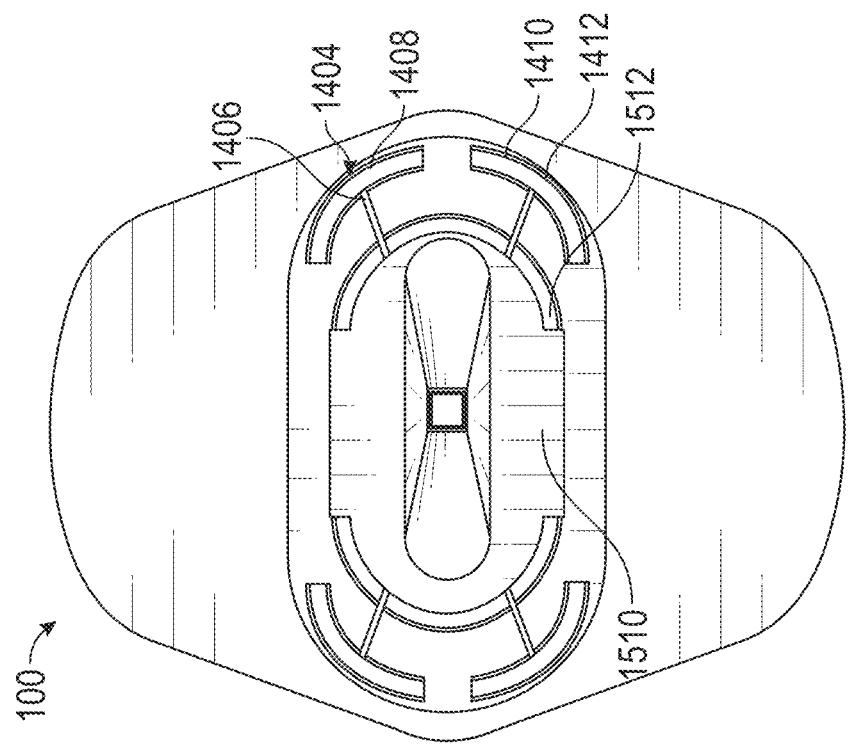
FIG. 28A is a back plan view of the module from FIG. 27A showing the one or more legs in the extended configuration.

FIG. 28A is a back plan view of the module 100 from FIG. 27A showing the one or more legs 1404 extending from the cover 1510 and in the extended configuration. FIG. 28B is a back plan view similar to FIG. 28A except the one or more legs 1404 are in the retracted configuration. In certain embodiments, the one or more legs 1404 provide for increased height to enlarge the field of view or coverage for one or more components of the module 100 (e.g., for the camera sensor 1301). In this way, the user (e.g., a healthcare provider) can increase the housing's profile manually by extending the one or more legs 1404. In certain embodiments, the module 100 can include an actuating system (e.g., one or more electric or pneumatic actuators) to extend the one or more legs 1404 or to move the camera sensor 1301 (or other components within the housing 1302 (e.g., the PCB 1304)) relative to the patient's wound or skin.

The illustrated embodiment comprises four legs 1404. However, the housing 1510 can comprise more or fewer legs 1404 than is illustrated in FIG. 28A. In the illustrated embodiment, each leg 1404 comprises a rod 1406 having a distal end 1408. In certain embodiments, the rod 1406 and the distal end 1408 comprise different materials. For example, in certain embodiments, the rod 1406 comprises stainless steel while the distal end 1408 is over molded plastic to the rod 1406. Of course the material of the rod 1406 need not be stainless steel and instead can be any other material.

As is illustrated in FIG. 28A, an outer portion 1412 of the distal end 1408 can have a general arc shape as viewed in FIG. 28A. As also illustrated in FIG. 28A, the cover 1510 can comprise a channel 1512 sized and shaped to receive the distal end 1408 when the one or more legs 1404 are in the retracted configuration. In certain embodiments, the distal end 1408 is sized and shaped to match the channel 1512 in the cover 1510. Of course the shapes of the distal end 1408 and the channel 1512 are not limited to the illustrated shapes.

Figure 29B:
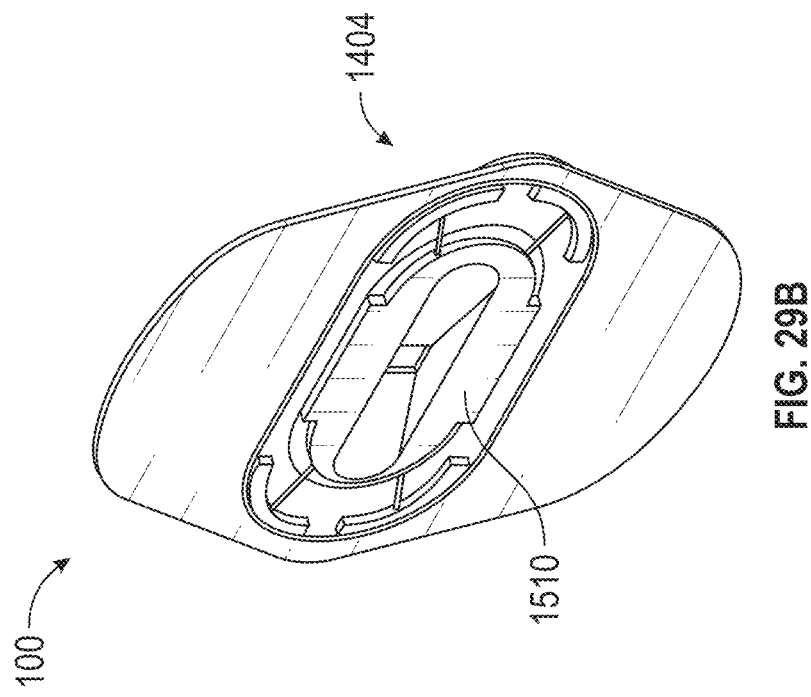
FIG. 29B is a right isometric view of the module from FIG. 27A showing the one or more legs in the extended configuration.
Figure 29A:
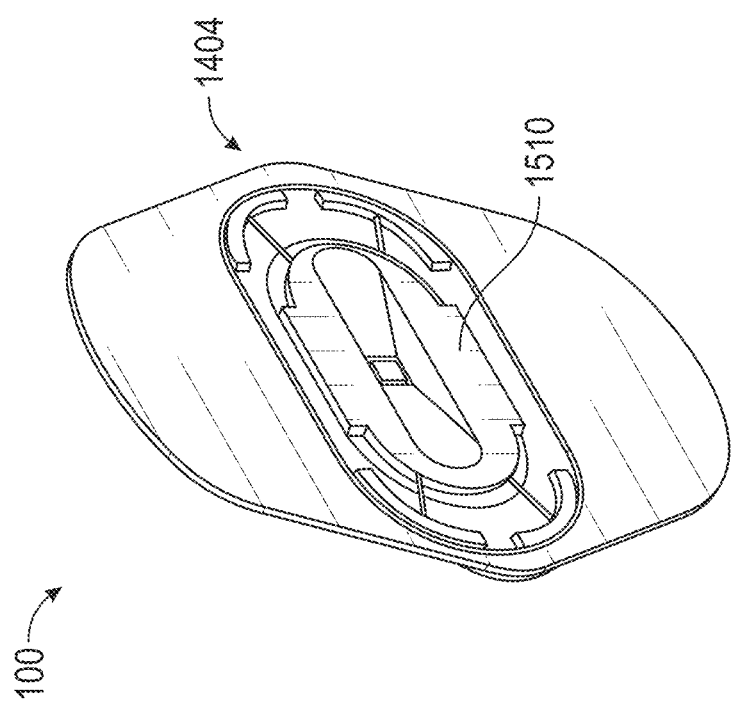
FIG. 29A is a left isometric view of the module from FIG. 27A showing the one or more legs in the extended configuration.

FIG. 29A is a left isometric view of the module 100 from FIG. 27A showing the one or more legs 1404 in the extended configuration. FIG. 29B is a right isometric view of the module 100 from FIG. 27A showing the one or more legs 1404 in the extended configuration. In certain embodiments, the distal end 1408 is sized larger than the rod 1406. In this way, the distal end 1408 comprises a contact surface 1410 that has a width greater than a width of the rod 1406. In certain embodiments, the contact surface 1410 provides stability to the module 100 when the contact surface 1410 is secured relative to the patient.

In some embodiments, one or more legs 1404 may be integrated with a bracket (not shown) that is placed over or near the body tissue region of interest. In this configuration, the one or more legs 1404 may provide vertical height adjustment for a separate module 100 that is coupled to (e.g., securely snapped into place on) the bracket. Fixed-length or adjustable-length horizontal supports may extend from the bracket to facilitate securement of the bracket to a wearable medical article (e.g., medical foam) that surrounds or is near the body surface region of interest.

Although some examples and embodiments described herein relate to use of a module 100 with a wearable medical article, the examples are illustrative only and are not intended to be limiting. In some embodiments, the module 100 may be used during a procedure to help surgeons and/or robotic operators carry out delicate maneuvers and avert damage to adjacent tissues and organs. The module can provide intra-operative imaging and/or other sensor data for intelligent instrumentation that facilitates real-time surgical navigation of critical structures. In orthopedics, surgeons may experience reduced complexity, reduced operating room time, increased operating room turnover, all within a footprint that is designed to serve both ambulatory surgical centers and specialty hospital settings.

The materials used in the embodiments disclosed herein can be any suitable types of materials. For example, the materials can be selected such that the module materials are suitable for repeated exposures to body and treatment fluids. The module materials can be suitable for repeated exposure to autoclave or other clinically utilized sterilization processes. In some of the disclosed embodiments, replaceable components of the module can be suitable for one-time exposure to body and treatment fluids. Those materials can be suitable for exposure to gamma sterilization or any other suitable sterilization process.

Terminology

Depending on the embodiment, certain acts, events, or functions of any of the processes or algorithms described herein can be performed in a different sequence, can be added, merged, or left out altogether (e.g., not all described operations, sequencing, or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or combinations of electronic hardware and computer software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a computer processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A computer processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

Reference throughout this specification to "some embodiments" or "an embodiment" means that a particular feature, structure, element, act, or characteristic described in connection with the embodiment is included in at least one embodiment. Thus, appearances of the phrases "in some embodiments" or "in an embodiment" in various places throughout this specification are not necessarily all referring to the same embodiment and may refer to one or more of the same or different embodiments. Furthermore, the particular features, structures, elements, acts, or characteristics may be combined in any suitable manner (including differently than shown or described) in other embodiments. Further, in various embodiments, features, structures, elements, acts, or characteristics can be combined, merged, rearranged, reordered, or left out altogether. Thus, no single feature, structure, element, act, or characteristic or group of features, structures, elements, acts, or characteristics is necessary or required for each embodiment. All possible combinations and sub-combinations are intended to fall within the scope of this disclosure.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

The foregoing description sets forth various example embodiments and other illustrative, but non-limiting, embodiments of the inventions disclosed herein. The description provides details regarding combinations, modes, and uses of the disclosed inventions. Other variations, combinations, modifications, equivalents, modes, uses, implementations, and/or applications of the disclosed features and aspects of the embodiments are also within the scope of this disclosure, including those that become apparent to those of skill in the art upon reading this specification. Additionally, certain objects and advantages of the inventions are described herein. It is to be understood that not necessarily all such objects or advantages may be achieved in any particular embodiment. Thus, for example, those skilled in the art will recognize that the inventions may be embodied or carried out in a manner that achieves or optimizes one advantage or group of advantages as taught herein without necessarily achieving other objects or advantages as may be taught or suggested herein. Also, in any method or process disclosed herein, the acts or operations making up the method or process may be performed in any suitable sequence and are not necessarily limited to any particular disclosed sequence.

The following is claimed:

1. A wearable medical module for embedding within a medical dressing over a wound on a body surface of a patient, comprising:
   a housing forming a receptacle having a lower opening configured to face the wound, wherein the housing comprises a flange configured to be embedded within the medical dressing;
   a camera sensor, battery, and wireless antenna sized and shaped to be disposed in the receptacle;
   a cover disposed over the lower opening and having an aperture aligned with the camera sensor so that the camera sensor has a field of view of the wound through the aperture; and
   a plurality of legs extendable from the housing towards the body surface of the patient so as to adjust a distance between the camera sensor and the wound on the body surface;
   wherein the camera sensor is configured to generate image data regarding the wound when the housing is embedded within the medical dressing, and wherein the wireless antenna is configured to transmit the image data.

2. The wearable medical module of claim 1, further comprising a treatment dispenser configured to administer a fluid treatment to the wound, wherein the fluid treatment is stored in a fluid treatment storage in fluid communication with the treatment dispenser.

3. The wearable medical module of claim 1, further comprising a treatment dispenser configured to administer, to the wound, at least one of a light therapy or an ultrasonic therapy.

4. The wearable medical module of claim 1, further comprising a negative pressure wound therapy module configured to draw fluids from within a space between the wound and a lower surface of the wearable medical module to reduce pressure within the space.

5. The wearable medical module of claim 1, further comprising a treatment dispenser configured to administer a treatment to the wound, wherein the wireless antenna is further configured to receive an instruction to administer the treatment.

6. The wearable medical module of claim 5, wherein the instruction is associated with a treatment regimen, and wherein the treatment dispenser is configured to implement the treatment regimen by administration of the treatment according to a schedule.

7. The wearable medical module of claim 5, wherein the wireless antenna is further configured to receive a second instruction to generate second image data regarding the wound subsequent to administration of the treatment.

8. The wearable medical module of claim 1, wherein the wireless antenna is further configured to:
   receive an instruction, initiated by a remote device, to provide the image data to the remote device; and
   provide the image data to the remote device, wherein the camera sensor generates the image data in response to the instruction.

9. The wearable medical module of claim 1, wherein further comprising one or more of: a temperature sensor, a moisture sensor, a pH sensor, or a pressure sensor.

10. The wearable medical module of claim 1, wherein the plurality of legs are configured to move from an extended configuration to a retracted configuration, wherein in the extended configuration, the plurality of legs maintain a higher profile of the housing with respect to the body surface than when the plurality of legs are in the retracted configuration.

11. The wearable medical module of claim 1, wherein the plurality of legs extend from a lower surface of the housing.

12. The wearable medical module of claim 1, wherein the plurality of legs extend from an upper surface of the housing.

13. The wearable medical module of claim 1, wherein the battery is configured to be wirelessly charged.

14. The wearable medical module of claim 1, wherein the medical dressing comprises a surgical foam pad.

15. The wearable medical module of claim 1, wherein the medical dressing comprises a cast.

16. The wearable medical module of claim 1, wherein the medical dressing comprises a wrap.

17. A wearable medical module for embedding within a medical dressing over a wound on a body surface of a patient, comprising:
   a housing forming a receptacle having a lower opening configured to face the wound, wherein the housing has an upper surface facing away from the wound, and wherein the housing is configured to be embedded within the medical dressing such that at least a portion of the upper surface is covered by the medical dressing;
   a camera sensor disposed relative to the receptacle and configured to capture an image of the wound, wherein the camera sensor is configured to generate image data regarding the wound when the housing is embedded within the medical dressing; and
   a plurality of supports extendable from the housing towards the body surface of the patient so as to adjust a distance between the camera sensor and the wound on the body surface.

18. The wearable medical module of claim 17, further comprising a treatment dispenser configured to administer a fluid treatment to the wound, wherein the fluid treatment is stored in a fluid treatment storage in fluid communication with the treatment dispenser.

19. The wearable medical module of claim 17, further comprising a treatment dispenser configured to administer a light therapy treatment to the wound.

20. The wearable medical module of claim 17, wherein the medical dressing comprises at least one of a surgical foam pad, a cast, or a wrap.

21. A wearable medical module for embedding within a medical dressing over a wound on a body surface of a patient, comprising:
   a housing forming a receptacle having a lower opening configured to face the wound, wherein the housing is configured to be embedded within the medical dressing;

a camera sensor at least partially disposed in the receptacle and configured to capture an image of the wound; and a plurality of supports extendable from the housing towards the body surface of the patient so as to adjust a distance between the camera sensor and the body surface within which the wound is located;

wherein the camera sensor is configured to generate image data regarding the wound without removal of the medical dressing from the body surface of the patient.

22. The wearable medical module of claim 21, further comprising:

a treatment dispenser configured to administer a treatment to the wound; and a wireless antenna configured to receive an instruction to administer the treatment.

23. The wearable medical module of claim 22, wherein the instruction is associated with a treatment regimen, and wherein the treatment dispenser is configured to implement the treatment regimen by administration of the treatment according to a schedule.

24. The wearable medical module of claim 22, wherein the wireless antenna is further configured to receive a second instruction to generate second image data regarding the wound subsequent to administration of the treatment.

25. The wearable medical module of claim 21, further comprising a wireless antenna configured to:

receive an instruction, initiated by a remote device, to provide the image to the remote device; and provide the image to the remote device, wherein the camera sensor generates the image in response to the instruction.

26. The wearable medical module of claim 21, wherein the medical dressing comprises at least one of a surgical foam pad, a cast, or a wrap.

27. A wearable medical module for embedding within a surgical foam pad over a patient's wound on a body surface of a patient and real-time monitoring of healing of the patient's wound, comprising:

a housing having a lower surface, wherein the housing comprises a flange configured to be embedded within the surgical foam pad;

a plurality of supports extendible from the housing towards the body surface of the patient and configured to adjust a distance between the lower surface and the patient's wound;

an optical instrument supported by the housing and configured to capture an image of the patient's wound when the housing is embedded within the surgical foam pad; and a transmitter configured to wirelessly transmit the captured image.

28. The wearable medical module of claim 27, wherein further comprising one or more of: a temperature sensor, a moisture sensor, a pH sensor, or a pressure sensor.

29. The wearable medical module of claim 27, wherein the plurality of supports are configured to move from an extended configuration to a retracted configuration.

30. The wearable medical module of claim 27, further comprising a treatment dispenser configured to administer a light therapy treatment to the wound.

* * * * *